United States Patent [19]
Fujita et al.

[11] Patent Number: 5,886,014
[45] Date of Patent: Mar. 23, 1999

[54] BENZIMIDAZOLE DERIVATIVES, THEIR PREPARATION AND THEIR THERAPEUTIC USE

[75] Inventors: Takashi Fujita; Kunio Wada; Minoru Oguchi; Hiroaki Yanagisawa; Koichi Fujimoto; Toshihiko Fujiwara; Hiroyoshi Horikoshi; Takao Yoshioka, all of Tokyo, Japan

[73] Assignee: Sankyo Company, Limited, Tokyo, Japan

[21] Appl. No.: 657,041

[22] Filed: May 31, 1996

[30] Foreign Application Priority Data

Jun. 1, 1995 [JP] Japan ................................. 8-045845
Jun. 1, 1995 [JP] Japan ................................. 7-135097

[51] Int. Cl.$^6$ ........................ A01N 43/78; C07D 271/06; C07D 277/62; C07D 417/00
[52] U.S. Cl. ........................ 514/369; 514/376; 514/394; 548/132; 548/159; 548/165; 548/226; 548/304.7
[58] Field of Search ..................................... 548/132, 159, 548/165, 226, 304.7; 514/369, 376, 394

[56] References Cited

U.S. PATENT DOCUMENTS

| 4,572,912 | 2/1986 | Yoshioka et al. | 514/369 |
| 4,691,027 | 9/1987 | Yoshioka et al. | 549/32 |
| 4,775,687 | 10/1988 | Meguro et al. | 514/369 |

(List continued on next page.)

FOREIGN PATENT DOCUMENTS

| 0 008 203 | 2/1980 | European Pat. Off. . |
| 0 139 421 | 5/1985 | European Pat. Off. . |
| 0 177 353 | 4/1986 | European Pat. Off. . |

(List continued on next page.)

OTHER PUBLICATIONS

Sohda et al, "Studies on Antidiabetic Agents. II.$^{1)}$ Synthesis of 5-4-(1-Methylcyclohexylmethoxy)benzyl]thiazolidine-2,4-dione (ADD-3878) and Its Derivatives", Chem. Pharm. Bull., 30, pp. 3580-3600(1982).

Fujita et al, "Reduction of Insulin Resistance in Obese and/or Diabetic Animals . . . a New Antidiabetic Agent", Diabetes, vol. 32, Sep. 1983, pp. 804-810.

Fujiwara et al, "Characterization of New Oral Antidiabetic Agent CS-045", Diabetes, vol. 37, Nov. 1988, pp. 1549-1558.

Chang et al, "The Hypoglycemic Effect of Ciglitazone in Obese, Hyperglycemic Animal Models", Prog. Clin. Biol. Res., 265, (1988) pp. 177-192.

Colca et al, "Ciglitazone, A Hypoglycemic Agent: Early Effects on the Pancreatic Islets of Ob/Ob Mice", Metabolism, vol. 37, No. 3, Mar. 1988, pp. 276-280.

Sohda et al, "Studies on Antidiabetic Agents", Arzneimittelforschung, Drug Res. 40(I), (1990) pp. 37-42.

Ikeda et al, "Effects of Pioglitazone on Glucose and Lipid Metabolism in Normal and Insulin Resistant Animals", Arzneimittelforschung, 40(2 Pt 1), (1990) pp. 156-162.

Sugiyama et al, "Effects of Pioglitazone on Glucose and Lipid Metabolism in Wistar Fatty Rats", Arzneimittelforschung, 40(3), (1990), pp. 263-267.

Colca et al, "Pioglitazone Hydrochloride Inhibits Cholesterol Absorption and Lowers Plasma Cholesterol Concentrations in Cholesterol-Fed Rats", Diabetes, vol. 40, Dec. 1991, pp. 1669-1674.

Saha et al, "Lipid abnormalities in tissues of the KKA$^y$ mouse: effects of pioglitazone on malonyl-CoA and diacylglycerol", Am. J. Physiol., 267(1 Pt 1), (1994) pp. E95-E101.

Oakes et al, "A New Antidiabetic Agent, BRL 49653, Reduces Lipid Availability and Improves Insulin Action and Glucoregulation in the Rat", Diabetes, vol. 43, Oct. 1994, pp. 1203-1210.

Bowen, "The Effect of CP 68,722, a Thiozolidinedione Derivative, on Insulin Sensitivity in Lean and Obese Zucker Rats", Metabolism, vol. 40, No. 10, Oct. 1991, pp. 1025-1030.

Kemnitz et al, "Pioglitazone Increases Insulin Sensitivity, Reduces Blood Glucose, Insulin, and Lipid Levels, and Lowers Blood Pressure in Obese, Insulin-Resistant Rhesus Monkeys", Diabetes, vol. 43, Feb. 1994, pp. 1025-1230.

Keen, "Insulin Resistance and The Prevention of Diabetes Mellitis", N. Engl. J. Med., 331(18), Nov. 1994, pp. 1226-1227.

Yoshioka et al, "Antihypertensive Effects of CS-045 Treatment in Obese Zucker Rats", Metabolism, vol. 42, No. 1, Jan. 1993, pp. 75-80.

Dubey et al, "Pioglitazone attenuates hypertension and inhibits growth of renal arteriolar smooth muscle in rats", Am. J. Physiol., 265(4 Pt 2), 1993, pp. R726-R732.

(List continued on next page.)

*Primary Examiner*—Mukund J. Shah
*Assistant Examiner*—Tamthom T. Ngo
*Attorney, Agent, or Firm*—Frishauf, Holtz, Goodman, Langer & Chick, P.C.

[57] ABSTRACT

Compounds of formula (I):

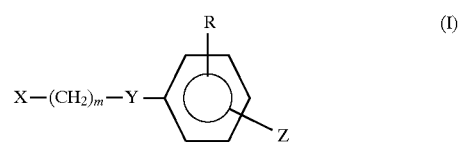

[wherein: X represents an optionally substituted benzimidazole group; Y represents an oxygen or sulfur atom; Z represents a 2,4-dioxothiazolidin-5-ylidenylmethyl, 2,4-dioxothiazolidin-5-ylmethyl, 2,4-dioxooxazolidin-5-ylmethyl, 3,5-dioxooxadiazolidin-2-ylmethyl or N-hydroxyureidomethlyl group; R represents hydrogen, alkyl, alkoxy, halogen, hydroxy, nitro, amino or aralkyl; and m is an integer from 1 to 5]; have valuable activity for the treatment and/or prophylaxis of a variety of disorders, including one or more of: hyperlipemia, hyperglycemia, obesity, impaired glucose tolerance (IGT), insulin resistance and diabetic complications.

116 Claims, No Drawings

U.S. PATENT DOCUMENTS

| | | | |
|---|---|---|---|
| 4,871,762 | 10/1989 | Yoshioka et al. | 514/439 |
| 4,873,255 | 10/1989 | Yoshioka et al. | 514/369 |
| 5,104,888 | 4/1992 | Yoshioka et al. | 514/369 |
| 5,143,930 | 9/1992 | Yoshioka et al. | 514/369 |
| 5,338,855 | 8/1994 | Yoshioka et al. | 514/369 |
| 5,387,596 | 2/1995 | Takebayashi et al. | 514/369 |
| 5,391,565 | 2/1995 | Hindley | 514/375 |
| 5,578,620 | 11/1996 | Fujita et al. | 514/370 |
| 5,614,542 | 3/1997 | Horikoshi et al. | 514/369 |
| 5,614,544 | 3/1997 | Sohda et al. | 514/376 |
| 5,624,935 | 4/1997 | Fujita et al. | 514/303 |
| 5,688,823 | 11/1997 | Fujita et al. | 514/376 |
| 5,739,345 | 4/1998 | Fujita et al. | 548/183 |

FOREIGN PATENT DOCUMENTS

| | | |
|---|---|---|
| 0 208 420 | 1/1987 | European Pat. Off. . |
| 0 306 228 | 3/1989 | European Pat. Off. . |
| 0 356 214 | 2/1990 | European Pat. Off. . |
| 0 441 605 | 8/1991 | European Pat. Off. . |
| 0 528 734 | 2/1993 | European Pat. Off. . |
| 0 676 398 | 10/1995 | European Pat. Off. . |
| 2183641 | 6/1987 | United Kingdom . |
| WO 91/07107 | 5/1991 | WIPO . |
| WO 92/02520 | 2/1992 | WIPO . |
| WO 92/03425 | 3/1992 | WIPO . |
| WO 92/07839 | 5/1992 | WIPO . |
| WO 92/07850 | 5/1992 | WIPO . |

OTHER PUBLICATIONS

Ohsumi et al, "Troglitazone Prevents the Inhibitory Effects of Inflammatory Cytokines on Insulin–Induced Anipocyte Differentiation in 3T3–L1 Cells" Endocrinology, vol. 135, No. 5, 1994, pp. 2279–2282.

Szalkowski et al, "Antidiabetic Thiazolidinediones Block the Inhibitory Effect of Tumor Necrosis Factor–$\alpha$ on Differentiation, Insulin–Stimulated Glucose Uptake, and Gene Expression in 3T3–L1 Cells", Endocrinology, vol. 136, No. 4, 1995, pp. 1474–1481.

Shikazumi et al, "The Effects of Pioglitazone on Glomerular Lesions in Wistar Fatty Rats", Journal of Japan Diabetes Society 38, 1995, (original copy and its English translation).

Zhang et al, "Effects of Pioglitazone on Calcium Channels in Vascular Smooth Muscle", Hypertension, vol. 24, No. 2, Aug. 1994, pp. 170–175.

Austin Patterson et al, The Ring Index, 2nd Edition, (American Chemical Society), p. 157 (1960).

Takao Yoshioka et al, "Studies on Hindered Phenols and Analogues. 1. Hypolipidemic and Hypoglycemic Agents with Ability To Inhibit Lipid Peroxidation", J. Med. Chem., vol. 32, 1989, pp. 421–428.

Takashi Sohda et al, "Studies on Antidiabetic Agents. 11.[1] Novel Thiazolidinedione Derivatives as Potent Hypoglycemic and Hypolipidemic Agents[2]", J. Med. Chem., vol. 35, 1992, pp. 2617–2626.

Joseph W. Kemnitz, Diane F. Elson, Ellen B. Roecker, Scott T. Baum, Richard N. Bergman and Martin D. Meglasson, "Pioglitazone Increases Insulin Sensitivity, Reduces Blood Glucose, Insulin, and Lipid Levels, and Lowers Blood Pressure in Obese, Insulin–Resistant Rhesus Monkeys", *Diabetes,* 43(2), 204–211 (1994).

BENZIMIDAZOLE DERIVATIVES, THEIR PREPARATION AND THEIR THERAPEUTIC USE

BACKGROUND TO THE INVENTION

The present invention relates to a series of benzimidazole compounds having hypoglycemic, anti-diabetic, anti-cataract and 5-lipoxygenase inhibitory activities, the ability to inhibit the formation of lipid peroxide and related activities, as described in more detail hereafter, and provides processes for their preparation and methods and compositions for their use.

Insulin and sulfonylurea compounds, including tolbutamide and glipizide, have been used for the treatment of diabetes mellitus and hyperglycemia. More recently, it has been discovered that compounds which, like those of the present invention, contain, inter alia, a thiazolidinedione, oxazolidinedione or related group attached, via a methylene or methylidene group, to a benzene ring have this type of activity, and have been proposed for the treatment of non-insulin-dependent diabetes mellitus.

(1) Many thiazolidine derivatives have been reported to have hypoglycemic activity, for example those described in: European Patent Publication No. 008203; European Patent Publication No. 139421; Chem. Pharm. Bull. 30, 3580–3600 (1982) by Y. Kawamatsu et al.; and in European Patent Publication No. 0441605.

(2) Compounds containing heterocyclic ring groups are disclosed in, for example: European Patent Publication No. 208420; European Patent Publication No. 528734; WO 92/07850A; WO 92/07839A; European Patent Publication No. 177353; European Patent Publication No. 306228; and European Patent Publication No. 356214.

(3) Oxazolidine-2,4-dione compounds having hypoglycemic activity are disclosed in, for example: WO 91/07107A; and WO 92/02520A.

(4) In addition, compounds containing an N-hydroxyureido group or a 3,5-dioxooxadiazolidin-2-ylmethylphenyl group and having this type of activity are disclosed in WO 92/03425A.

However, these compounds have a number of disadvantages, for example, their activity is inadequate or there are problems with their safety. Stronger and safer preventive and/or therapeutic agents for these diseases are therefore desired in practice.

The relationship between thiazolidine derivatives and various diseases is described in the following literature:

The effect of thiazolidine compounds on hyperglycemia has been reported in Diabetes 32(9), 804–810 (1983); Diabetes 37(11), 1549–1558 (1988); Prog. Clin. Biol. Res. 265, 177–192 (1988); Metabolism 37(3), 276–280 (1988); Arzneimittelforschung 40(1), 37–42 (1990); Arzneimittelforschung 40(2 Pt 1), 156–162 (1990); and Arzneimittelforschung 40(3), 263–267 (1990).

The effect of thiazolidine compounds on hyperlipidemia has been reported in Diabetes 40(12), 1669–1674 (1991); Am. J. Physiol. 267(1 Pt 1), E95–E101 (1994); and Diabetes 43(10), 1203–1210 (1994).

The effect of thiazolidine compounds on impaired glucose tolerance and insulin resistance has been reported in Arzneimittelforschung 40(2 Pt 1), 156–162 (1990); Metabolism 40(10), 1025–1230 (1991); Diabetes 43(2), 204–211 (1994); and N. Engl. J. Med. 331(18), 1226–1227 (1994).

The effect of thiazolidine compounds on hypertension has been reported in Metabolism 42(1), 75–80 (1993); Am. J. Physiol. 265 (4 Pt 2), R726–R732 (1993); and Diabetes 43(2), 204–211 (1994).

The effect of thiazolidine compounds on cachexia has been reported in Endocrinology 135(5), 2279–2282 (1994); and Endocrinology 136(4), 1474–1481 (1995).

The effect of thiazolidine compounds on nephropathy has been reported in the Journal of Japan Diabetes Society 38, Extra number (1995).

The effect of thiazolidine compounds on coronary artery diseases has been reported in Am. J. Physiol. 265(4 Pt 2), R726–R732 (1993); and Hypertension 24(2), 170–175 (1994).

The effect of thiazolidine compounds on arteriosclerosis has been reported in Am. J. Physiol. 265(4 Pt 2), R726–R732 (1993).

In addition, a high risk of diabetic occurrence has recently been reported in normal persons who have insulin resistance which is not accompanied by impaired glucose tolerance [in other words, insulin resistant non-IGT (NGT)] in N. Engl. J. Med. 331(18), 1226–1227 (1994). This fact suggests that an agent which can improve insulin resistance may be useful for the prevention of such diabetic occurrence in normal persons.

We have now discovered that the inclusion in such compounds of certain specific bicyclic nitrogen-containing ring systems results in compounds of much improved activity.

BRIEF SUMMARY OF INVENTION

Thus, it is an object of the present invention to provide a series of new chemical compounds which contain a benzimidazole ring and which may be regarded as thiazolidine and oxazolidine derivatives or as ring-opened derivatives thereof.

It is a further, and more specific, object of the invention to provide such compounds, at least some of which may be useful for the treatment and/or prophylaxis of a variety of disorders, including one or more of: hyperlipemia, hyperglycemia, obesity, impaired glucose tolerance (IGT), insulin resistance and diabetic complications.

Other objects and advantages of the present invention will become apparent as the description proceeds.

Thus, the present invention provides compounds of formula (I):

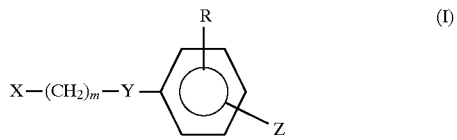

wherein:

X represents a benzimidazole group which is unsubstituted or is substituted by at least one substituent selected from the group consisting of substituents α, defined below;

Y represents an oxygen atom or a sulfur atom;

Z represents a group of formula (i), (ii), (iii), (iv) or (v):

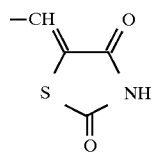
(i)

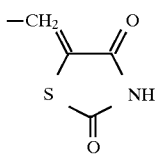
(ii)

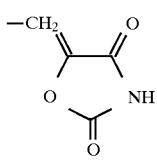
(iii)

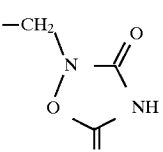
(iv)

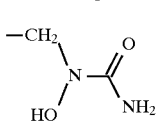
(v)

R represents:
a hydrogen atom;
an alkyl group having from 1 to 4 carbon atoms;
an alkoxy group having from 1 to 4 carbon atoms;
a halogen atom;
a hydroxy group;
a nitro group;
a group of formula —NR$^a$R$^b$,
in which R$^a$ and R$^b$ are the same or different and each represents a hydrogen atom, an alkyl group having from 1 to 8 carbon atoms, an aralkyl group in which an alkyl group having from 1 to 5 carbon atoms is substituted by a carbocyclic aryl group having from 6 to 10 carbon atoms; a carbocyclic aryl group having from 6 to 10 carbon atoms; an aliphatic acyl group having from 1 to 11 carbon atoms; an aryl-aliphatic acyl group in which an aliphatic acyl group having from 2 to 6 carbon atoms is substituted by at least one carbocyclic aryl group having from 6 to 10 carbon atoms; or an aromatic acyl group having from 7 to 11 carbon atoms; or
an aralkyl group in which an alkyl group having from 1 to 5 carbon atoms is substituted by a carbocyclic aryl group having from 6 to 10 carbon atoms; and
m represents an integer from 1 to 5;
said substituents α are selected from the group consisting of:
an alkyl group having from 1 to 4 carbon atoms;
an alkoxy group having from 1 to 4 carbon atoms;
a benzyloxy group;
a halogen atom;
a hydroxy group;
an acetoxy group;
a phenylthio group;
an alkylthio group having from 1 to 4 carbon atoms;
a trifluoromethyl group;
a nitro group;
a group of formula —NR$^a$R$^b$, in which R$^a$ and R$^b$ are as defined above;
a carbocyclic aryl group having from 6 to 10 carbon atoms which is unsubstituted or is substituted by at least one substituent selected from the group consisting of substituents β, defined below; or an aralkyl group in which an alkyl group having from 1 to 5 carbon atoms is substituted by a carbocyclic aryl group which has from 6 to 10 carbon atoms and which is unsubstituted or is substituted by at least one substituent selected from the group consisting of substituents β, defined below;
said substituents β are selected from the group consisting of alkyl groups having from 1 to 4 carbon atoms, alkoxy groups having from 1 to 4 carbon atoms, halogen atoms, hydroxy groups, nitro groups, phenyl groups, trifluoromethyl groups and groups of formula —NR$^a$R$^b$, in which R$^a$ and R$^b$ are as defined above;
and salts thereof.

The invention also provides a pharmaceutical composition for the treatment or prophylaxis of insulin resistance, diabetes, hyperglycemia, arteriosclerosis, cataracts, hyperlipemia, obesity, impaired glucose tolerance, hypertension, polycystic ovary syndrome, gestational diabetes mellitus or insulin resistant non-IGT, cataracts and complications thereof, which composition comprises an effective amount of an active compound in admixture with a pharmaceutically acceptable carrier or diluent, wherein said active compound is selected from the group consisting of compounds of formula (I), defined above, and salts thereof.

The invention still further provides a method for the treatment or prophylaxis of insulin resistance, diabetes, hyperglycemia, arteriosclerosis, hyperlipemia, obesity, impaired glucose tolerance, hypertension, polycystic ovary syndrome, gestational diabetes mellitus or insulin resistant non-IGT, cataracts and complications thereof in a mammal, which may be human, which method comprises administering to said mammal an effective amount of an active compound, wherein said active compound is selected from the group consisting of compounds of formula (I), defined above, and salts thereof.

The invention also provides a pharmaceutical composition for the inhibition of aldose reductase, 5-lipoxygenase or lipid peroxide, and complications thereof, which composition comprises an effective amount of an active compound in admixture with a pharmaceutically acceptable carrier or diluent, wherein said active compound is selected from the group consisting of compounds of formula (I), defined above, and salts thereof.

The invention still further provides a method for the inhibition of aldose reductase, 5-lipoxygenase or lipid peroxide, and complications thereof in a mammal, which may be human, which method comprises administering to said mammal an effective amount of an active compound, wherein said active compound is selected from the group consisting of compounds of formula (I), defined above, and salts thereof.

The invention also provides processes for the preparation of the compounds of the present invention, which processes are described in more detail hereafter.

DETAILED DESCRIPTION OF INVENTION

Where X represents an unsubstituted benzimidazole group, this may be, for example, a 1-benzimidazolyl, 2-benzimidazolyl, 4-benzimidazolyl, 5-benzimidazolyl, 6-benzimidazolyl or 7-benzimidazolyl group. Alternatively, X may represent a substituted benzimidazole group, in which case, the substitutent is one or more of substituents α, defined above and exemplified below. There is no restriction on the number of substituents on the group other than that imposed by the number of substitutable positions, i.e. 5. Hence, the possible number of substituents is from 1 to 5. More preferably, in the case of those compounds intended for the treatment or prophylaxis of hyperglycemia, there are from 1 to 3 such substituents, one substituent being most preferred. In the case of those compounds intended for the inhibition of lipid peroxide, we most prefer those compounds having five substituents.

Where any of R, substituent α and/or substituent β represents an alkyl group, this may be a straight or branched chain alkyl group having from 1 to 4 carbon atoms. Examples of such alkyl groups include the methyl, ethyl, propyl, isopropyl, butyl, isobutyl, sec-butyl and t-butyl groups, of which we prefer the methyl group.

Where any of R, substituent α and/or substituent β represents an alkoxy group, this may be a straight or branched chain alkoxy group having from 1 to 4 carbon atoms. Examples of the such alkoxy groups include the methoxy, ethoxy, propoxy, isopropoxy, butoxy, isobutoxy, sec-butoxy and t-butoxy groups, of which we prefer the methoxy group.

Where any of R, substituent α and/or substituent β represents a halogen atom, this may be, for example, a bromine, chlorine or fluorine atom, of which the fluorine atom is preferred.

Where any of R, substituent α, $R^a$ and/or $R^b$ represents an aralkyl group, this may be as defined above, i.e. it is an alkyl group having from 1 to 5 carbon atoms which is substituted by at least one carbocyclic aryl group having from 6 to 10 ring carbon atoms. In the case of R, $R^a$ and $R^b$, the aryl group is preferably not substituted. In the case of substituents α, the group may be substituted or unsubstituted, although it is preferably unsubstituted. Although there may be from 1 to 3 aryl groups as substituents on the alkyl part, there is preferably only one such aryl group. The total number of carbon atoms in the alkyl part and the carbocyclic ring of the aryl part is preferably from 7 to 11. The alkyl part of the aralkyl group may be a straight or branched chain alkyl group having from 1 to 5 carbon atoms. Examples of such unsubstituted aralkyl groups include the benzyl, 2-phenylethyl, 1-phenylethyl, 3-phenylpropyl, 2-phenylpropyl, 1-phenylpropyl, 4-phenylbutyl, 1-phenylbutyl, 5-phenylpentyl, 1-naphthylmethyl and 2-naphthylmethyl groups, of which the benzyl group is preferred.

Where any of R, substituent α and/or substituent β represents a group of formula $—NR^aR^b$, this is an amino group which is unsubstituted or may optionally be substituted by any of the groups defined for $R^a$ and $R^b$ other than a hydrogen atom. Examples of such groups include:

(1) Alkyl groups which may be straight or branched chain groups having from 1 to 8 carbon atoms, for example the methyl, ethyl, propyl, isopropyl, butyl, isobutyl, sec-butyl, t-butyl, pentyl, 1-methylbutyl, 1-ethylpropyl, 2-methylbutyl, 3-methylbutyl, 1,1-dimethylpropyl, 1,2-dimethylpropyl, 2,2-dimethylpropyl, hexyl, 1-methylpentyl, 1-ethylbutyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1,1,2-trimethylpropyl, 1,2,2-trimethylpropyl, heptyl, 1-methylhexyl, 1-ethylpentyl, 1-propylbutyl, 3,3-dimethylpentyl, octyl, 1-methylheptyl, 2-ethylhexyl and 1,1,3,3-tetramethylbutyl groups, of which we prefer those straight or branched chain alkyl groups having from 1 to 6 carbon atoms, and most prefer those straight or branched chain alkyl groups having from 1 to 4 carbon atoms, particularly the methyl and ethyl groups.

(2) Aralkyl groups preferably having a total of from 7 to 11 carbon atoms in the alkyl group and the carbocyclic ring, which may be as defined and exemplified above in relation to substituents α.

(3) Aryl groups having from 6 to 10 carbon atoms, and preferably 6 or 10 carbon atoms, in a carbocyclic ring. Such a group may be substituted or unsubstituted and, if substituted, is preferably substituted by one or more of substituents β, defined above and exemplified below. It is, however, preferably unsubstituted. Examples of such aryl groups include the phenyl, 1-naphthyl and 2-naphthyl groups.

(4) Aliphatic acyl groups which may be straight or branched chain groups having from 1 to 11 carbon atoms, for example, the formyl, acetyl, propionyl, butyryl, isobutyryl, pivaloyl, valeryl, isovaleryl, hexanoyl, heptanoyl, octanoyl, nonanoyl, decanoyl and undecanoyl groups, of which we prefer the formyl, acetyl, propionyl, butyryl, isobutyryl, pivaloyl, valeryl and hexanoyl groups.

(5) Aryl-aliphatic acyl groups in which an aliphatic acyl group having from 2 to 6 carbon atoms is substituted by at least one carbocyclic aryl group having from 6 to 10 carbon atoms. The aryl group may be as defined and exemplified in (3) above. There may be from 1 to 3 such aryl substituents, preferably one. Examples of such aryl-aliphatic acyl groups include the phenylacetyl, 3-phenylpropionyl, 4-phenylbutyryl, 5-phenylpentanoyl, 6-phenylhexanoyl, α-methylphenylacetyl and α,α-dimethylphenylacetyl groups, of which the phenylacetyl group is preferred.

(6) Aromatic acyl groups having from 7 to 11 carbon atoms, in which the aromatic part is a carbocyclic aryl group which may be as defined and exemplified in (3) above, for example, the benzoyl, 1-naphthoyl and 2-naphthoyl groups, of which the benzoyl group is preferred.

The groups $R^a$ and $R^b$ may be the same or different. If they are the same and both represent hydrogen atoms, the group is a simple unsubstituted amino group. Alternatively, one may be a hydrogen atom and the other may be one of the other groups defined and exemplified above, or one may be one of the groups other than hydrogen defined and exemplified above and the other may be another of the groups other than hydrogen defined and exemplified above, or they may be the same and both may be one of the groups other than hydrogen defined and exemplified above. In general, we prefer that both should be hydrogen atoms or that one should be a hydrogen atom and the other should be one of the other groups defined and exemplified above.

Accordingly, where R, substituent α and/or substituent β represents an amino group, preferred examples of such amino groups include:

(1) amino groups having a single alkyl substituent, i.e. $R^a$ represents a hydrogen atom and $R^b$ represents an alkyl group, for example the methylamino, ethylamino, propylamino, isopropylamino, butylamino, isobutylamino, sec-butylamino, t-butylamino, pentylamino, 1-methylbutylamino, 1-ethypropylamino, 2-methylbutylamino, 3-methylbutylamino, 1,1-dimethylpropylamino, 1,2-dimethylpropylamino, 2,2-dimethylpropylamino, hexylamino, 1-methylpentylamino, 1-ethylbutylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1,1,2-trimethylpropylamino, 1,2,2-trimethylpropylamino, heptylamino, 1-methylhexylamino, 1-ethylpentylamino, 1-propylbutylamino, 3,3-dimethylpentylamino, octylamino, 1-methylheptylamino, 2-ethylhexylamino and 1,1,3,3-tetramethylbutylamino groups;

(2) amino groups having a single aralkyl substituent, i.e. $R^a$ represents a hydrogen atom and $R^b$ represents an aralkyl group, for example the benzylamino, 2-phenylethylamino, 1-phenylethylamino, 3-phenylpropylamino, 2-phenylpropylamino, 1-phenylpropylamino, 4-phenylbutylamino, 1-phenylbutylamino, 5-phenylpentylamino, 1-naphthylmethylamino and 2-naphthylmethylamino groups;

(3) amino groups having a single aryl substituent, i.e. $R^a$ represents a hydrogen atom and $R^b$ represents an aryl group, for example the phenylamino, 1-naphthylamino and 2-naphthylamino groups;

(4) amino groups having a single aliphatic acyl substituent, i.e. $R^a$ represents a hydrogen atom and $R^b$ represents an aliphatic acyl group, for example the formylamino, acetylamino, propionylamino, butyrylamino, isobutyrylamino, pivaloylamino, pentanoylamino, hexanoylamino, heptanoylamino, octanoylamino, nonanoylamino, decanoylamino and undecanoylamino groups;

(5) amino groups having a single aryl-aliphatic acyl substituent, i.e. $R^a$ represents a hydrogen atom and $R^b$ represents an aryl-aliphatic acyl group, for example the phenylacetylamino, 3-phenylpropionylamino, 4-phenylbutyrylamino, 5-phenylpentanoylamino, 6-phenylhexanoylamino, α-methylphenylacetylamino and α,α-dimethylphenylacetylamino groups;

(6) amino groups having a single aromatic acyl substituent, i.e. $R^a$ represents a hydrogen atom and $R^b$ represents an aromatic acyl group, for example the benzoylamino, 1-naphthoylamino and 2-naphthoylamino groups;

(7) amino groups having two alkyl substituents, i.e. $R^a$ and $R^b$ both represent alkyl groups which may be the same or different, for example the dimethylamino, diethylamino, N-methyl-N-ethylamino and N-methyl-N-pentylamino groups;

(8) amino groups having a single alkyl substituent and a single aralkyl substituent, i.e. $R^a$ represents an alkyl group and $R^b$ represents an aralkyl group, for example the N-ethyl-N-benzylamino, N-t-butyl-N-benzylamino and N-hexyl-N-benzylamino groups;

(9) amino groups having a single alkyl substituent and a single aryl substituent, i.e. $R^a$ represents an alkyl group and $R^b$ represents an aryl group, for example the N-methyl-N-phenylamino, N-ethyl-N-phenylamino and N-octyl-N-phenylamino groups;

(10) amino groups having a single alkyl substituent and a single aliphatic acyl substituent, i.e. $R^a$ represents an alkyl group and $R^b$ represents an aliphatic acyl group, for example the N-propyl-N-acetylamino, N-pentyl-N-propionylamino and N-ethyl-N-hexanoylamino groups;

(11) amino groups having a single alkyl substituent and a single aryl-aliphatic acyl substituent, i.e. $R^a$ represents an alkyl group and $R^b$ represents an aryl-aliphatic acyl group, for example the N-ethyl-N-phenylacetylamino, N-isopropyl-N-(2-phenylpropionyl)amino and N-methyl-N-(6-phenylhexanoyl)amino groups;

(12) amino groups having a single alkyl substituent and a single aromatic acyl substituent, i.e. $R^a$ represents an alkyl group and $R^b$ represents an aromatic acyl group, for example the N-methyl-N-benzoylamino, N-sec-butyl-N-benzoylamino and N-heptyl-N-benzoylamino groups;

(13) amino groups having two aralkyl substituents, i.e. $R^a$ and $R^b$ both represent aralkyl groups which may be the same or different, for example the dibenzylamino, N-benzyl-N-(3-phenylpropyl)amino and N-benzyl-N-(2-naphthylmethyl)amino groups;

(14) amino groups having a single aralkyl substituent and a single aryl substituent, i.e. $R^a$ represents an aralkyl group and $R^b$ represents an aryl group, for example the N-benzyl-N-phenylamino and N-(3-phenylpropyl)-N-phenylamino groups;

(15) amino groups having a single aralkyl substituent and a single aliphatic acyl substituent, i.e. $R^a$ represents an aralkyl group and $R^b$ represents an aliphatic acyl group, for example the N-benzyl-N-acetylamino, N-benzyl-N-propionylamino and N-benzyl-N-pentanoylamino groups;

(16) amino groups having a single aralkyl substituent and a single aryl-aliphatic acyl substituent, i.e. $R^a$ represents an aralkyl group and $R^b$ represents an aryl-aliphatic acyl group, for example the N-benzyl-N-phenylacetylamino and N-benzyl-N-(4-phenylbutyryl)amino groups;

(17) amino groups having a single aralkyl substituent and a single aromatic acyl substituent, i.e. $R^a$ represents an aralkyl group and $R^b$ represents an aromatic acyl group, for example the N-benzyl-N-benzoylamino and N-(2-phenylethyl)-N-benzoylamino groups;

(18) amino groups having two aryl substituents, i.e. $R^a$ and $R^b$ both represent aryl groups which may be the same or different, for example the diphenylamino, N-(1-naphthyl)-N-phenylamino and N-(2-naphthyl)-N-phenylamino groups;

(19) amino groups having a single aryl substituent and a single aliphatic acyl substituent, i.e. $R^a$ represents an aryl group and $R^b$ represents an aliphatic acyl group, for example the N-phenyl-N-acetylamino, N-phenyl-N-propionylamino and N-phenyl-N-hexanoylamino groups;

(20) amino groups having a single aryl substituent and a single aryl-aliphatic acyl substituent, i.e. $R^a$ represents an aryl group and $R^b$ represents an aryl-aliphatic acyl group, for example the N-phenyl-N-phenylacetylamino and N-phenyl-N-(4-phenylbutyryl)amino groups;

(21) amino groups having a single aryl substituent and a single aromatic acyl substituent, i.e. $R^a$ represents an aryl group and $R^b$ represents an aromatic acyl group, for example the N-phenyl-N-benzoylamino and N-phenyl-N-(2-naphthoyl)amino groups;

(22) amino groups having two aliphatic acyl substituents, i.e. $R^a$ and $R^b$ both represent aliphatic acyl groups which may be the same or different, for example the diacetylamino, N-acetyl-N-propionylamino and N-butyryl-N-hexanoylamino groups;

(23) amino groups having a single aliphatic acyl substituent and a single aryl-aliphatic acyl substituent, i.e. $R^a$ represents an aliphatic acyl group and $R^b$ represents an aryl-aliphatic acyl group, for example the N-acetyl-N-phenylacetylamino, N-acetyl-N-(4-phenylbutyryl) amino and N-butyryl-N-phenylacetylamino groups;

(24) amino groups having a single aliphatic acyl substituent and a single aromatic acyl substituent, i.e. $R^a$ represents an aliphatic acyl group and $R^b$ represents an aromatic acyl group, for example the N-acetyl-N-benzoylamino and N-butyryl-N-(2-naphthoyl)amino groups;

(25) amino groups having two aryl-aliphatic acyl substituents, i.e. $R^a$ and $R^b$ both represent aryl-aliphatic acyl groups which may be the same or different, for example the N,N-diphenylacetylamino, N-phenylacetyl-N-(2-phenypropionyl)amino and N-phenylacetyl-N-(4-phenylbutyryl)amino groups;

(26) amino groups having a single aryl-aliphatic acyl substituent and a single aromatic acyl substituent, i.e. $R^a$ represents an aryl-aliphatic acyl group and $R^b$ represents an aromatic acyl group, for example the N-phenylacetyl-N-benzoylamino and N-phenylacetyl-N-(2-naphthoyl)amino groups; and

(27) amino groups having two aromatic acyl substituents, i.e. $R^a$ and $R^b$ both represent aromatic acyl groups which may be the same or different, for example the dibenzoylamino and N-benzoyl-N-(2-naphthoyl)amino groups.

Where substituent α represents an alkylthio group, this may be a straight or branched chain alkylthio group having from 1 to 4 carbon atoms, for example the methylthio, ethylthio, propylthio, isopropylthio, butylthio, isobutylthio, sec-butylthio and t-butylthio groups.

Where substituent α represents an aryl group, this may be a carbocyclic aryl group having from 6 to 10 carbon atoms which is unsubstituted or is substituted by one or more of substituents β. Examples of the unsubstituted aryl groups include the phenyl, 1-naphthyl and 2-naphthyl groups. Where the aryl group is substituted, there is no restriction on the number of substituents, except such as may be imposed by the number of substitutable positions and possibly by steric constraints; thus the maximum number of substituents on a phenyl group is 5, whilst that on a naphthyl group is 7. In general, however, from 1 to 3 substituents are preferred, one substituent generally being more preferred.

Moreover, where substituent β represents an alkyl group having from 1 to 4 carbon atoms, an alkoxy group having from 1 to 4 carbon atoms, a halogen atom or a group of formula —$NR^aR^b$, these may be as defined and exemplified above in relation to the corresponding group or atom represented by substituent α. Alternatively, substituent β may be a hydroxy group, a nitro group, a phenyl group or a trifluoromethyl group.

Examples of substituted aryl groups which may be represented by substituent α include:

(1) Aryl groups substituted by at least one straight or branched chain alkyl group having from 1 to 4 carbon atoms, for example, the 4-methylphenyl, 4-ethylphenyl, 4-propylphenyl, 4-isopropylphenyl, 4-butylphenyl, 4-isobutylphenyl, 4-sec-butylphenyl, 4-t-butylphenyl, 4-methyl-1-naphthyl, 5-ethyl-1-naphthyl, 8-propyl-1-naphthyl, 4-isopropyl-1-naphthyl, 5-butyl-1-naphthyl, 4-isobutyl-1-naphthyl, 4-sec-butyl-1-naphthyl, 4-t-butyl-1-naphthyl, 4-methyl-2-naphthyl, 5-ethyl-2-naphthyl, 8-propyl-2-naphthyl, 4-isopropyl-2-naphthyl, 5-butyl-2-naphthyl, 8-isobutyl-2-naphthyl, 4-sec-butyl-2-naphthyl and 5-t-butyl-2-naphthyl groups.

(2) Aryl groups substituted by at least one straight or branched chain alkoxy group having from 1 to 4 carbon atoms, for example, the 4-methoxyphenyl, 4-ethoxyphenyl, 4-propoxyphenyl, 4-isopropoxyphenyl, 4-butoxyphenyl, 4-isobutoxyphenyl, 4-sec-butoxyphenyl, 4-t-butoxyphenyl, 4-methoxy-1-naphthyl, 5-ethoxy-1-naphthyl, 8-propoxy-1-naphthyl, 4-isopropoxy-1-naphthyl, 5-butoxy-1-naphthyl, 4-isobutoxy-1-naphthyl, 4-sec-butoxy-1-naphthyl, 4-t-butoxy-1-naphthyl, 4-methoxy-2-naphthyl, 5-ethoxy-2-naphthyl, 8-propoxy-2-naphthyl, 4-isopropoxy-2-naphthyl, 5-butoxy-2-naphthyl, 8-isobutoxy-2-naphthyl, 4-sec-butoxy-2-naphthyl and 5-t-butoxy-2-naphthyl groups.

(3) Aryl groups substituted by at least one halogen atom, for example, the 4-bromophenyl, 4-chlorophenyl, 4-fluorophenyl, 4-iodophenyl, 3-chlorophenyl, 3-fluorophenyl, 3-bromophenyl, 3-iodophenyl, 4-bromo-1-naphthyl, 4-chloro-1-naphthyl, 4-fluoro-1-naphthyl, 4-iodo-1-naphthyl, 5-chloro-1-naphthyl, 5-fluoro-1-naphthyl, 5-bromo-1-naphthyl, 8-chloro-1-naphthyl, 4-fluoro-2-naphthyl, 4-bromo-2-naphthyl, 4-chloro-2-naphthyl, 4-iodo-2-naphthyl, 5-bromo-2-naphthyl, 5-chloro-2-naphthyl, 5-fluoro-2-naphthyl and 5-iodo-2-naphthyl groups.

(4) Aryl groups substituted by at least one hydroxy group, for example, the 2-hydroxyphenyl, 3-hydroxyphenyl, 4-hydroxyphenyl, 4-hydroxy-1-naphthyl, 5-hydroxy-1-naphthyl, 8-hydroxy-1-naphthyl, 4-hydroxy-2-naphthyl, 5-hydroxy-2-naphthyl and 8-hydroxy-2-naphthyl groups.

(5) Aryl groups substituted by at least one nitro group, for example, the 2-nitrophenyl, 3-nitrophenyl, 4-nitrophenyl, 4-nitro-1-naphthyl, 5-nitro-1-naphthyl, 8-nitro-1-naphthyl, 4-nitro-2-naphthyl, 5-nitro-2-naphthyl and 8-nitro-2-naphthyl groups.

(6) Aryl groups substituted by at least one phenyl group, for example, the 3-phenylphenyl, 4-phenylphenyl, 4-phenyl-1-naphthyl, 5-phenyl-1-naphthyl, 8-phenyl-1-naphthyl, 4-phenyl-2-naphthyl, 5-phenyl-2-naphthyl and 8-phenyl-2-naphthyl groups.

(7) Aryl groups substituted by at least one trifluoromethyl group, for example, the 3-trifluoromethylphenyl, 4-trifluoromethylphenyl, 4-trifluoromethyl-1-naphthyl, 5-trifluoromethyl-1-naphthyl, 8-trifluoromethyl-1-naphthyl, 4-trifluoromethyl-2-naphthyl, 5-trifluoromethyl-2-naphthyl and 8-trifluoromethyl-2-naphthyl groups.

(8) Aryl groups substituted by at least one unsubstituted amino group, for example, the 2-aminophenyl, 3-aminophenyl, 4-aminophenyl, 4-amino-1-naphthyl and 8-amino-2-naphthyl.

(9) Aryl groups substituted by at least one substituted amino group, examples of which include:
(i) aryl groups substituted by a group of formula —$NR^aR^b$, where $R^a$ represents a hydrogen atom and $R^b$ represents an alkyl group, for example, the 3-methylaminophenyl, 4-ethylaminophenyl, 3-propylaminophenyl, 3-isopropylaminophenyl, 4-butylaminophenyl and 3-isobutylaminophenyl groups;

(ii) aryl groups substituted by a group of formula —NR$^a$R$^b$, where R$^a$ represents a hydrogen atom and R$^b$ represents an aralkyl group, for example, the 4-benzylaminophenyl, 4-(2-phenylethylamino)phenyl, 4-(1-phenylethylamino)phenyl, 4-(4-phenylbutylamino)phenyl and 4-(1-naphthylmethylamino)phenyl groups;

(iii) aryl groups substituted by a group of formula —NR$^a$R$^b$, where R$^a$ represents a hydrogen atom and R$^b$ represents an aryl group, for example, the 4-phenylaminophenyl and 4-(1-naphthylamino)phenyl groups;

(iv) aryl groups substituted by a group of formula —NR$^a$R$^b$, where R$^a$ represents a hydrogen atom and R$^b$ represents an aliphatic acyl group, for example, the 4-formylaminophenyl, 4-acetylaminophenyl, 4-butyrylaminophenyl, 4-pivaloylaminophenyl, 4-hexanoylaminophenyl, 4-octanoylaminophenyl and 4-undecanoylaminophenyl groups;

(v) aryl groups substituted by a group of formula —NR$^a$R$^b$, where R$^a$ represents a hydrogen atom and R$^b$ represents an aryl-aliphatic acyl group, for example, the 4-phenylacetylaminophenyl, 4-(4-phenylbutyrylamino)phenyl, 4-(6-phenylhexanoylamino)phenyl, 4-(α-methylphenylacetylamino)phenyl and 4-(α,α-dimethylphenylacetylamino)phenyl groups;

(vi) aryl groups substituted by a group of formula —NR$^a$R$^b$, where R$^a$ represents a hydrogen atom and R$^b$ represents an aromatic acyl group, for example, the 4-benzoylaminophenyl, 4-(1-naphthoylamino)phenyl and 4-(2-naphthoylamino)phenyl groups;

(vii) aryl groups substituted by a group of formula —NR$^a$R$^b$, where R$^a$ and R$^b$ both represent alkyl groups which may be the same or different, for example, the 4-dimethylaminophenyl, 4-diethylaminophenyl and 4-(N-methyl-N-ethylamino)phenyl groups;

(viii) aryl groups substituted by a group of formula —NR$^a$R$^b$, where R$^a$ represents an alkyl group and R$^b$ represents an aralkyl group, for example, the 4-(N-ethyl-N-benzylamino)phenyl, 4-(N-t-butyl-N-benzylamino)phenyl and 4-(N-hexyl-N-benzylamino)phenyl groups;

(ix) aryl groups substituted by a group of formula —NR$^a$R$^b$, where R$^a$ represents an alkyl group and R$^b$ represents an aryl group, for example, the 4-(N-methyl-N-phenylamino)phenyl and 4-(N-octyl-N-phenylamino)phenyl groups;

(x) aryl groups substituted by a group of formula —NR$^a$R$^b$, where R$^a$ represents an alkyl group and R$^b$ represents an aliphatic acyl group, for example, the 4-(N-propyl-N-acetylamino)phenyl and 4-(N-ethyl-N-hexanoylamino)phenyl groups;

(xi) aryl groups substituted by a group of formula —NR$^a$R$^b$, where R$^a$ represents an alkyl group and R$^b$ represents an aryl-aliphatic acyl group, for example, the 4-(N-ethyl-N-phenylacetylamino)phenyl and 4-[N-methyl-N-(6-phenylhexanoyl)amino]phenyl groups;

(xii) aryl groups substituted by a group of formula —NR$^a$R$^b$, where R$^a$ represents an alkyl group and R$^b$ represents an aromatic acyl group, for example, the 4-(N-methyl-N-benzoylamino)phenyl and 4-(N-heptyl-N-benzoylamino)phenyl groups;

(xiii) aryl groups substituted by a group of formula —NR$^a$R$^b$, where R$^a$ and R$^b$ both represent aralkyl groups which may be the same or different, for example, the 4-dibenzylaminophenyl and 4-[N-benzyl-N-(2-naphthylmethyl)amino]phenyl groups;

(xiv) aryl groups substituted by a group of formula —NR$^a$R$^b$, where R$^a$ represents an aralkyl group and R$^b$ represents an aryl group, for example, the 4-(N-benzyl-N-phenylamino)phenyl and 4-[N-(3-phenylpropyl)-N-phenylamino]phenyl groups;

(xv) aryl groups substituted by a group of formula —NR$^a$R$^b$, where R$^a$ represents an aralkyl group and R$^b$ represents an aliphatic acyl group, for example, the 4-(N-benzyl-N-acetylamino)phenyl and 4-(N-benzyl-N-pentanoylamino)phenyl groups;

(xvi) aryl groups substituted by a group of formula —NR$^a$R$^b$, where R$^a$ represents an aralkyl group and R$^b$ represents an aryl-aliphatic acyl group, for example, the 4-(N-benzyl-N-phenylacetylamino)phenyl and 4-[N-benzyl-N-(4-phenylbutyryl)amino]phenyl groups;

(xvii) aryl groups substituted by a group of formula —NR$^a$R$^b$, where R$^a$ represents an aralkyl group and R$^b$ represents an aromatic acyl group, for example, the 4-(N-benzyl-N-benzoylamino)phenyl and 4-[N-(2-phenylethyl)-N-benzoylamino]phenyl groups;

(xviii) aryl groups substituted by a group of formula —NR$^a$R$^b$, where R$^a$ and R$^b$ both represent aryl groups which may be the same or different, for example, the 4-(diphenylamino)phenyl and 4-[N-(2-naphthyl)-N-phenylamino)phenyl groups;

(xix) aryl groups substituted by a group of formula —NR$^a$R$^b$, where R$^a$ represents an aryl group and R$^b$ represents an aliphatic acyl group, for example, the 4-(N-phenyl-N-acetylamino)phenyl and 4-(N-phenyl-N-hexanoylamino)phenyl groups;

(xx) aryl groups substituted by a group of formula —NR$^a$R$^b$, where R$^a$ represents an aryl group and R$^b$ represents an aryl-aliphatic acyl group, for example, the 4-(N-phenyl-N-phenylacetylamino)phenyl and 4-[N-phenyl-N-(4-phenylbutyryl)amino]phenyl groups;

(xxi) aryl groups substituted by a group of formula —NR$^a$R$^b$, where R$^a$ represents an aryl group and R$^b$ represents an aromatic acyl group, for example, the 4-(N-phenyl-N-benzoylamino)phenyl group;

(xxii) aryl groups substituted by a group of formula —NR$^a$R$^b$, where R$^a$ and R$^b$ both represent aliphatic acyl groups which may be the same or different, for example, the 4-diacetylaminophenyl and 4-(N-butyryl-N-hexanoylamino)phenyl groups;

(xxiii) aryl groups substituted by a group of formula —NR$^a$R$^b$, where R$^a$ represents an aliphatic acyl group and R$^b$ represents an aryl-aliphatic acyl group, for example, the 4-(N-acetyl-N-phenylacetylamino)phenyl and 4-(N-butyryl-N-phenylacetylamino)phenyl groups;

(xxiv) aryl groups substituted by a group of formula —NR$^a$R$^b$, where R$^a$ represents an aliphatic acyl group and R$^b$ represents an aromatic acyl group, for example, the 4-(N-acetyl-N-benzoylamino)phenyl and 4-[N-butyryl-N-(2-naphthoyl)amino]phenyl groups;

(xxv) aryl groups substituted by a group of formula —NR$^a$R$^b$, where R$^a$ and R$^b$ both represent aryl-aliphatic acyl groups which may be the same or different, for example, the 4-(N,N-diphenylacetylamino)phenyl and 4-[N-phenylacetyl-N-(4-phenylbutyryl)amino]phenyl groups;

(xxvi) aryl groups substituted by a group of formula —NR$^a$R$^b$, where R$^a$ represents an aryl-aliphatic acyl group and R$^b$ represents an aromatic acyl group, for example, the 4-(N-phenylacetyl-N-benzoylamino) phenyl and 4-[N-phenylacetyl-N-(2-naphthoyl) amino]phenyl groups; and (xxvii) aryl groups substituted by a group of formula —NR$^a$R$^b$, where R$^a$ and R$^b$ both represent aromatic acyl groups which may be the same or different, for example, the 4-dibenzoylaminophenyl and 4-[N-benzoyl-N-(2-naphthoyl)amino]phenyl groups.

Where substituent α represents an aralkyl group, this is an alkyl group having from 1 to 5 carbon atoms which is substituted by a carbocyclic aryl group having from 6 to 10 carbon atoms in a carbocyclic ring. The aryl group may itself be substituted or unsubstituted and, if it is substituted, the substituents are selected from substituents β, defined and exemplified above. Preferably the aralkyl group has a total of from 7 to 11 carbon atoms. The alkyl part of the aralkyl group may be a straight or branched chain alkyl group having from 1 to 5 carbon atoms. Examples of the unsubstituted aralkyl groups include the benzyl, 2-phenylethyl, 1-phenylethyl, 3-phenylpropyl, 2-phenylpropyl, 1-phenylpropyl, 4-phenylbutyl, 1-phenylbutyl, 5-phenylpentyl, 1-naphthylmethyl and 2-naphthylmethyl groups. Where the aryl part of the aralkyl group is substituted, there is no restriction on the number of substituents, except such as may be imposed by the number of substitutable positions and possibly by steric constraints; thus the maximum number of substituents on a phenyl group is 5, whilst that on a naphthyl group is 7. In general, however, from 1 to 3 substituents are preferred, one substituent generally being more preferred.

Moreover, where substituent β represents an alkyl group having from 1 to 4 carbon atoms, an alkoxy group having from 1 to 4 carbon atoms, a halogen atom or a group of formula —NR$^a$R$^b$, these may be as defined and exemplified above in relation to the corresponding group or atom represented by substituent α. Alternatively, substituent β may be a hydroxy group, a nitro group, a phenyl group or a trifluoromethyl group.

Examples of substituted aralkyl groups which may be represented by substituent α include:

(1) Aralkyl groups substituted by at least one straight or branched chain alkyl group having from 1 to 4 carbon atoms, for example, the 4-methylbenzyl, 4-ethylbenzyl, 4-propylbenzyl, 4-isopropylbenzyl, 4-butylbenzyl, 4-isobutylbenzyl, 4-sec-butylbenzyl, 4-t-butylbenzyl, 4-methyl-1-naphthylmethyl, 5-ethyl-1-naphthylmethyl, 8-propyl-1-naphthylmethyl, 4-isopropyl-1-naphthylmethyl, 5-butyl-1-napthylmethyl, 4-isobutyl-1-naphthylmethyl, 4-sec-butyl-1-naphthylmethyl, 4-t-butyl-1-naphthylmethyl, 4-methyl-2-naphthylmethyl, 5-ethyl-2-naphthylmethyl, 8-propyl-2-naphthylmethyl, 4-isopropyl-2-naphthylmethyl, 5-butyl-2-naphthylmethyl, 8-isobutyl-2-naphthylmethyl, 4-sec-butyl-2-naphthylmethyl and 5-t-butyl-2-naphthylmethyl groups.

(2) Aralkyl groups substituted by at least one straight or branched chain alkoxy group having from 1 to 4 carbon atoms, for example, the 4-methoxybenzyl, 4-ethoxybenzyl, 4-propoxybenzyl, 4-isopropoxybenzyl, 4-butoxybenzyl, 4-isobutoxybenzyl, 4-sec-butoxybenzyl, 4-t-butoxybenzyl, 4-methoxy-1-naphthylmethyl, 5-ethoxy-1-naphthylmethyl, 8-propoxy-1-naphthylmethyl, 4-isopropoxy-1-naphthylmethyl, 5-butoxy-1-naphthylmethyl, 4-isobutoxy-1-naphthylmethyl, 4-sec-butoxy-1-naphthylmethyl, 4-t-butoxy-1-naphthylmethyl, 4-methoxy-2-naphthylmethyl, 5-ethoxy-2-naphthylmethyl, 8-propoxy-2-naphthylmethyl, 4-isopropoxy-2-naphthylmethyl, 5-butoxy-2-naphthylmethyl, 8-isobutoxy-2-naphthylmethyl, 4-sec-butoxy-2-naphthylmethyl and 5-t-butoxy-2-naphthylmethyl groups.

(3) Aralkyl groups substituted by at least one halogen atom, for example, the 4-bromobenzyl, 4-chlorobenzyl, 4-fluorobenzyl, 4-iodobenzyl, 3-chlorobenzyl, 3-fluorobenzyl, 3-bromobenzyl, 3-iodobenzyl, 4-bromo-1-naphthylmethyl, 4-chloro-1-naphthylmethyl, 4-fluoro-1-naphthylmethyl, 4-iodo-1-naphthylmethyl, 5-chloro-1-naphthylmethyl, 5-fluoro-1-naphthylmethyl, 5-bromo-1-naphthylmethyl, 8-chloro-1-naphthylmethyl, 4-fluoro-2-naphthylmethyl, 4-bromo-2-naphthylmethyl, 4-chloro-2-naphthylmethyl, 4-iodo-2-naphthylmethyl, 5-bromo-2-naphthylmethyl, 5-chloro-2-naphthylmethyl, 5-fluoro-2-naphthylmethyl and 5-iodo-2-naphthylmethyl groups.

(4) Aralkyl groups substituted by at least one hydroxy group, for example, the 2-hydroxybenzyl, 3-hydroxybenzyl, 4-hydroxybenzyl, 4-hydroxy-1-naphthylmethyl, 5-hydroxy-1-naphthylmethyl, 8-hydroxy-1-naphthylmethyl, 4-hydroxy-2-naphthylmethyl, 5-hydroxy-2-naphthylmethyl and 8-hydroxy-2-naphthylmethyl groups.

(5) Aralkyl groups substituted by at least one nitro group, for example, the 2-nitrobenzyl, 3-nitrobenzyl, 4-nitrobenzyl, 4-nitro-1-naphthylmethyl, 5-nitro-1-naphthylmethyl, 8-nitro-1-naphthylmethyl, 4-nitro-2-naphthylmethyl, 5-nitro-2-naphthylmethyl and 8-nitro-2-naphthylmethyl groups.

(6) Aralkyl groups substituted by at least one phenyl group, for example, the 3-phenylbenzyl, 4-phenylbenzyl, 4-phenyl-1-naphthylmethyl, 5-phenyl-1-naphthylmethyl, 8-phenyl-1-naphthylmethyl, 4-phenyl-2-naphthylmethyl, 5-phenyl-2-naphthylmethyl and 8-phenyl-2-naphthylmethyl groups.

(7) Aralkyl groups substituted by at least one trifluoromethyl group, for example, the 3-trifluoromethylbenzyl, 4-trifluoromethylbenzyl, 4-trifluoromethyl-1-naphthylmethyl, 5-trifluoromethyl-1-naphthylmethyl, 8-trifluoromethyl-1-naphthylmethyl, 4-trifluoromethyl-2-naphthylmethyl, 5-trifluoromethyl-2-naphthylmethyl and 8-trifluoromethyl-2-naphthylmethyl groups.

(8) Aralkyl groups substituted by at least one unsubstituted amino group, for example, the 2-aminobenzyl, 3-aminobenzyl, 4-aminobenzyl, 4-amino-1-naphthylmethyl and 8-amino-2-naphthylmethyl groups.

(9) Aralkyl groups substituted by at least one substituted amino group, examples of which include:
(i) aralkyl groups substituted by a group of formula —NR$^a$R$^b$, where R$^a$ represents a hydrogen atom and R$^b$ represents an alkyl group, for example, the 3-methylaminobenzyl, 4-ethylaminobenzyl, 3-propylaminobenzyl, 3-isopropylaminobenzyl, 4-butylaminobenzyl and 3-isobutylaminobenzyl groups;

(ii) aralkyl groups substituted by a group of formula —NR$^a$R$^b$, where R$^a$ represents a hydrogen atom and R$^b$ represents an aralkyl group, for example, the 4-benzylaminobenzyl, 4-(2-phenylethylamino) benzyl, 4-(1-phenylethylamino)benzyl, 4-(4-phenylbutylamino)benzyl and 4-(1-naphthylmethylamino)benzyl groups;

(iii) aralkyl groups substituted by a group of formula —NR$^a$R$^b$, where R$^a$ represents a hydrogen atom and R$^b$ represents an aryl group, for example, the 4-phenylaminobenzyl and 4-(1-naphthylamino) benzyl groups;

(iv) aralkyl groups substituted by a group of formula —NR$^a$R$^b$, where R$^a$ represents a hydrogen atom and R$^b$ represents an aliphatic acyl group, for example, the 4-formylaminobenzyl, 4-acetylaminobenzyl, 4-butyrylaminobenzyl, 4-pivaloylaminobenzyl, 4-hexanoylaminobenzyl, 4-octanoylaminobenzyl and 4-undecanoylaminobenzyl groups;

(v) aralkyl groups substituted by a group of formula —NR$^a$R$^b$, where R$^a$ represents a hydrogen atom and R$^b$ represents an aryl-aliphatic acyl group, for example, the 4-phenylacetylaminobenzyl, 4-(4-phenylbutyrylamino)benzyl, 4-(6-phenylhexanoylamino)benzyl, 4-(α-methylphenylacetylamino)benzyl and 4-(α,α-dimethylphenylacetylamino)benzyl groups;

(vi) aralkyl groups substituted by a group of formula —NR$^a$R$^b$, where R$^a$ represents a hydrogen atom and R$^b$ represents an aromatic acyl group, for example, the 4-benzoylaminobenzyl, 4-(1-naphthoylamino) benzyl and 4-(2-naphthoylamino)benzyl groups;

(vii) aralkyl groups substituted by a group of formula —NR$^a$R$^b$, where R$^a$ and R$^b$ both represent alkyl groups which may be the same or different, for example, the 4-dimethylaminobenzyl, 4-diethylaminobenzyl and 4-(N-methyl-N-ethylamino)benzyl groups;

(viii) aralkyl groups substituted by a group of formula —NR$^a$R$^b$, where R$^a$ represents an alkyl group and R$^b$ represents an aralkyl group, for example, the 4-(N-ethyl-N-benzylamino)benzyl, 4-(N-t-butyl-N-benzylamino)benzyl and 4-(N-hexyl-N-benzylamino)benzyl groups;

(ix) aralkyl groups substituted by a group of formula —NR$^a$R$^b$, where R$^a$ represents an alkyl group and R$^b$ represents an aryl group, for example, the 4-(N-methyl-N-phenylamino)benzyl and 4-(N-octyl-N-phenylamino)benzyl groups;

(x) aralkyl groups substituted by a group of formula —NR$^a$R$^b$, where R$^a$ represents an alkyl group and R$^b$ represents an aliphatic acyl group, for example, the 4-(N-propyl-N-acetylamino)benzyl and 4-(N-ethyl-N-hexanoylamino)benzyl groups;

(xi) aralkyl groups substituted by a group of formula —NR$^a$R$^b$, where R$^a$ represents an alkyl group and R$^b$ represents an aryl-aliphatic acyl group, for example, the 4-(N-ethyl-N-phenylacetylamino) benzyl and 4-[N-methyl-N-(6-phenylhexanoyl) amino]benzyl groups;

(xii) aralkyl groups substituted by a group of formula —NR$^a$R$^b$, where R$^a$ represents an alkyl group and R$^b$ represents an aromatic acyl group, for example, the 4-(N-methyl-N-benzoylamino)benzyl and 4-(N-heptyl-N-benzoylamino)benzyl groups;

(xiii) aralkyl groups substituted by a group of formula —NR$^a$R$^b$, where R$^a$ and R$^b$ both represent aralkyl groups which may be the same or different, for example, the 4-dibenzylaminobenzyl and 4-[N-benzyl-N-(2-naphthylmethyl)amino]benzyl groups;

(xiv) aralkyl groups substituted by a group of formula —NR$^a$R$^b$, where R$^a$ represents an aralkyl group and R$^b$ represents an aryl group, for example, the 4-(N-benzyl-N-phenylamino)benzyl and 4-[N-(3-phenylpropyl)-N-phenylamino]benzyl groups;

(xv) aralkyl groups substituted by a group of formula —NR$^a$R$^b$, where R$^a$ represents an aralkyl group and R$^b$ represents an aliphatic acyl group, for example, the 4-(N-benzyl-N-acetylamino)benzyl and 4-(N-benzyl-N-pentanoylamino)benzyl groups;

(xvi) aralkyl groups substituted by a group of formula —NR$^a$R$^b$, where R$^a$ represents an aralkyl group and R$^b$ represents an aryl-aliphatic acyl group, for example, the 4-(N-benzyl-N-phenylacetylamino) benzyl and 4-[N-benzyl-N-(4-phenylbutyryl)amino] benzyl groups;

(xvii) aralkyl groups substituted by a group of formula —NR$^a$R$^b$, where R$^a$ represents an aralkyl group and R$^b$ represents an aromatic acyl group, for example, the 4-(N-benzyl-N-benzoylamino)benzyl and 4-[N-(2-phenylethyl)-N-benzoylamino]benyl groups;

(xviii) aralkyl groups substituted by a group of formula —NR$^a$R$^b$, where R$^a$ and R$^b$ both represent aryl groups which may be the same or different, for example, the 4-diphenylaminobenzyl and 4-[N-(2-naphthyl)-N-phenylamino]benzyl groups;

(xix) aralkyl groups substituted by a group of formula —NR$^a$R$^b$, where R$^a$ represents an aryl group and R$^b$ represents an aliphatic acyl group, for example, the 4-(N-phenyl-N-acetylamino)benzyl and 4-(N-phenyl-N-hexanoylamino)benzyl groups;

(xx) aralkyl groups substituted by a group of formula —NR$^a$R$^b$, where R$^a$ represents an aryl group and R$^b$ represents an aryl-aliphatic acyl group, for example, the 4-(N-phenyl-N-phenylacetylamino)benzyl and 4-[N-phenyl-N-(4-phenylbutyryl)amino]benzyl groups;

(xxi) aralkyl groups substituted by a group of formula —NR$^a$R$^b$, where R$^a$ represents an aryl group and R$^b$ represents an aromatic acyl group, for example, the 4-(N-phenyl-N-benzoylamino)benzyl group;

(xxii) aralkyl groups substituted by a group of formula —NR$^a$R$^b$, where R$^a$ and R$^b$ both represent aliphatic acyl groups which may be the same or different, for example, the 4-diacetylaminobenzyl and 4-(N-butryl-N-hexanoylamino)benzyl groups;

(xxiii) aralkyl groups substituted by a group of formula —NR$^a$R$^b$, where R$^a$ represents an aliphatic acyl group and R$^b$ represents an aryl-aliphatic acyl group, for example, the 4-(N-acetyl-N-phenylacetylamino) benzyl and 4-(N-butyryl-N-phenylacetylamino) benzyl groups;

(xxiv) aralkyl groups substituted by a group of formula —NR$^a$R$^b$, where R$^a$ represents an aliphatic acyl group and R$^b$ represents an aromatic acyl group, for example, the 4-(N-acetyl-N-benzoylamino)benzyl and 4-[N-butyryl-N-(2-naphthoyl)amino]benzyl groups;

(xxv) aralkyl groups substituted by a group of formula —NR$^a$R$^b$, where R$^a$ and R$^b$ both represent aryl-aliphatic acyl groups which may be the same or different, for example, the 4-(N,N-diphenylacetylamino)benzyl and 4-[N-phenylacetyl-N-(4-phenylbutyryl)amino]benzyl groups;

(xxvi) aralkyl groups substituted by a group of formula —NR$^a$R$^b$, where R$^a$ represents an aryl-aliphatic acyl group and R$^b$ represents an aromatic acyl group, for example, the 4-(N-phenylacetyl-N-benzoylamino) benzyl and 4-[N-phenylacetyl-N-(2-naphthoyl) amino]benzyl groups; and (xxvii) aralkyl groups substituted by a group of formula —NR$^a$R$^b$, where R$^a$ and R$^b$ both represent aromatic acyl groups which may be the same or different, for example, the 4-dibenzoylaminobenzyl and 4-[N-benzoyl-N-(2-naphthoyl)amino]benzyl groups.

Where the benzimidazole group represented by X has a substituent α at the 1- and/or 2-position, the substituent α is preferably:

a straight or branched chain alkyl group having from 1 to 4 carbon atoms, an aryl group having from 6 to 10 carbon atoms which may optionally be substituted by one or more substituents β, or a straight or branched chain aralkyl group having from 7 to 11 carbon atoms which may optionally be substituted by one or more substituents β.

Examples of such benzimidazole groups having from 1 to 5 of substituents α include, for example, the 1-methylbenzimidazol-2-yl, 1-ethylbenzimidazol-2-yl, 1-propylbenzimidazol-2-yl, 1-isopropylbenzimidazol-2-yl, 1-butylbenzimidazol-2-yl, 6-methoxy-1H-benzimidazol-2-yl, 5-methoxy-1H-benzimidazol-2-yl, 6-methoxy-1-methylbenzimidazol-2-yl, 5-methoxy-1-methylbenzimidazol-2-yl, 1-ethyl-6-methoxybenzimidaol-2-yl, 1-ethyl-5-methoxybenzimidazol-2-yl, 6-methoxy-1-propylbenzimidazol-2-yl, 5-methoxy-1-propylbenzimidazol-2-yl, 1-isopropyl-6-methoxybenzimidazol-2-yl, 1-isopropyl-5-methoxybenzimidazol-2-yl, 1-isobutyl-6-methoxybenzimidazol-2-yl, 1-isobutyl-5-methoxybenzimidazol-2-yl, 6-ethoxy-1-methylbenzimidazol-2-yl, 5-ethoxy-1-methylbenzimidazol-2-yl, 1-methyl-6-propoxybenzimidazol-2-yl, 1-methyl-5-propoxybenzimidazol-2-yl, 6-isopropoxy-1-methylbenzimidazol-2-yl, 5-isopropoxy-1-methylbenzimidazol-2-yl, 6-butoxy-1-methylbenzimidazol-2-yl, 5-butoxy-1-methylbenzimidazol-2-yl, 6-isobutoxy-1-methylbenzimidazol-2-yl, 5-isobutoxy-1-methylbenzimidazol-2-yl, 6-sec-butoxy-1-methylbenzimidazol-2-yl, 5-sec-butoxy-1-methylbenzimidazol-2-yl, 6-t-butoxy-1-methylbenzimidazol-2-yl, 5-t-butoxy-1-methylbenzimidazol-2-yl, 6-butoxy-1-propylbenzimidazol-2-yl, 5-butoxy-1-propylbenzimidazol-2-yl, 6-benzyloxy-1-methylbenzimidazol-2-yl, 5-benzyloxy-1-methylbenzimidazol-2-yl, 5-methoxy-1,6-dimethylbenzimidazol-2-yl, 6-methoxy-1,5-dimethylbenzimidazol-2-yl, 6-bromo-5-methoxy-1-methylbenzimidazol- 2-yl, 5-bromo-6-methoxy-1-methylbenzimidazol-2-yl, 5-ethoxy-6-fluoro-1-methylbenzimidazol-2-yl, 6-ethoxy-5-fluoro-1-methylbenzimidazol-2-yl, 5,7-difluoro-1-methylbenzimidazol-2-yl, 4,6-difluoro-1-methylbenzimidazol-2-yl, 6-fluoro-1-methylbenzimidazol-2-yl, 5-fluoro-1-methylbenzimidazol-2-yl, 5-chloro-1,6-dimethylbenzimidazol-2-yl, 6-chloro-1,5-dimethylbenzimidazol-2-yl, 5-chloro-1,6-diethylbenzimidazol-2-yl, 6-chloro-1,5-diethylbenzimidazol-2-yl, 5-ethyl-1-methylbenzimidazol-2-yl, 6-ethyl-1-methylbenzimidazol-2-yl, 5-bromo-1-methylbenzimidazol-2-yl, 6-bromo-1-methylbenzimidazol-2-yl, 7-bromo-1-methyl-5-trifluoromethylbenzimidazol-2-yl, 4-bromo-1-methyl-6-trifluoromethylbenzimidazol-2-yl, 7-chloro-1-methyl-5-trifluoromethylbenzimidazol-2-yl, 4-chloro-1-methyl-6-trifluoromethylbenzimidazol-2-yl, 1-methyl-7-trifluoromethylbenzimidazol-2-yl, 1-methyl-4-trifluoromethylbenzimidazol-2-yl, 1-methyl-5-trifluoromethylbenzimidazol-2-yl, 1-methyl-6-trifluoromethylbenzimidazol-2-yl, 5-bromo-1,6,7-trimethylbenzimidazol-2-yl, 6-bromo-1,4,5-trimethylbenzimidazol-2-yl, 5-fluoro-6-chloro-1-methylbenzimidazol-2-yl, 6-fluoro-5-chloro-1-methylbenzimidazol-2-yl, 5-bromo-1,7-dimethylbenzimidazol-2-yl, 6-bromo-1,4-dimethylbenzimidazol-2-yl, 6-t-butyl-1-methylbenzimidazol-2-yl, 5-t-butyl-1-methylbenzimidazol-2-yl, 6-hydroxy-1-methylbenzimidazol-2-yl, 5-hydroxy-1-methylbenzimidazol-2-yl, 1,7-dimethylbenzimidazol-2-yl, 1,4-dimethylbenzimidazol-2-yl, 6,7-dichloro-1-methylbenzimidazol-2-yl, 4,5-dichloro-1-methylbenzimidazol-2-yl, 5,6,7-trifluoro-1-methylbenzimidazol-2-yl, 4,5,6-trifluoro-1-methylbenzimidazol-2-yl, 5-bromo-6-benzyloxy-1-methylbenzimidazol-2-yl, 6-bromo-5-benzyloxy-1-methylbenzimidazol-2-yl, 7-chloro-1-methylbenzimidazol-2-yl, 4-chloro-1-methylbenzimidazol-2-yl, 6-hydroxy-1,5,7-trimethylbenzimidazol-2-yl, 5-hydroxy-1,4,6-trimethylbenzimidazol-2-yl, 1-methylbenzimidazol-6-yl, 1-ethylbenzimidazol-6-yl, 1-propylbenzimidazol-6-yl, 1-isopropylbenzimidazol-6-yl, 1-butylbenzimidazol-6-yl, 1-benzylbenzimidazol-6-yl, 1-methylbenzimidazol-7-yl, 1-ethylbenzimidazol-7-yl, 1-benzylbenzimidazol-7-yl, 1-methylbenzimidazol-4-yl, 1-methylbenzimidazol-5-yl, 1,2-dimethylbenzimidazol-6-yl, 5-hydroxy-1,4,6,7-tetramethylbenzimiazol-2-yl, 1-ethyl-5-hydroxy-4,6,7-trimethylbenzimidazol-2-yl, 1-benzylbenzimidazol-5-yl and 5-acetoxy-1,4,6,7-tetramethylbenzimidazol-2-yl groups.

Z represents a group of formula (i), (ii), (iii), (iv) or (v):

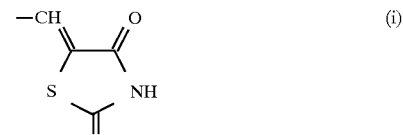 (i)

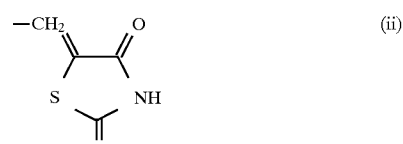 (ii)

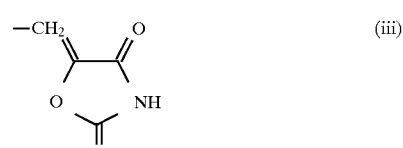 (iii)

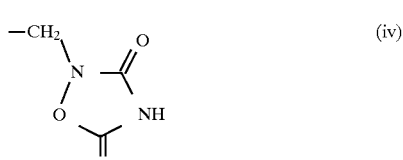 (iv)

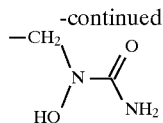

(v)

These formulae (i), (ii), (iii), (iv) and (v) are hereinafter referred to as the 2,4-dioxothiazolidin-5-ylidenylmethyl group, the 2,4-dioxothiazolidin-5-ylmethyl group, the 2,4-dioxooxazolidin-5-ylmethyl group, the 3,5-dioxooxadiazolidin-2-ylmethyl group and the N-hydroxyureidomethyl group, respectively.

Of the compounds of the present invention, we prefer those compounds of formula (I) and salts thereof, in which:

(A1) X represents a benzimidazole group, which is unsubstituted or is substituted by from 1 to 5 of substituents α', defined below;
substituent α' represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$,
wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms,
an aryl group having from 6 to 10 carbon atoms which is unsubstituted or is substituted by at least one substituent selected from the group consisting of substituents β,
said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above;
or an aralkyl group having from 7 to 11 carbon atoms which is unsubstituted or is substituted by at least one substituent selected from the group consisting of substituents β; and/or (A2) R represents a hydrogen atom, an alkyl group having from 1 to 4 carbon atoms, an alkoxy group having from 1 to 4 carbon atoms or a halogen atom;
and especially compounds in which X is as defined in (A1) and R is as defined in (A2).

More preferred compounds of the present invention are those compounds of formula (I) and salts thereof, in which:

(B1) X represents a benzimidazole group, which is unsubstituted or is substituted by from 1 to 5 of substituents α', defined below;
substituent α' represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$,
wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms,
an aryl group having from 6 to 10 carbon atoms which is unsubstituted or is substituted by at least one substituent selected from the group consisting of substituents β,
substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above,
or an aralkyl group having from 7 to 11 carbon atoms which is unsubstituted or is substituted by at least one substituent selected from the group consisting of substituents β; and/or (B2) Y represents an oxygen atom; and/or (B3) Z represents a 2,4-dioxothiazolidin-5-ylidenylmethyl, 2,4-dioxothiazolidin-5-ylmethyl or 2,4,-dioxooxazolidin-5-ylmethyl group; and/or (B4) R represents a hydrogen atom, an alkyl group having from 1 to 4 carbon atoms, an alkoxy group having from 1 to 4 carbon atoms or a halogen atom;
and especially compounds in which X is as defined in (B1), Y is as defined in (B2), Z is as defined in (B3), and R is as defined in (B4).

Still more preferred compounds of the present invention are those compounds of formula (I) and salts thereof, in which:

(C1) X represents a benzimidazole group, which is unsubstituted or is substituted by from 1 to 5 of substituents α', defined below;
substituent α' represents an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$,
wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-alphatic acyl group having from 8 to 12 carbon atoms or an aromatic acyl group having from 7 to 11 carbon atoms,
an aryl group having from 6 to 10 carbon atoms which is unsubstituted or is substituted by from 1 to 3 substituents selected from the group consisting of substituents β,
substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above,
or an aralkyl group having from 7 to 11 carbon atoms which is unsubstituted or is substituted by from 1 to 3 substituents selected from the group consisting of substituents β; and/or (C2) Y represents an oxygen atom; and/or (C3) Z represents a 2,4-dioxothiazolidin-5-ylidenylmethyl or 2,4-dioxothiazolidin-5-ylmethyl group; and/or (C4) R represents a hydrogen atom, a methyl group, a methoxy group, an ethoxy group, a fluorine atom or a chlorine atom; and/or (C5) m represents an integer from 1 to 3;

and especially compounds in which X is as defined in (C1), Y is as defined in (C2), Z is as defined in (C3) R is as defined in (C4), and m is as defined in (C5).

Still more preferred compounds of the present invention are those compounds of formula (I) and salts thereof, in which:

(D1) X represents a benzimidazole group, which is unsubstituted or is substituted by from 1 to 5 of substituents α", defined below;

substituent α" represents an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group, a hydroxy group, an acetoxy group, a benzyl group or a phenyl group; and/or (D2) Y represents an oxygen atom; and/or (D3) Z represents a 2,4-dioxothiazolidin-5-ylmethyl group; and/or (D4) R represents a hydrogen atom, a methyl group or a methoxy group; and/or (D5) m represents an integer from 1 to 3;

and especially compounds in which X is as defined in (D), Y is as defined in (D2), Z is as defined in (D3), R is as defined in (D4), and m is as defined in (D5).

Yet more preferred compounds of the present invention are those compounds of formula (I) and salts thereof, in which:

(E1) X represents a benzimidazole group, which is unsubstituted or is substituted by from 1 to 5 of substituents α'", defined below;

substituent α'" represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group or a phenyl group; and/or (E2) Y represents an oxygen atom; and/or (E3) Z represents a 2,4-dioxothiazolidin-5-ylmethyl group; and/or (E4) R represents a hydrogen atom; and/or (E5) m represents the integer 1 or 2;

and especially compounds in which X is as defined in (E1), Y is as defined in (E2), Z is as defined in (E3), R is as defined in (E4), and b is as defined in (E5).

The most preferred compounds of the present invention are those compounds of formula (I) and salts thereof, in which:

(F1) X represents a benzimidazole group, which is unsubstituted or is substituted by from 1 to 5 of substituents α"", defined below;

substituent α"" represents a methyl group, a methoxy group, a hydroxy group, a benzyl group or an acetoxy group; and/or (F2) Y represents an oxygen atom; and/or (F3) Z represents a 2,4-dioxothiazolidin-5-ylmethyl group; and/or (F4) R represents a hydrogen atom; and/or (F5) m represents the integer 1;

and especially compounds in which X is as defined in (F1), Y is as defined in (F2), Z is as defined in (F3), R is as defined in (F4), and m is as defined in (F5).

The compounds of the present invention each contains a basic group in its molecule, and can thus be converted to salts with acids by conventional methods. There is no particular restriction on the nature of such salts, provided that, where the compounds are to be used medically, the compounds are pharmaceutically acceptable, that is it is not less active, or unacceptably less active, nor more toxic, or unacceptably more toxic, than the parent compound. However, where the compound is to be used for non-medical uses, e.g. as an intermediate in the preparation of other compounds, even this restriction does not apply, and there is then no restriction on the nature of the salts which may be formed. Examples of such salts include: salts with mineral acids, especially hydrohalic acids (such as hydrofluoric acid, hydrobromic acid, hydroiodic acid or hydrochloric acid), nitric acid, perchloric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid. We prefer the pharmaceutically acceptable salts.

Also, the compound of the present invention can be converted into a salt with a base by conventional methods. Examples of such salts include: salts with an alkali metal, such as sodium, potassium or lithium; salts with an alkaline earth metal, such as barium or calcium; and salts with another metal, such as magnesium or aluminum. We prefer the pharmaceutically acceptable salts.

The compounds of formula (I) of the present invention can exist in the form of various isomers due to the presence of asymmetric carbon atoms. Thus, where Z represents a 2,4-dioxothiazolidin-5-ylmethyl or 2,4-dioxooxazolidin-5-ylmethyl group, the carbon atom at the 5-position is asymmetric. Although these isomers are all represented herein by a single molecular formula (I), the present invention includes both the individual, isolated isomers and mixtures, including racemates, thereof and the isomers may be present in such mixtures in any proportions. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

The compounds of formula (I) wherein Z represents a 2,4-dioxothiazolidin-5-ylmethyl, 2,4-dioxothiazolidin-5-ylidenylmethyl, 2,4-dioxooxazolidin-5-ylmethyl or 3,5-dioxooxadiazolidin-2-ylmethyl group can exist in the form of various tautomeric isomers as shown in the following schemes α, β, γ and δ, respectively:

Scheme α

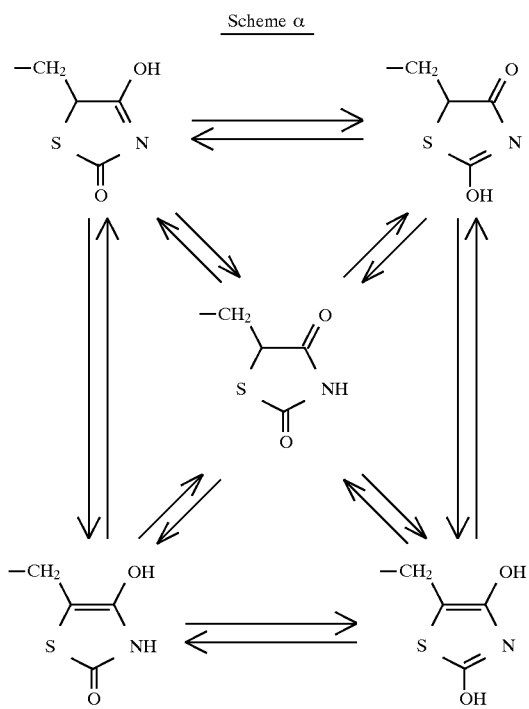

Scheme β

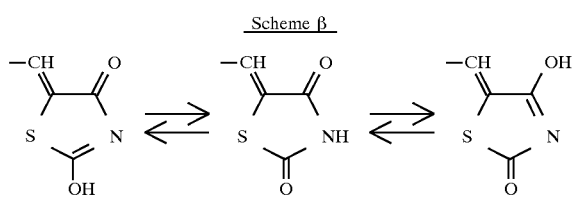

Scheme γ

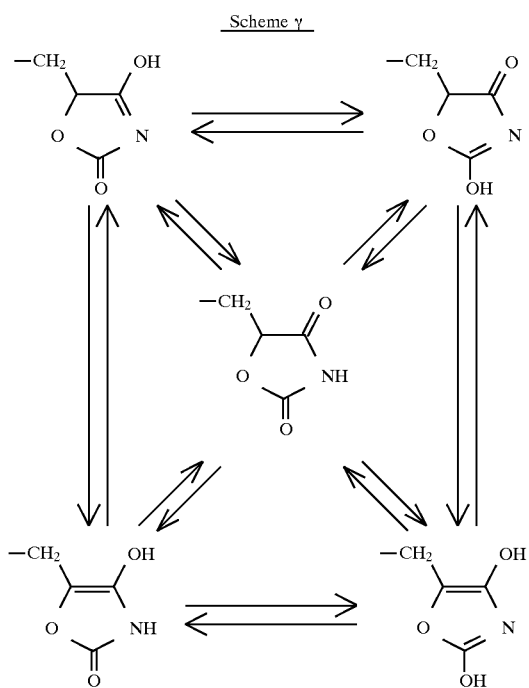

Scheme δ

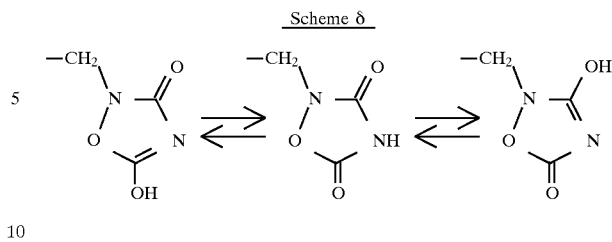

In the above formula (I), all tautomers based thereon and mixtures of equivalent weights or non-equivalent weights of these tautomers are represented by one formula. Thus, all of these isomers and mixtures of these isomers are included in the present invention.

Moreover, the present invention also includes all solvates, for example hydrates, of the compounds of formula (I) and salts thereof, where the relevant compound is capable of forming a solvate.

The invention also embraces all compounds which could be converted in the living mammalian, for example human, body to a compound of formula (I) or a salt thereof by the action of the metabolism, that is so-called "pro-drugs" of the compounds of formula (I) and salts thereof.

Examples of certain compounds of the present invention are given in the following formulae (I-1) to (I-5):

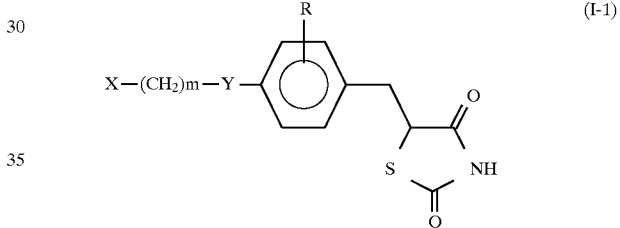

(I-1)

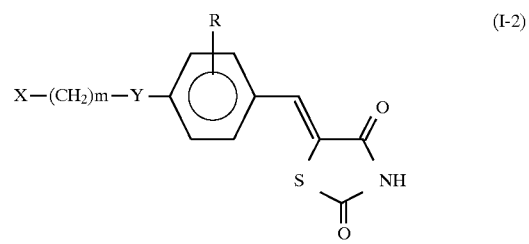

(I-2)

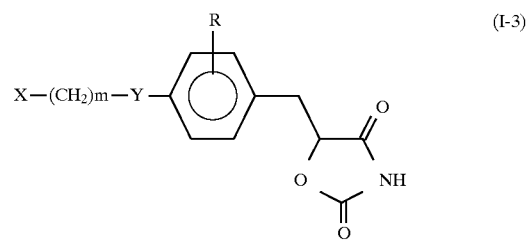

(I-3)

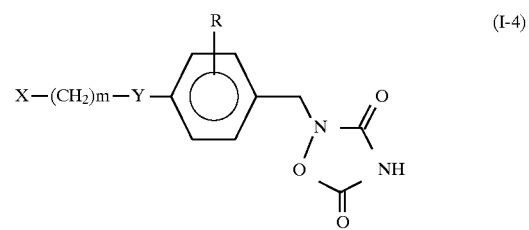

(I-4)

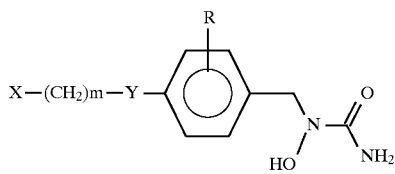

(I-5)

In the above formulae, the substituents are as defined in the following one of Tables 1 to 5, respectively. That is, Table 1 relates to formula (I-1), Table 2 relates to formula (I-2), and so on to Table 5, which relates to formula (I-5). In the Tables, the following abbreviations are used:

| | |
|---|---|
| Bu | butyl |
| iBu | isobutyl |
| sBu | sec-butyl |
| tBu | t-butyl |
| Bz | benzyl |
| Et | ethyl |
| Me | methyl |
| Pr | propyl |
| iPr | isopropyl |

TABLE 1

| Compound No. | X | Y | m | R |
|---|---|---|---|---|
| 1-1 | benzimidazol-2-yl (NH) | O | 1 | H |
| 1-2 | benzimidazol-2-yl (NH) | O | 2 | H |
| 1-3 | benzimidazol-2-yl (NH) | O | 3 | H |
| 1-4 | benzimidazol-2-yl (NH) | O | 4 | H |
| 1-5 | benzimidazol-2-yl (NH) | O | 5 | MeO |
| 1-6 | benzimidazol-2-yl (NH) | S | 1 | H |

TABLE 1-continued

| Compound No. | X | Y | m | R |
|---|---|---|---|---|
| 1-7 | benzimidazol-2-yl (NH) | O | 1 | MeO |
| 1-8 | benzimidazol-2-yl (NH) | O | 1 | Cl |
| 1-9 | benzimidazol-2-yl (NH) | O | 1 | Me |
| 1-10 | benzimidazol-2-yl (NH) | S | 1 | MeO |
| 1-11 | benzimidazol-2-yl (NMe) | O | 1 | H |
| 1-12 | benzimidazol-2-yl (NMe) | O | 2 | H |
| 1-13 | benzimidazol-2-yl (NMe) | O | 3 | H |
| 1-14 | benzimidazol-2-yl (NMe) | O | 4 | H |
| 1-15 | benzimidazol-2-yl (NMe) | O | 5 | H |
| 1-16 | benzimidazol-2-yl (NMe) | S | 1 | H |
| 1-17 | benzimidazol-2-yl (NMe) | S | 2 | H |

TABLE 1-continued

| Compound No. | X | Y | m | R |
|---|---|---|---|---|
| 1-18 | benzimidazole, N-Me | O | 1 | MeO |
| 1-19 | benzimidazole, N-Me | O | 1 | EtO |
| 1-20 | benzimidazole, N-Me | O | 1 | Cl |
| 1-21 | benzimidazole, N-Me | O | 1 | F |
| 1-22 | benzimidazole, N-Me | O | 1 | Me |
| 1-23 | benzimidazole, N-Me | O | 1 | iPr |
| 1-24 | benzimidazole, N-Me | O | 2 | Et |
| 1-25 | benzimidazole, N-Me | S | 1 | Cl |
| 1-26 | benzimidazole, N-Me | S | 1 | Me |
| 1-27 | benzimidazole, N-Et | O | 1 | H |
| 1-28 | benzimidazole, N-Et | O | 2 | H |
| 1-29 | benzimidazole, N-Et | O | 3 | tBu |
| 1-30 | benzimidazole, N-Et | O | 1 | Me |
| 1-31 | benzimidazole, N-Et | O | 1 | MeO |
| 1-32 | benzimidazole, N-Et | S | 1 | H |
| 1-33 | benzimidazole, N-Et | S | 1 | PrO |
| 1-34 | benzimidazole, N-Et | S | 1 | Me |
| 1-35 | benzimidazole, N-Pr | O | 1 | H |
| 1-36 | benzimidazole, N-Pr | O | 3 | H |
| 1-37 | benzimidazole, N-Pr | O | 1 | F |
| 1-38 | benzimidazole, N-Pr | S | 1 | H |
| 1-39 | benzimidazole, N-iPr | O | 1 | H |

TABLE 1-continued

| Compound No. | X | Y | m | R |
|---|---|---|---|---|
| 1-40 | benzimidazole, N-iPr | O | 2 | H |
| 1-41 | benzimidazole, N-iPr | S | 1 | H |
| 1-42 | benzimidazole, N-iPr | S | 5 | Cl |
| 1-43 | benzimidazole, N-Bu | O | 1 | H |
| 1-44 | benzimidazole, N-Bu | O | 4 | H |
| 1-45 | benzimidazole, N-Bu | S | 1 | H |
| 1-46 | 5-MeO-benzimidazole, N-H | O | 1 | H |
| 1-47 | 5-MeO-benzimidazole, N-H | O | 3 | H |
| 1-48 | 5-MeO-benzimidazole, N-H | S | 1 | H |
| 1-49 | 5-MeO-benzimidazole, N-Me | O | 1 | H |
| 1-50 | 5-MeO-benzimidazole, N-Me | O | 2 | H |
| 1-51 | 5-MeO-benzimidazole, N-Me | O | 3 | H |
| 1-52 | 5-MeO-benzimidazole, N-Me | O | 4 | H |
| 1-53 | 5-MeO-benzimidazole, N-Me | O | 5 | H |
| 1-54 | 5-MeO-benzimidazole, N-Me | S | 1 | H |
| 1-55 | 5-MeO-benzimidazole, N-Me | S | 2 | H |
| 1-56 | 5-MeO-benzimidazole, N-Me | O | 1 | Me |
| 1-57 | 5-MeO-benzimidazole, N-Me | O | 1 | MeO |
| 1-58 | 5-MeO-benzimidazole, N-Me | O | 1 | F |
| 1-59 | 5-MeO-benzimidazole, N-Me | O | 1 | Cl |
| 1-60 | 5-MeO-benzimidazole, N-Et | O | 1 | H |
| 1-61 | 5-MeO-benzimidazole, N-Et | O | 2 | H |

TABLE 1-continued

| Compound No. | X | Y | m | R |
|---|---|---|---|---|
| 1-62 | 6-MeO-benzimidazole, N-Et | O | 1 | MeO |
| 1-63 | 6-MeO-benzimidazole, N-Et | S | 1 | H |
| 1-64 | 6-MeO-benzimidazole, N-Pr | O | 1 | H |
| 1-65 | 6-MeO-benzimidazole, N-Pr | S | 1 | H |
| 1-66 | 6-MeO-benzimidazole, N-iPr | O | 1 | H |
| 1-67 | 6-MeO-benzimidazole, N-iBu | O | 1 | H |
| 1-68 | 6-MeO-benzimidazole, N-iBu | S | 1 | H |
| 1-69 | 6-EtO-benzimidazole, N-Me | O | 1 | H |
| 1-70 | 6-EtO-benzimidazole, N-Me | O | 1 | MeO |
| 1-71 | 6-EtO-benzimidazole, N-Me | O | 1 | Cl |
| 1-72 | 6-EtO-benzimidazole, N-Me | O | 2 | H |
| 1-73 | 6-EtO-benzimidazole, N-Me | O | 3 | H |
| 1-74 | 6-EtO-benzimidazole, N-Me | S | 1 | H |
| 1-75 | 6-EtO-benzimidazole, N-Me | S | 4 | Et |
| 1-76 | 6-PrO-benzimidazole, N-Me | O | 1 | H |
| 1-77 | 6-PrO-benzimidazole, N-Me | S | 1 | H |
| 1-78 | 6-iPrO-benzimidazole, N-Me | O | 1 | H |
| 1-79 | 6-iPrO-benzimidazole, N-Me | O | 3 | H |
| 1-80 | 6-BuO-benzimidazole, N-Me | O | 1 | H |
| 1-81 | 6-iBuO-benzimidazole, N-Me | O | 1 | H |
| 1-82 | 6-sBuO-benzimidazole, N-Me | O | 1 | H |
| 1-83 | 6-tBuO-benzimidazole, N-Me | O | 1 | H |

TABLE 1-continued

| Compound No. | X | Y | m | R |
|---|---|---|---|---|
| 1-84 | 6-BuO, 1-Pr benzimidazol-2-yl | O | 1 | H |
| 1-85 | 6-BzO, 1-Me benzimidazol-2-yl | O | 1 | H |
| 1-86 | 5-MeO, 6-Me, 1-Me benzimidazol-2-yl | O | 1 | H |
| 1-87 | 5-MeO, 6-Br, 1-Me benzimidazol-2-yl | O | 1 | H |
| 1-88 | 5-EtO, 6-F, 1-Me benzimidazol-2-yl | O | 1 | H |
| 1-89 | 5,7-di-F, 1-Me benzimidazol-2-yl | O | 1 | H |
| 1-90 | 6-F, 1-Me benzimidazol-2-yl | O | 1 | H |
| 1-91 | 5-Cl, 6-Me, 1-Me benzimidazol-2-yl | O | 1 | H |
| 1-92 | 5-Cl, 6-Et, 1-Et benzimidazol-2-yl | O | 1 | H |
| 1-93 | 5-Et, 1-Me benzimidazol-2-yl | O | 1 | H |

TABLE 1-continued

| Compound No. | X | Y | m | R |
|---|---|---|---|---|
| 1-94 | 6-Br, 1-Me benzimidazol-2-yl | O | 1 | H |
| 1-95 | 5-CF$_3$, 7-Br, 1-Me benzimidazol-2-yl | O | 1 | H |
| 1-96 | 5-CF$_3$, 7-Cl, 1-Me benzimidazol-2-yl | O | 1 | H |
| 1-97 | 7-CF$_3$, 1-Me benzimidazol-2-yl | O | 1 | H |
| 1-98 | 6-CF$_3$, 1-Me benzimidazol-2-yl | O | 1 | H |
| 1-99 | 5-Br, 6-Me, 7-Me, 1-Me benzimidazol-2-yl | O | 1 | H |
| 1-100 | 5-F, 6-Cl, 1-Me benzimidazol-2-yl | O | 1 | H |
| 1-101 | 5-Br, 7-Me, 1-Me benzimidazol-2-yl | O | 1 | H |
| 1-102 | 6-tBu, 1-Me benzimidazol-2-yl | O | 1 | H |
| 1-103 | 5-HO, 1-Me benzimidazol-2-yl | O | 1 | H |

TABLE 1-continued

| Compound No. | X | Y | m | R |
|---|---|---|---|---|
| 1-104 | benzimidazole, 7-Me, N1-Me | O | 1 | H |
| 1-105 | benzimidazole, 6,7-diCl, N1-Me | O | 1 | H |
| 1-106 | benzimidazole, 5,6,7-triF, N1-Me | O | 1 | H |
| 1-107 | benzimidazole, 5-Br, 6-OBz, N1-Me | O | 1 | H |
| 1-108 | benzimidazole, 7-Cl, N1-Me | O | 1 | H |
| 1-109 | benzimidazole, 5-Me, 6-OH, 7-Me, N1-Me | O | 1 | H |
| 1-110 | benzimidazole, 5-Me, 6-OH, 7-Me, N1-Me | O | 2 | H |
| 1-111 | benzimidazole, 5-Me, 6-OH, 7-Me, N1-Me | O | 3 | H |
| 1-112 | benzimidazole, 5-Me, 6-OH, 7-Me, N1-Me | S | 1 | H |
| 1-113 | benzimidazole, 5-Me, 6-OH, 7-Me, N1-Me | O | 1 | Me |
| 1-114 | benzimidazole, 5-Me, 6-OH, 7-Me, N1-Me | O | 1 | MeO |
| 1-115 | benzimidazole, 5-Me, 6-OH, 7-Me, N1-Me | O | 1 | Cl |
| 1-116 | benzimidazole, NH | O | 1 | H |
| 1-117 | benzimidazole, NH | S | 1 | H |
| 1-118 | benzimidazole, N1-Me | O | 1 | H |
| 1-119 | benzimidazole, N1-Me | O | 2 | H |
| 1-120 | benzimidazole, N1-Me | O | 3 | H |
| 1-121 | benzimidazole, N1-Me | O | 4 | H |
| 1-122 | benzimidazole, N1-Me | O | 5 | H |
| 1-123 | benzimidazole, N1-Me | O | 1 | MeO |
| 1-124 | benzimidazole, N1-Me | O | 1 | Cl |

TABLE 1-continued

| Compound No. | X | Y | m | R |
|---|---|---|---|---|
| 1-125 | benzimidazole-N-Me | S | 1 | H |
| 1-126 | benzimidazole-N-Me | S | 3 | H |
| 1-127 | benzimidazole-N-Et | O | 1 | H |
| 1-128 | benzimidazole-N-Et | S | 1 | H |
| 1-129 | benzimidazole-N-Pr | O | 1 | H |
| 1-130 | benzimidazole-N-Pr | O | 1 | Cl |
| 1-131 | benzimidazole-N-iPr | O | 1 | H |
| 1-132 | benzimidazole-N-iPr | S | 1 | H |
| 1-133 | benzimidazole-N-Bu | O | 1 | H |
| 1-134 | benzimidazole-N-Bz | O | 1 | H |
| 1-135 | benzimidazole-N-Bz | O | 3 | H |
| 1-136 | benzimidazole-N-Bz | S | 1 | H |
| 1-137 | benzimidazole-N-Me | O | 1 | H |
| 1-138 | benzimidazole-N-Et | O | 1 | H |
| 1-139 | benzimidazole-N-Bz | O | 1 | H |
| 1-140 | benzimidazole-N-Bz | S | 1 | H |
| 1-141 | benzimidazole-N | O | 1 | H |
| 1-142 | benzimidazole-N-Me | O | 1 | H |
| 1-143 | benzimidazole-N-Me | O | 1 | H |
| 1-144 | 2-Me-benzimidazole-N-Me | O | 1 | H |
| 1-145 | 2-Me-benzimidazole-N-Me | S | 1 | H |

TABLE 1-continued

| Compound No. | X | Y | m | R |
|---|---|---|---|---|
| 1-146 | (MeO-benzimidazole, N-Me) | O | 1 | H |
| 1-147 | (MeO-benzimidazole, N-Me) | O | 2 | H |
| 1-148 | (MeO-benzimidazole, N-Me) | O | 3 | H |
| 1-149 | (MeO-benzimidazole, N-Me) | O | 4 | H |
| 1-150 | (MeO-benzimidazole, N-Me) | O | 5 | H |
| 1-151 | (MeO-benzimidazole, N-Me) | S | 1 | H |
| 1-152 | (MeO-benzimidazole, N-Me) | S | 2 | H |
| 1-153 | (MeO-benzimidazole, N-Me) | O | 1 | Me |
| 1-154 | (MeO-benzimidazole, N-Me) | O | 2 | Me |
| 1-155 | (MeO-benzimidazole, N-Me) | O | 1 | F |
| 1-156 | (MeO-benzimidazole, N-Me) | O | 1 | Cl |
| 1-157 | (MeO-benzimidazole, N-Et) | O | 1 | H |
| 1-158 | (MeO-benzimidazole, N-Et) | O | 2 | H |
| 1-159 | (MeO-benzimidazole, N-Et) | O | 1 | MeO |
| 1-160 | (MeO-benzimidazole, N-Et) | S | 1 | H |
| 1-161 | (MeO-benzimidazole, N-Pr) | O | 1 | H |
| 1-162 | (MeO-benzimidazole, N-Pr) | S | 1 | H |
| 1-163 | (MeO-benzimidazole, N-iPr) | O | 1 | H |
| 1-164 | (MeO-benzimidazole, N-iBu) | O | 1 | H |
| 1-165 | (MeO-benzimidazole, N-iBu) | S | 1 | H |

TABLE 1-continued

| Compound No. | X | Y | m | R |
|---|---|---|---|---|
| 1-166 | benzimidazole, N-Me, EtO-substituted | O | 1 | H |
| 1-167 | benzimidazole, N-Me, EtO-substituted | O | 1 | MeO |
| 1-168 | benzimidazole, N-Me, EtO-substituted | O | 1 | Cl |
| 1-169 | benzimidazole, N-Me, EtO-substituted | O | 2 | H |
| 1-170 | benzimidazole, N-Me, EtO-substituted | O | 3 | H |
| 1-171 | benzimidazole, N-Me, EtO-substituted | S | 1 | H |
| 1-172 | benzimidazole, N-Me, EtO-substituted | S | 4 | Et |
| 1-173 | benzimidazole, N-Me, PrO-substituted | O | 1 | H |
| 1-174 | benzimidazole, N-Me, PrO-substituted | S | 1 | H |
| 1-175 | benzimidazole, N-Me, iPrO-substituted | O | 1 | H |
| 1-176 | benzimidazole, N-Me, iPrO-substituted | O | 3 | H |
| 1-177 | benzimidazole, N-Me, BuO-substituted | O | 1 | H |
| 1-178 | benzimidazole, N-Me, iBuO-substituted | O | 1 | H |
| 1-179 | benzimidazole, N-Me, sBuO-substituted | O | 1 | H |
| 1-180 | benzimidazole, N-Me, tBuO-substituted | O | 1 | H |
| 1-181 | benzimidazole, N-Pr, BuO-substituted | O | 1 | H |
| 1-182 | benzimidazole, N-Me, BzO-substituted | O | 1 | H |
| 1-183 | benzimidazole, N-Me, MeO- and Me-substituted | O | 1 | H |
| 1-184 | benzimidazole, N-Me, MeO- and Br-substituted | O | 1 | H |
| 1-185 | benzimidazole, N-Me, EtO- and F-substituted | O | 1 | H |

TABLE 1-continued

| Compound No. | X | Y | m | R |
|---|---|---|---|---|
| 1-186 | 4,7-difluoro-1-methyl-benzimidazol-2-yl | O | 1 | H |
| 1-187 | 5-fluoro-1-methyl-benzimidazol-2-yl | O | 1 | H |
| 1-188 | 5-chloro-6-methyl-1-methyl-benzimidazol-2-yl | O | 1 | H |
| 1-189 | 5-chloro-7-fluoro-1-ethyl-benzimidazol-2-yl | O | 1 | H |
| 1-190 | 6-ethyl-1-methyl-benzimidazol-2-yl | O | 1 | H |
| 1-191 | 5-bromo-1-methyl-benzimidazol-2-yl | O | 1 | H |
| 1-192 | 7-bromo-5-trifluoromethyl-1-methyl-benzimidazol-2-yl | O | 1 | H |
| 1-193 | 7-chloro-5-trifluoromethyl-1-methyl-benzimidazol-2-yl | O | 1 | H |
| 1-194 | 4-trifluoromethyl-1-methyl-benzimidazol-2-yl | O | 1 | H |
| 1-195 | 6-trifluoromethyl-1-methyl-benzimidazol-2-yl | O | 1 | H |
| 1-196 | 5-bromo-6,7-dimethyl-1-methyl-benzimidazol-2-yl | O | 1 | H |
| 1-197 | 5-fluoro-6-chloro-1-methyl-benzimidazol-2-yl | O | 1 | H |
| 1-198 | 5-bromo-7-methyl-1-methyl-benzimidazol-2-yl | O | 2 | H |
| 1-199 | 6-tBu-1-methyl-benzimidazol-2-yl | O | 1 | H |
| 1-200 | 6-hydroxy-1-methyl-benzimidazol-2-yl | O | 1 | H |
| 1-201 | 4-methyl-1-methyl-benzimidazol-2-yl | O | 1 | H |
| 1-202 | 6,7-dichloro-1-methyl-benzimidazol-2-yl | O | 1 | H |
| 1-203 | 5,6,7-trifluoro-1-methyl-benzimidazol-2-yl | O | 1 | H |
| 1-204 | 5-bromo-6-benzoyloxy-1-methyl-benzimidazol-2-yl | O | 1 | H |

TABLE 1-continued

| Compound No. | X | Y | m | R |
|---|---|---|---|---|
| 1-205 | 1-Me-4-Cl-benzimidazol-2-yl | O | 1 | H |
| 1-206 | 1-Me-4,6-diMe-5-OH-benzimidazol-2-yl | O | 1 | H |
| 1-207 | 1-Me-4,6-diMe-5-OH-benzimidazol-2-yl | O | 2 | H |
| 1-208 | 1-Me-4,6-diMe-5-OH-benzimidazol-2-yl | O | 3 | H |
| 1-209 | 1-Me-4,6-diMe-5-OH-benzimidazol-2-yl | S | 1 | H |
| 1-210 | 1-Me-4,6-diMe-5-OH-benzimidazol-2-yl | O | 1 | Me |
| 1-211 | 1-Me-4,6-diMe-5-OH-benzimidazol-2-yl | O | 1 | MeO |
| 1-212 | 1-Me-4,6-diMe-5-OH-benzimidazol-2-yl | O | 1 | Cl |
| 1-213 | 1-Me-benzimidazol-5-yl | O | 1 | H |
| 1-214 | 1-Me-benzimidazol-5-yl | O | 2 | H |
| 1-215 | 1-Me-benzimidazol-5-yl | O | 3 | H |
| 1-216 | 1-Me-benzimidazol-5-yl | O | 4 | H |
| 1-217 | 1-Me-benzimidazol-5-yl | O | 5 | H |
| 1-218 | 1-Me-benzimidazol-5-yl | O | 1 | MeO |
| 1-219 | 1-Me-benzimidazol-5-yl | O | 1 | Cl |
| 1-220 | 1-Me-benzimidazol-5-yl | S | 1 | H |
| 1-221 | 1-Me-benzimidazol-5-yl | S | 3 | H |
| 1-222 | 1-Et-benzimidazol-5-yl | O | 1 | H |
| 1-223 | 1-Et-benzimidazol-5-yl | S | 1 | H |

TABLE 1-continued

| Compound No. | X | Y | m | R |
|---|---|---|---|---|
| 1-224 | N-Pr benzimidazole (6-yl) | O | 1 | H |
| 1-225 | N-Pr benzimidazole (6-yl) | O | 1 | Cl |
| 1-226 | N-iPr benzimidazole (6-yl) | O | 1 | H |
| 1-227 | N-iPr benzimidazole (6-yl) | S | 1 | H |
| 1-228 | N-Bu benzimidazole (6-yl) | O | 1 | H |
| 1-229 | N-Bz benzimidazole (6-yl) | O | 1 | H |
| 1-230 | N-Bz benzimidazole (6-yl) | O | 3 | H |
| 1-231 | N-Bz benzimidazole (6-yl) | S | 1 | H |
| 1-232 | N-Me benzimidazole (4-yl) | O | 1 | H |
| 1-233 | N-Et benzimidazole (4-yl) | O | 1 | H |
| 1-234 | N-Bz benzimidazole (4-yl) | O | 1 | H |
| 1-235 | N-Bz benzimidazole (4-yl) | S | 1 | H |
| 1-236 | 1,2-diMe benzimidazol-2-yl | O | 1 | H |
| 1-237 | 1,4,7-triMe-5-OH-6-Me benzimidazol-2-yl | O | 1 | H |
| 1-238 | 1,4,7-triMe-5-OH-6-Me benzimidazol-2-yl | O | 2 | H |
| 1-239 | 1,4,7-triMe-5-OH-6-Me benzimidazol-2-yl | O | 3 | H |
| 1-240 | 1,4,7-triMe-5-OH-6-Me benzimidazol-2-yl | O | 4 | H |
| 1-241 | 1,4,7-triMe-5-OH-6-Me benzimidazol-2-yl | S | 1 | H |
| 1-242 | 1,4,7-triMe-5-OH-6-Me benzimidazol-2-yl | O | 1 | MeO |

TABLE 1-continued

| Compound No. | X | Y | m | R |
|---|---|---|---|---|
| 1-243 | 5,6-dimethyl-4,7-dimethyl-6-hydroxy-benzimidazol-2-yl (N1-Me) | O | 1 | Cl |
| 1-244 | 5,6-dimethyl-4,7-dimethyl-6-hydroxy-benzimidazol-2-yl (N1-Me) | O | 1 | F |
| 1-245 | 5,6-dimethyl-4,7-dimethyl-6-hydroxy-benzimidazol-2-yl (N1-Me) | O | 1 | CF$_3$ |
| 1-246 | 5,6-dimethyl-4,7-dimethyl-6-hydroxy-benzimidazol-2-yl (N1-Me) | O | 1 | Et |
| 1-247 | 5,6-dimethyl-4,7-dimethyl-6-hydroxy-benzimidazol-2-yl (N1-Et) | O | 1 | H |
| 1-248 | 5,6-dimethyl-4,7-dimethyl-6-hydroxy-benzimidazol-2-yl (N1-Et) | O | 2 | H |
| 1-249 | 5,6-dimethyl-4,7-dimethyl-6-hydroxy-benzimidazol-2-yl (N1-Et) | O | 1 | MeO |
| 1-250 | 5,6-dimethyl-4,7-dimethyl-6-acetoxy-benzimidazol-2-yl (N1-Me) | O | 1 | H |

TABLE 2

| Compound No. | X | Y | m | R |
|---|---|---|---|---|
| 2-1 | benzimidazol-2-yl (NH) | O | 1 | H |
| 2-2 | benzimidazol-2-yl (NH) | O | 2 | H |
| 2-3 | benzimidazol-2-yl (NH) | O | 3 | H |
| 2-4 | benzimidazol-2-yl (NH) | O | 4 | H |
| 2-5 | benzimidazol-2-yl (NH) | O | 5 | MeO |
| 2-6 | benzimidazol-2-yl (NH) | S | 1 | H |
| 2-7 | benzimidazol-2-yl (NH) | O | 1 | MeO |
| 2-8 | benzimidazol-2-yl (NH) | O | 1 | Cl |
| 2-9 | benzimidazol-2-yl (NH) | O | 1 | Me |
| 2-10 | benzimidazol-2-yl (NH) | S | 1 | MeO |
| 2-11 | benzimidazol-2-yl (N-Me) | O | 1 | H |

TABLE 2-continued
| Compound No. | X | Y | m | R |
|---|---|---|---|---|
| 2-12 | 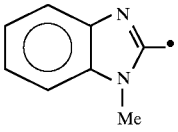 | O | 2 | H |
| 2-13 | 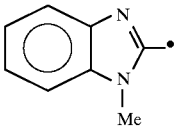 | O | 3 | H |
| 2-14 | 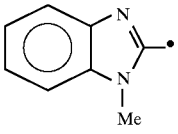 | O | 4 | H |
| 2-15 | 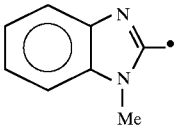 | O | 5 | H |
| 2-16 | 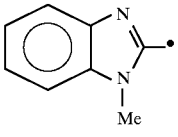 | S | 1 | H |
| 2-17 | 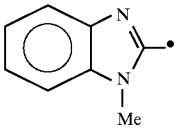 | S | 2 | H |
| 2-18 | 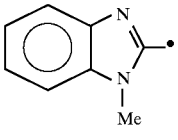 | O | 1 | MeO |
| 2-19 | 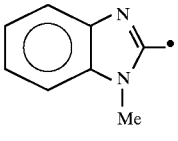 | O | 1 | EtO |
| 2-20 | 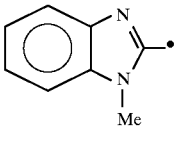 | O | 1 | Cl |
| 2-21 | 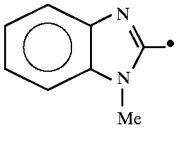 | O | 1 | F |
| 2-22 | 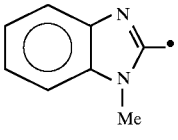 | O | 1 | Me |
TABLE 2-continued
| Compound No. | X | Y | m | R |
|---|---|---|---|---|
| 2-23 | 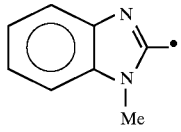 | O | 1 | iPr |
| 2-24 | 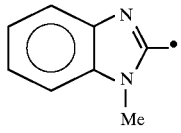 | O | 2 | Et |
| 2-25 | 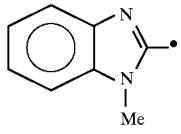 | S | 1 | Cl |
| 2-26 | 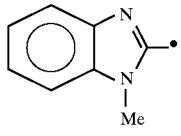 | S | 1 | Me |
| 2-27 | 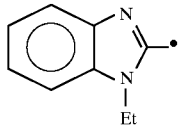 | O | 1 | H |
| 2-28 | 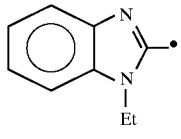 | O | 2 | H |
| 2-29 | 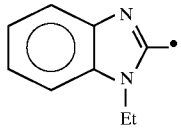 | O | 3 | tBu |
| 2-30 | 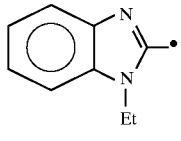 | O | 1 | Me |
| 2-31 | 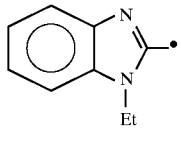 | O | 1 | MeO |
| 2-32 | 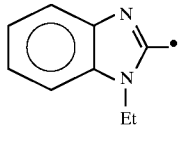 | S | 1 | H |
| 2-33 | 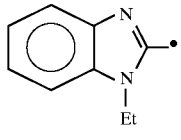 | S | 1 | PrO |

TABLE 2-continued

| Compound No. | X | Y | m | R |
|---|---|---|---|---|
| 2-34 | benzimidazole, N-Et | S | 1 | Me |
| 2-35 | benzimidazole, N-Pr | O | 1 | H |
| 2-36 | benzimidazole, N-Pr | O | 3 | H |
| 2-37 | benzimidazole, N-Pr | O | 1 | F |
| 2-38 | benzimidazole, N-Pr | S | 1 | H |
| 2-39 | benzimidazole, N-iPr | O | 1 | H |
| 2-40 | benzimidazole, N-iPr | O | 2 | H |
| 2-41 | benzimidazole, N-iPr | S | 1 | H |
| 2-42 | benzimidazole, N-iPr | S | 5 | Cl |
| 2-43 | benzimidazole, N-Bu | O | 1 | H |
| 2-44 | benzimidazole, N-Bu | O | 4 | H |
| 2-45 | benzimidazole, N-Bu | S | 1 | H |
| 2-46 | 5-MeO-benzimidazole, N-H | O | 1 | H |
| 2-47 | 5-MeO-benzimidazole, N-H | O | 3 | H |
| 2-48 | 5-MeO-benzimidazole, N-H | S | 1 | H |
| 2-49 | 5-MeO-benzimidazole, N-Me | O | 1 | H |
| 2-50 | 5-MeO-benzimidazole, N-Me | O | 2 | H |
| 2-51 | 5-MeO-benzimidazole, N-Me | O | 3 | H |
| 2-52 | 5-MeO-benzimidazole, N-Me | O | 4 | H |
| 2-53 | 5-MeO-benzimidazole, N-Me | O | 5 | H |
| 2-54 | 5-MeO-benzimidazole, N-Me | S | 1 | H |
| 2-55 | 5-MeO-benzimidazole, N-Me | S | 2 | H |

TABLE 2-continued

| Compound No. | X | Y | m | R |
|---|---|---|---|---|
| 2-56 | 6-MeO-benzimidazole, N-Me | O | 1 | Me |
| 2-57 | 6-MeO-benzimidazole, N-Me | O | 1 | MeO |
| 2-58 | 6-MeO-benzimidazole, N-Me | O | 1 | F |
| 2-59 | 6-MeO-benzimidazole, N-Me | O | 1 | Cl |
| 2-60 | 6-MeO-benzimidazole, N-Et | O | 1 | H |
| 2-61 | 6-MeO-benzimidazole, N-Et | O | 2 | H |
| 2-62 | 6-MeO-benzimidazole, N-Et | O | 1 | MeO |
| 2-63 | 6-MeO-benzimidazole, N-Et | S | 1 | H |
| 2-64 | 6-MeO-benzimidazole, N-Pr | O | 1 | H |
| 2-65 | 6-MeO-benzimidazole, N-Pr | S | 1 | H |
| 2-66 | 6-MeO-benzimidazole, N-iPr | O | 1 | H |
| 2-67 | 6-MeO-benzimidazole, N-iBu | O | 1 | H |
| 2-68 | 6-MeO-benzimidazole, N-iBu | S | 1 | H |
| 2-69 | 6-EtO-benzimidazole, N-Me | O | 1 | H |
| 2-70 | 6-EtO-benzimidazole, N-Me | O | 1 | MeO |
| 2-71 | 6-EtO-benzimidazole, N-Me | O | 1 | Cl |
| 2-72 | 6-EtO-benzimidazole, N-Me | O | 2 | H |
| 2-73 | 6-EtO-benzimidazole, N-Me | O | 3 | H |
| 2-74 | 6-EtO-benzimidazole, N-Me | S | 1 | H |
| 2-75 | 6-EtO-benzimidazole, N-Me | S | 4 | Et |
| 2-76 | 6-PrO-benzimidazole, N-Me | O | 1 | H |
| 2-77 | 6-PrO-benzimidazole, N-Me | S | 1 | H |

TABLE 2-continued

| Compound No. | X | Y | m | R |
|---|---|---|---|---|
| 2-78 | iPrO-benzimidazole-N-Me | O | 1 | H |
| 2-79 | iPrO-benzimidazole-N-Me | O | 3 | H |
| 2-80 | BuO-benzimidazole-N-Me | O | 1 | H |
| 2-81 | iBuO-benzimidazole-N-Me | O | 1 | H |
| 2-82 | sBuO-benzimidazole-N-Me | O | 1 | H |
| 2-83 | tBuO-benzimidazole-N-Me | O | 1 | H |
| 2-84 | BuO-benzimidazole-N-Pr | O | 1 | H |
| 2-85 | BzO-benzimidazole-N-Me | O | 1 | H |
| 2-86 | MeO,Me-benzimidazole-N-Me | O | 1 | H |
| 2-87 | MeO,Br-benzimidazole-N-Me | O | 1 | H |
| 2-88 | EtO,F-benzimidazole-N-Me | O | 1 | H |
| 2-89 | F,F-benzimidazole-N-Me | O | 1 | H |
| 2-90 | F-benzimidazole-N-Me | O | 1 | H |
| 2-91 | Cl,Me-benzimidazole-N-Me | O | 1 | H |
| 2-92 | Cl,Et-benzimidazole-N-Et | O | 1 | H |
| 2-93 | Et-benzimidazole-N-Me | O | 1 | H |
| 2-94 | Br-benzimidazole-N-Me | O | 1 | H |
| 2-95 | CF₃,Br-benzimidazole-N-Me | O | 1 | H |
| 2-96 | CF₃,Cl-benzimidazole-N-Me | O | 1 | H |
| 2-97 | CF₃-benzimidazole-N-Me | O | 1 | H |
| 2-98 | CF₃-benzimidazole-N-Me | O | 1 | H |

TABLE 2-continued

| Compound No. | X | Y | m | R |
|---|---|---|---|---|
| 2-99 | 5-Br, 6-Me, 7-Me, N1-Me benzimidazol-2-yl | O | 1 | H |
| 2-100 | 5-F, 6-Cl, N1-Me benzimidazol-2-yl | O | 1 | H |
| 2-101 | 5-Br, 7-Me, N1-Me benzimidazol-2-yl | O | 1 | H |
| 2-102 | 6-tBu, N1-Me benzimidazol-2-yl | O | 1 | H |
| 2-103 | 5-HO, N1-Me benzimidazol-2-yl | O | 1 | H |
| 2-104 | 7-Me, N1-Me benzimidazol-2-yl | O | 1 | H |
| 2-105 | 6-Cl, 7-Cl, N1-Me benzimidazol-2-yl | O | 1 | H |
| 2-106 | 5-F, 6-F, 7-F, N1-Me benzimidazol-2-yl | O | 1 | H |
| 2-107 | 5-Br, 6-BzO, N1-Me benzimidazol-2-yl | O | 1 | H |
| 2-108 | 7-Cl, N1-Me benzimidazol-2-yl | O | 1 | H |
| 2-109 | 5-Me, 6-HO, 7-Me, N1-Me benzimidazol-2-yl | O | 1 | H |
| 2-110 | 5-Me, 6-HO, 7-Me, N1-Me benzimidazol-2-yl | O | 2 | H |
| 2-111 | 5-Me, 6-HO, 7-Me, N1-Me benzimidazol-2-yl | O | 3 | H |
| 2-112 | 5-Me, 6-HO, 7-Me, N1-Me benzimidazol-2-yl | S | 1 | H |
| 2-113 | 5-Me, 6-HO, 7-Me, N1-Me benzimidazol-2-yl | O | 1 | Me |
| 2-114 | 5-Me, 6-HO, 7-Me, N1-Me benzimidazol-2-yl | O | 1 | MeO |
| 2-115 | 5-Me, 6-HO, 7-Me, N1-Me benzimidazol-2-yl | O | 1 | Cl |
| 2-116 | benzimidazol-5-yl (NH) | O | 1 | H |
| 2-117 | benzimidazol-5-yl (NH) | S | 1 | H |
| 2-118 | N1-Me benzimidazol-5-yl | O | 1 | H |

TABLE 2-continued

| Compound No. | X | Y | m | R |
|---|---|---|---|---|
| 2-119 | benzimidazole-N-Me | O | 2 | H |
| 2-120 | benzimidazole-N-Me | O | 3 | H |
| 2-121 | benzimidazole-N-Me | O | 4 | H |
| 2-122 | benzimidazole-N-Me | O | 5 | H |
| 2-123 | benzimidazole-N-Me | O | 1 | MeO |
| 2-124 | benzimidazole-N-Me | O | 1 | Cl |
| 2-125 | benzimidazole-N-Me | S | 1 | H |
| 2-126 | benzimidazole-N-Me | S | 3 | H |
| 2-127 | benzimidazole-N-Et | O | 1 | H |
| 2-128 | benzimidazole-N-Et | S | 1 | H |
| 2-219 | benzimidazole-N-Pr | O | 1 | H |
| 2-130 | benzimidazole-N-Pr | O | 1 | Cl |
| 2-131 | benzimidazole-N-iPr | O | 1 | H |
| 2-132 | benzimidazole-N-iPr | S | 1 | H |
| 2-133 | benzimidazole-N-Bu | O | 1 | H |
| 2-134 | benzimidazole-N-Bz | O | 1 | H |
| 2-135 | benzimidazole-N-Bz | O | 3 | H |
| 2-136 | benzimidazole-N-Bz | S | 1 | H |
| 2-137 | benzimidazole-N-Me (other isomer) | O | 1 | H |
| 2-138 | benzimidazole-N-Et (other isomer) | O | 1 | H |
| 2-139 | benzimidazole-N-Bz (other isomer) | O | 1 | H |
| 2-140 | benzimidazole-N-Bz (other isomer) | S | 1 | H |

TABLE 2-continued

| Compound No. | X | Y | m | R |
|---|---|---|---|---|
| 2-141 | benzimidazol-1-yl (N-H) | O | 1 | H |
| 2-142 | 1-methylbenzimidazol-4-yl | O | 1 | H |
| 2-143 | 1-methylbenzimidazol-5-yl | O | 1 | H |
| 2-144 | 1,2-dimethylbenzimidazol-5-yl | O | 1 | H |
| 2-145 | 1,2-dimethylbenzimidazol-5-yl | S | 1 | H |
| 2-146 | 5-methoxy-1-methylbenzimidazol-2-yl | O | 1 | H |
| 2-147 | 5-methoxy-1-methylbenzimidazol-2-yl | O | 2 | H |
| 2-148 | 5-methoxy-1-methylbenzimidazol-2-yl | O | 3 | H |
| 2-149 | 5-methoxy-1-methylbenzimidazol-2-yl | O | 4 | H |
| 2-150 | 5-methoxy-1-methylbenzimidazol-2-yl | O | 5 | H |
| 2-151 | 5-methoxy-1-methylbenzimidazol-2-yl | S | 1 | H |
| 2-152 | 5-methoxy-1-methylbenzimidazol-2-yl | S | 2 | H |
| 2-153 | 5-methoxy-1-methylbenzimidazol-2-yl | O | 1 | Me |
| 2-154 | 5-methoxy-1-methylbenzimidazol-2-yl | O | 2 | Me |
| 2-155 | 5-methoxy-1-methylbenzimidazol-2-yl | O | 1 | F |
| 2-156 | 5-methoxy-1-methylbenzimidazol-2-yl | O | 1 | Cl |
| 2-157 | 5-methoxy-1-ethylbenzimidazol-2-yl | O | 1 | H |
| 2-158 | 5-methoxy-1-ethylbenzimidazol-2-yl | O | 2 | H |
| 2-159 | 5-methoxy-1-ethylbenzimidazol-2-yl | O | 1 | MeO |
| 2-160 | 5-methoxy-1-ethylbenzimidazol-2-yl | S | 1 | H |

TABLE 2-continued

| Compound No. | X | Y | m | R |
|---|---|---|---|---|
| 2-161 | 1-Pr, 5-MeO benzimidazol-2-yl | O | 1 | H |
| 2-162 | 1-Pr, 5-MeO benzimidazol-2-yl | S | 1 | H |
| 2-163 | 1-iPr, 5-MeO benzimidazol-2-yl | O | 1 | H |
| 2-164 | 1-iBu, 5-MeO benzimidazol-2-yl | O | 1 | H |
| 2-165 | 1-iBu, 5-MeO benzimidazol-2-yl | S | 1 | H |
| 2-166 | 1-Me, 5-EtO benzimidazol-2-yl | O | 1 | H |
| 2-167 | 1-Me, 5-EtO benzimidazol-2-yl | O | 1 | MeO |
| 2-168 | 1-Me, 5-EtO benzimidazol-2-yl | O | 1 | Cl |
| 2-169 | 1-Me, 5-EtO benzimidazol-2-yl | O | 2 | H |
| 2-170 | 1-Me, 5-EtO benzimidazol-2-yl | O | 3 | H |
| 2-171 | 1-Me, 5-EtO benzimidazol-2-yl | S | 1 | H |
| 2-172 | 1-Me, 5-EtO benzimidazol-2-yl | S | 4 | Et |
| 2-173 | 1-Me, 5-PrO benzimidazol-2-yl | O | 1 | H |
| 2-174 | 1-Me, 5-PrO benzimidazol-2-yl | S | 1 | H |
| 2-175 | 1-Me, 5-iPrO benzimidazol-2-yl | O | 1 | H |
| 2-176 | 1-Me, 5-iPrO benzimidazol-2-yl | O | 3 | H |
| 2-177 | 1-Me, 5-BuO benzimidazol-2-yl | O | 1 | H |
| 2-178 | 1-Me, 5-iBuO benzimidazol-2-yl | O | 1 | H |
| 2-179 | 1-Me, 5-sBuO benzimidazol-2-yl | O | 1 | H |
| 2-180 | 1-Me, 5-tBuO benzimidazol-2-yl | O | 1 | H |

TABLE 2-continued

| Compound No. | X | Y | m | R |
|---|---|---|---|---|
| 2-181 | 1-Pr, 5-BuO benzimidazol-2-yl | O | 1 | H |
| 2-182 | 1-Me, 5-BzO benzimidazol-2-yl | O | 1 | H |
| 2-183 | 1-Me, 5-MeO, 6-Me benzimidazol-2-yl | O | 1 | H |
| 2-184 | 1-Me, 5-MeO, 6-Br benzimidazol-2-yl | O | 1 | H |
| 2-185 | 1-Me, 5-EtO, 6-F benzimidazol-2-yl | O | 1 | H |
| 2-186 | 1-Me, 4,6-diF benzimidazol-2-yl | O | 1 | H |
| 2-187 | 1-Me, 5-F benzimidazol-2-yl | O | 1 | H |
| 2-188 | 1-Me, 5-Cl, 6-Me benzimidazol-2-yl | O | 1 | H |
| 2-189 | 1-Et, 5-Cl, 6-Et benzimidazol-2-yl | O | 1 | H |
| 2-190 | 1-Me, 5-Et benzimidazol-2-yl | O | 1 | H |
| 2-191 | 1-Me, 5-Br benzimidazol-2-yl | O | 1 | H |
| 2-192 | 1-Me, 5-CF3, 7-Br benzimidazol-2-yl | O | 1 | H |
| 2-193 | 1-Me, 5-CF3, 7-Cl benzimidazol-2-yl | O | 1 | H |
| 2-194 | 1-Me, 7-CF3 benzimidazol-2-yl | O | 1 | H |
| 2-195 | 1-Me, 5-CF3 benzimidazol-2-yl | O | 1 | H |
| 2-196 | 1-Me, 4-Me, 5-Me, 6-Br benzimidazol-2-yl | O | 1 | H |
| 2-197 | 1-Me, 5-F, 6-Cl benzimidazol-2-yl | O | 1 | H |
| 2-198 | 1-Me, 3-Me, 4-Me, 6-Br benzimidazol-2-yl | O | 2 | H |
| 2-199 | 1-Me, 5-tBu benzimidazol-2-yl | O | 1 | H |

TABLE 2-continued

| Compound No. | X | Y | m | R |
|---|---|---|---|---|
| 2-200 | (benzimidazole with N-Me, HO-) | O | 1 | H |
| 2-201 | (benzimidazole with N-Me, Me-) | O | 1 | H |
| 2-202 | (benzimidazole with N-Me, Cl, Cl) | O | 1 | H |
| 2-203 | (benzimidazole with N-Me, F, F, F) | O | 1 | H |
| 2-204 | (benzimidazole with N-Me, Br, BzO) | O | 1 | H |
| 2-205 | (benzimidazole with N-Me, Cl) | O | 1 | H |
| 2-206 | (benzimidazole with N-Me, Me, HO, Me) | O | 1 | H |
| 2-207 | (benzimidazole with N-Me, Me, HO, Me) | O | 2 | H |
| 2-208 | (benzimidazole with N-Me, Me, HO, Me) | O | 3 | H |
| 2-209 | (benzimidazole with N-Me, Me, HO, Me) | S | 1 | H |
| 2-210 | (benzimidazole with N-Me, Me, HO, Me) | O | 1 | Me |
| 2-211 | (benzimidazole with N-Me, Me, HO, Me) | O | 1 | MeO |
| 2-212 | (benzimidazole with N-Me, Me, HO, Me) | O | 1 | Cl |
| 2-213 | (benzimidazole with N-Me) | O | 1 | H |
| 2-214 | (benzimidazole with N-Me) | O | 2 | H |
| 2-215 | (benzimidazole with N-Me) | O | 3 | H |
| 2-216 | (benzimidazole with N-Me) | O | 4 | H |
| 2-217 | (benzimidazole with N-Me) | O | 5 | H |
| 2-218 | (benzimidazole with N-Me) | O | 1 | MeO |

TABLE 2-continued

| Compound No. | X | Y | m | R |
|---|---|---|---|---|
| 2-219 | benzimidazole, N-Me | O | 1 | Cl |
| 2-220 | benzimidazole, N-Me | S | 1 | H |
| 2-221 | benzimidazole, N-Me | S | 3 | H |
| 2-222 | benzimidazole, N-Et | O | 1 | H |
| 2-223 | benzimidazole, N-Et | S | 1 | H |
| 2-224 | benzimidazole, N-Pr | O | 1 | H |
| 2-225 | benzimidazole, N-Pr | O | 1 | Cl |
| 2-226 | benzimidazole, N-iPr | O | 1 | H |
| 2-227 | benzimidazole, N-iPr | S | 1 | H |
| 2-228 | benzimidazole, N-Bu | O | 1 | H |
| 2-229 | benzimidazole, N-Bz | O | 1 | H |
| 2-230 | benzimidazole, N-Bz | O | 3 | H |
| 2-231 | benzimidazole, N-Bz | S | 1 | H |
| 2-232 | benzimidazole, N-Me (other position) | O | 1 | H |
| 2-233 | benzimidazole, N-Et (other position) | O | 1 | H |
| 2-234 | benzimidazole, N-Bz (other position) | O | 1 | H |
| 2-235 | benzimidazole, N-Bz (other position) | S | 1 | H |
| 2-236 | benzimidazole, N-Me, 2-Me | O | 1 | H |

TABLE 3

| Compound No. | X | Y | m | R |
|---|---|---|---|---|
| 3-1 | benzimidazol-2-yl, NH | O | 1 | H |

TABLE 3-continued

| Compound No. | X | Y | m | R |
|---|---|---|---|---|
| 3-2 | benzimidazole, N-H | O | 2 | H |
| 3-3 | benzimidazole, N-H | O | 3 | H |
| 3-4 | benzimidazole, N-H | O | 4 | H |
| 3-5 | benzimidazole, N-H | O | 5 | MeO |
| 3-6 | benzimidazole, N-H | S | 1 | H |
| 3-7 | benzimidazole, N-H | O | 1 | MeO |
| 3-8 | benzimidazole, N-H | O | 1 | Cl |
| 3-9 | benzimidazole, N-H | O | 1 | Me |
| 3-10 | benzimidazole, N-H | S | 1 | MeO |
| 3-11 | benzimidazole, N-Me | O | 1 | H |
| 3-12 | benzimidazole, N-Me | O | 2 | H |
| 3-13 | benzimidazole, N-Me | O | 3 | H |
| 3-14 | benzimidazole, N-Me | O | 4 | H |
| 3-15 | benzimidazole, N-Me | O | 5 | H |
| 3-16 | benzimidazole, N-Me | S | 1 | H |
| 3-17 | benzimidazole, N-Me | S | 2 | H |
| 3-18 | benzimidazole, N-Me | O | 1 | MeO |
| 3-19 | benzimidazole, N-Me | O | 1 | EtO |
| 3-20 | benzimidazole, N-Me | O | 1 | Cl |
| 3-21 | benzimidazole, N-Me | O | 1 | F |
| 3-22 | benzimidazole, N-Me | O | 1 | Me |
| 3-23 | benzimidazole, N-Me | O | 1 | iPr |

TABLE 3-continued

| Compound No. | X | Y | m | R |
|---|---|---|---|---|
| 3-24 | benzimidazole, N-Me | O | 2 | Et |
| 3-25 | benzimidazole, N-Me | S | 1 | Cl |
| 3-26 | benzimidazole, N-Me | S | 1 | Me |
| 3-27 | benzimidazole, N-Et | O | 1 | H |
| 3-28 | benzimidazole, N-Et | O | 2 | H |
| 3-29 | benzimidazole, N-Et | O | 3 | tBu |
| 3-30 | benzimidazole, N-Et | O | 1 | Me |
| 3-31 | benzimidazole, N-Et | O | 1 | MeO |
| 3-32 | benzimidazole, N-Et | S | 1 | H |
| 3-33 | benzimidazole, N-Et | S | 1 | PrO |
| 3-34 | benzimidazole, N-Et | S | 1 | Me |
| 3-35 | benzimidazole, N-Pr | O | 1 | H |
| 3-36 | benzimidazole, N-Pr | O | 3 | H |
| 3-37 | benzimidazole, N-Pr | O | 1 | F |
| 3-38 | benzimidazole, N-Pr | S | 1 | H |
| 3-39 | benzimidazole, N-iPr | O | 1 | H |
| 3-40 | benzimidazole, N-iPr | O | 2 | H |
| 3-41 | benzimidazole, N-iPr | S | 1 | H |
| 3-42 | benzimidazole, N-iPr | S | 5 | Cl |
| 3-43 | benzimidazole, N-Bu | O | 1 | H |
| 3-44 | benzimidazole, N-Bu | O | 4 | H |
| 3-45 | benzimidazole, N-Bu | S | 1 | H |

TABLE 3-continued

| Compound No. | X | Y | m | R |
|---|---|---|---|---|
| 3-46 | 5-MeO-benzimidazol-2-yl, N-H | O | 1 | H |
| 3-47 | 5-MeO-benzimidazol-2-yl, N-H | O | 3 | H |
| 3-48 | 5-MeO-benzimidazol-2-yl, N-H | S | 1 | H |
| 3-49 | 5-MeO-benzimidazol-2-yl, N-Me | O | 1 | H |
| 3-50 | 5-MeO-benzimidazol-2-yl, N-Me | O | 2 | H |
| 3-51 | 5-MeO-benzimidazol-2-yl, N-Me | O | 3 | H |
| 3-52 | 5-MeO-benzimidazol-2-yl, N-Me | O | 4 | H |
| 3-53 | 5-MeO-benzimidazol-2-yl, N-Me | O | 5 | H |
| 3-54 | 5-MeO-benzimidazol-2-yl, N-Me | S | 1 | H |
| 3-55 | 5-MeO-benzimidazol-2-yl, N-Me | S | 2 | H |
| 3-56 | 5-MeO-benzimidazol-2-yl, N-Me | O | 1 | Me |
| 3-57 | 5-MeO-benzimidazol-2-yl, N-Me | O | 1 | MeO |
| 3-58 | 5-MeO-benzimidazol-2-yl, N-Me | O | 1 | F |
| 3-59 | 5-MeO-benzimidazol-2-yl, N-Me | O | 1 | Cl |
| 3-60 | 5-MeO-benzimidazol-2-yl, N-Et | O | 1 | H |
| 3-61 | 5-MeO-benzimidazol-2-yl, N-Et | O | 2 | H |
| 3-62 | 5-MeO-benzimidazol-2-yl, N-Et | O | 1 | MeO |
| 3-63 | 5-MeO-benzimidazol-2-yl, N-Et | S | 1 | H |
| 3-64 | 5-MeO-benzimidazol-2-yl, N-Pr | O | 1 | H |
| 3-65 | 5-MeO-benzimidazol-2-yl, N-Pr | S | 1 | H |
| 3-66 | 5-MeO-benzimidazol-2-yl, N-iPr | O | 1 | H |
| 3-67 | 5-MeO-benzimidazol-2-yl, N-iBu | O | 1 | H |

TABLE 3-continued

| Compound No. | X | Y | m | R |
|---|---|---|---|---|
| 3-68 | 6-MeO-benzimidazol-2-yl, N-iBu | S | 1 | H |
| 3-69 | 6-EtO-benzimidazol-2-yl, N-Me | O | 1 | H |
| 3-70 | 6-EtO-benzimidazol-2-yl, N-Me | O | 1 | MeO |
| 3-71 | 6-EtO-benzimidazol-2-yl, N-Me | O | 1 | Cl |
| 3-72 | 6-EtO-benzimidazol-2-yl, N-Me | O | 2 | H |
| 3-73 | 6-EtO-benzimidazol-2-yl, N-Me | O | 3 | H |
| 3-74 | 6-EtO-benzimidazol-2-yl, N-Me | S | 1 | H |
| 3-75 | 6-EtO-benzimidazol-2-yl, N-Me | S | 4 | Et |
| 3-76 | 6-PrO-benzimidazol-2-yl, N-Me | O | 1 | H |
| 3-77 | 6-PrO-benzimidazol-2-yl, N-Me | S | 1 | H |
| 3-78 | 6-iPrO-benzimidazol-2-yl, N-Me | O | 1 | H |
| 3-79 | 6-iPrO-benzimidazol-2-yl, N-Me | O | 3 | H |
| 3-80 | 6-BuO-benzimidazol-2-yl, N-Me | O | 1 | H |
| 3-81 | 6-iBuO-benzimidazol-2-yl, N-Me | O | 1 | H |
| 3-82 | 6-sBuO-benzimidazol-2-yl, N-Me | O | 1 | H |
| 3-83 | 6-tBuO-benzimidazol-2-yl, N-Me | O | 1 | H |
| 3-84 | 6-BuO-benzimidazol-2-yl, N-Pr | O | 1 | H |
| 3-85 | 6-BzO-benzimidazol-2-yl, N-Me | O | 1 | H |
| 3-86 | 5-MeO-6-Me-benzimidazol-2-yl, N-Me | O | 1 | H |
| 3-87 | 5-MeO-6-Br-benzimidazol-2-yl, N-Me | O | 1 | H |
| 3-88 | 5-EtO-6-F-benzimidazol-2-yl, N-Me | O | 1 | H |
| 3-89 | 4,6-diF-benzimidazol-2-yl, N-Me | O | 1 | H |

TABLE 3-continued

| Compound No. | X | Y | m | R |
|---|---|---|---|---|
| 3-90 | 6-F, 1-Me benzimidazol-2-yl | O | 1 | H |
| 3-91 | 5-Cl, 6-Me, 1-Me benzimidazol-2-yl | O | 1 | H |
| 3-92 | 5-Cl, 6-Et, 1-Et benzimidazol-2-yl | O | 1 | H |
| 3-93 | 5-Et, 1-Me benzimidazol-2-yl | O | 1 | H |
| 3-94 | 6-Br, 1-Me benzimidazol-2-yl | O | 1 | H |
| 3-95 | 5-CF₃, 7-Br, 1-Me benzimidazol-2-yl | O | 1 | H |
| 3-96 | 5-CF₃, 7-Cl, 1-Me benzimidazol-2-yl | O | 1 | H |
| 3-97 | 7-CF₃, 1-Me benzimidazol-2-yl | O | 1 | H |
| 3-98 | 6-CF₃, 1-Me benzimidazol-2-yl | O | 1 | H |
| 3-99 | 5-Br, 6-Me, 7-Me, 1-Me benzimidazol-2-yl | O | 1 | H |

TABLE 3-continued

| Compound No. | X | Y | m | R |
|---|---|---|---|---|
| 3-100 | 5-F, 6-Cl, 1-Me benzimidazol-2-yl | O | 1 | H |
| 3-101 | 5-Br, 7-Me, 1-Me benzimidazol-2-yl | O | 1 | H |
| 3-102 | 6-tBu, 1-Me benzimidazol-2-yl | O | 1 | H |
| 3-103 | 5-HO, 1-Me benzimidazol-2-yl | O | 1 | H |
| 3-104 | 7-Me, 1-Me benzimidazol-2-yl | O | 1 | H |
| 3-105 | 6-Cl, 7-Cl, 1-Me benzimidazol-2-yl | O | 1 | H |
| 3-106 | 5-F, 6-F, 7-F, 1-Me benzimidazol-2-yl | O | 1 | H |
| 3-107 | 5-Br, 6-BzO, 1-Me benzimidazol-2-yl | O | 1 | H |
| 3-108 | 7-Cl, 1-Me benzimidazol-2-yl | O | 1 | H |
| 3-109 | 5-Me, 6-HO, 7-Me, 1-Me benzimidazol-2-yl | O | 1 | H |

TABLE 3-continued

| Compound No. | X | Y | m | R |
|---|---|---|---|---|
| 3-110 | 5,6-dimethyl-4-methyl-7-hydroxy-benzimidazol-2-yl (N-Me) | O | 2 | H |
| 3-111 | 5,6-dimethyl-4-methyl-7-hydroxy-benzimidazol-2-yl (N-Me) | O | 3 | H |
| 3-112 | 5,6-dimethyl-4-methyl-7-hydroxy-benzimidazol-2-yl (N-Me) | S | 1 | H |
| 3-113 | 5,6-dimethyl-4-methyl-7-hydroxy-benzimidazol-2-yl (N-Me) | O | 1 | Me |
| 3-114 | 5,6-dimethyl-4-methyl-7-hydroxy-benzimidazol-2-yl (N-Me) | O | 1 | MeO |
| 3-115 | 5,6-dimethyl-4-methyl-7-hydroxy-benzimidazol-2-yl (N-Me) | O | 1 | Cl |
| 3-116 | benzimidazol-5-yl (N-H) | O | 1 | H |
| 3-117 | benzimidazol-5-yl (N-H) | S | 1 | H |
| 3-118 | benzimidazol-5-yl (N-Me) | O | 1 | H |
| 3-119 | benzimidazol-5-yl (N-Me) | O | 2 | H |
| 3-120 | benzimidazol-5-yl (N-Me) | O | 3 | H |
| 3-121 | benzimidazol-5-yl (N-Me) | O | 4 | H |
| 3-122 | benzimidazol-5-yl (N-Me) | O | 5 | H |
| 3-123 | benzimidazol-5-yl (N-Me) | O | 1 | MeO |
| 3-124 | benzimidazol-5-yl (N-Me) | O | 1 | Cl |
| 3-125 | benzimidazol-5-yl (N-Me) | S | 1 | H |
| 3-126 | benzimidazol-5-yl (N-Me) | S | 3 | H |
| 3-127 | benzimidazol-5-yl (N-Et) | O | 1 | H |
| 3-128 | benzimidazol-5-yl (N-Et) | S | 1 | H |
| 3-129 | benzimidazol-5-yl (N-Pr) | O | 1 | H |
| 3-130 | benzimidazol-5-yl (N-Pr) | O | 1 | Cl |

TABLE 3-continued

| Compound No. | X | Y | m | R |
|---|---|---|---|---|
| 3-131 | benzimidazole-N-iPr | O | 1 | H |
| 3-132 | benzimidazole-N-iPr | S | 1 | H |
| 3-133 | benzimidazole-N-Bu | O | 1 | H |
| 3-134 | benzimidazole-N-Bz | O | 1 | H |
| 3-135 | benzimidazole-N-Bz | O | 3 | H |
| 3-136 | benzimidazole-N-Bz | S | 1 | H |
| 3-137 | benzimidazole-N-Me | O | 1 | H |
| 3-138 | benzimidazole-N-Et | O | 1 | H |
| 3-139 | benzimidazole-N-Bz | O | 1 | H |
| 3-140 | benzimidazole-N-Bz | S | 1 | H |
| 3-141 | benzimidazole-N | O | 1 | H |
| 3-142 | benzimidazole-N-Me | O | 1 | H |
| 3-143 | benzimidazole-N-Me | O | 1 | H |
| 3-144 | 2-Me-benzimidazole-N-Me | O | 1 | H |
| 3-145 | 2-Me-benzimidazole-N-Me | S | 1 | H |
| 3-146 | MeO-benzimidazole-N-Me | O | 1 | H |
| 3-147 | MeO-benzimidazole-N-Me | O | 2 | H |
| 3-148 | MeO-benzimidazole-N-Me | O | 3 | H |
| 3-149 | MeO-benzimidazole-N-Me | O | 4 | H |
| 3-150 | MeO-benzimidazole-N-Me | O | 5 | H |
| 3-151 | MeO-benzimidazole-N-Me | S | 1 | H |

TABLE 3-continued

| Compound No. | X | Y | m | R |
|---|---|---|---|---|
| 3-152 | MeO-benzimidazole, N-Me | S | 2 | H |
| 3-153 | MeO-benzimidazole, N-Me | O | 1 | Me |
| 3-154 | MeO-benzimidazole, N-Me | O | 2 | Me |
| 3-155 | MeO-benzimidazole, N-Me | O | 1 | F |
| 3-156 | MeO-benzimidazole, N-Me | O | 1 | Cl |
| 3-157 | MeO-benzimidazole, N-Et | O | 1 | H |
| 3-158 | MeO-benzimidazole, N-Et | O | 2 | H |
| 3-159 | MeO-benzimidazole, N-Et | O | 1 | MeO |
| 3-160 | MeO-benzimidazole, N-Et | S | 1 | H |
| 3-161 | MeO-benzimidazole, N-Pr | O | 1 | H |
| 3-162 | MeO-benzimidazole, N-Pr | S | 1 | H |
| 3-163 | MeO-benzimidazole, N-iPr | O | 1 | H |
| 3-164 | MeO-benzimidazole, N-iBu | O | 1 | H |
| 3-165 | MeO-benzimidazole, N-iBu | S | 1 | H |
| 3-166 | EtO-benzimidazole, N-Me | O | 1 | H |
| 3-167 | EtO-benzimidazole, N-Me | O | 1 | MeO |
| 3-168 | EtO-benzimidazole, N-Me | O | 1 | Cl |
| 3-169 | EtO-benzimidazole, N-Me | O | 2 | H |
| 3-170 | EtO-benzimidazole, N-Me | O | 3 | H |
| 3-171 | EtO-benzimidazole, N-Me | S | 1 | H |

TABLE 3-continued

| Compound No. | X | Y | m | R |
|---|---|---|---|---|
| 3-172 | 1-Me, 5-EtO benzimidazol-2-yl | S | 4 | Et |
| 3-173 | 1-Me, 5-PrO benzimidazol-2-yl | O | 1 | H |
| 3-174 | 1-Me, 5-PrO benzimidazol-2-yl | S | 1 | H |
| 3-175 | 1-Me, 5-iPrO benzimidazol-2-yl | O | 1 | H |
| 3-176 | 1-Me, 5-iPrO benzimidazol-2-yl | O | 3 | H |
| 3-177 | 1-Me, 5-BuO benzimidazol-2-yl | O | 1 | H |
| 3-178 | 1-Me, 5-iBuO benzimidazol-2-yl | O | 1 | H |
| 3-179 | 1-Me, 5-sBuO benzimidazol-2-yl | O | 1 | H |
| 3-180 | 1-Me, 5-tBuO benzimidazol-2-yl | O | 1 | H |
| 3-181 | 1-Pr, 5-BuO benzimidazol-2-yl | O | 1 | H |
| 3-182 | 1-Me, 5-BzO benzimidazol-2-yl | O | 1 | H |
| 3-183 | 1-Me, 5-MeO, 6-Me benzimidazol-2-yl | O | 1 | H |
| 3-184 | 1-Me, 5-MeO, 6-Br benzimidazol-2-yl | O | 1 | H |
| 3-185 | 1-Me, 5-EtO, 6-F benzimidazol-2-yl | O | 1 | H |
| 3-186 | 1-Me, 4,6-F₂ benzimidazol-2-yl | O | 1 | H |
| 3-187 | 1-Me, 5-F benzimidazol-2-yl | O | 1 | H |
| 3-188 | 1-Me, 5-Cl, 6-Me benzimidazol-2-yl | O | 1 | H |
| 3-189 | 1-Et, 5-Cl, 6-Et benzimidazol-2-yl | O | 1 | H |
| 3-190 | 1-Me, 6-Et benzimidazol-2-yl | O | 1 | H |
| 3-191 | 1-Me, 5-Br benzimidazol-2-yl | O | 1 | H |

TABLE 3-continued

| Compound No. | X | Y | m | R |
|---|---|---|---|---|
| 3-192 | 1-Me, 6-CF₃, 4-Br benzimidazol-2-yl | O | 1 | H |
| 3-193 | 1-Me, 6-CF₃, 4-Cl benzimidazol-2-yl | O | 1 | H |
| 3-194 | 1-Me, 4-CF₃ benzimidazol-2-yl | O | 1 | H |
| 3-195 | 1-Me, 6-CF₃ benzimidazol-2-yl | O | 1 | H |
| 3-196 | 1-Me, 4-Me, 5-Me, 6-Br benzimidazol-2-yl | O | 1 | H |
| 3-197 | 1-Me, 5-F, 6-Cl benzimidazol-2-yl | O | 1 | H |
| 3-198 | 1-Me, 3-Me, 5-Br benzimidazol-2-yl | O | 2 | H |
| 3-199 | 1-Me, 6-tBu benzimidazol-2-yl | O | 1 | H |
| 3-200 | 1-Me, 6-HO benzimidazol-2-yl | O | 1 | H |
| 3-201 | 1-Me, 4-Me benzimidazol-2-yl | O | 1 | H |
| 3-202 | 1-Me, 5-Cl, 6-Cl benzimidazol-2-yl | O | 1 | H |
| 3-203 | 1-Me, 4-F, 5-F, 6-F benzimidazol-2-yl | O | 1 | H |
| 3-204 | 1-Me, 5-BzO, 6-Br benzimidazol-2-yl | O | 1 | H |
| 3-205 | 1-Me, 4-Cl benzimidazol-2-yl | O | 1 | H |
| 3-206 | 1-Me, 4-Me, 5-HO, 6-Me benzimidazol-2-yl | O | 1 | H |
| 3-207 | 1-Me, 4-Me, 5-HO, 6-Me benzimidazol-2-yl | O | 2 | H |
| 3-208 | 1-Me, 4-Me, 5-HO, 6-Me benzimidazol-2-yl | O | 3 | H |
| 3-209 | 1-Me, 4-Me, 5-HO, 6-Me benzimidazol-2-yl | S | 1 | H |

TABLE 3-continued

| Compound No. | X | Y | m | R |
|---|---|---|---|---|
| 3-210 | 1,4,6-trimethyl-5-hydroxy-benzimidazol-2-yl | O | 1 | Me |
| 3-211 | 1,4,6-trimethyl-5-hydroxy-benzimidazol-2-yl | O | 1 | MeO |
| 3-212 | 1,4,6-trimethyl-5-hydroxy-benzimidazol-2-yl | O | 1 | Cl |
| 3-213 | 1-methylbenzimidazol-5-yl | O | 1 | H |
| 3-214 | 1-methylbenzimidazol-5-yl | O | 2 | H |
| 3-215 | 1-methylbenzimidazol-5-yl | O | 3 | H |
| 3-216 | 1-methylbenzimidazol-5-yl | O | 4 | H |
| 3-217 | 1-methylbenzimidazol-5-yl | O | 5 | H |
| 3-218 | 1-methylbenzimidazol-5-yl | O | 1 | MeO |
| 3-219 | 1-methylbenzimidazol-5-yl | O | 1 | Cl |
| 3-220 | 1-methylbenzimidazol-5-yl | S | 1 | H |
| 3-221 | 1-methylbenzimidazol-5-yl | S | 3 | H |
| 3-222 | 1-ethylbenzimidazol-5-yl | O | 1 | H |
| 3-223 | 1-ethylbenzimidazol-5-yl | S | 1 | H |
| 3-224 | 1-propylbenzimidazol-5-yl | O | 1 | H |
| 3-225 | 1-propylbenzimidazol-5-yl | O | 1 | Cl |
| 3-226 | 1-isopropylbenzimidazol-5-yl | O | 1 | H |
| 3-227 | 1-isopropylbenzimidazol-5-yl | S | 1 | H |
| 3-228 | 1-butylbenzimidazol-5-yl | O | 1 | H |
| 3-229 | 1-benzylbenzimidazol-5-yl | O | 1 | H |
| 3-230 | 1-benzylbenzimidazol-5-yl | O | 3 | H |

TABLE 3-continued

| Compound No. | X | Y | m | R |
|---|---|---|---|---|
| 3-231 | benzimidazole N-Bz | S | 1 | H |
| 3-232 | benzimidazole N-Me | O | 1 | H |
| 3-233 | benzimidazole N-Et | O | 1 | H |
| 3-234 | benzimidazole N-Bz | O | 1 | H |
| 3-235 | benzimidazole N-Bz | S | 1 | H |
| 3-236 | 1-Me, 2-Me benzimidazole | O | 1 | H |

TABLE 4

| Compound No. | X | Y | m | R |
|---|---|---|---|---|
| 4-1 | 2-benzimidazolyl (NH) | O | 1 | H |
| 4-2 | 2-benzimidazolyl (NH) | O | 2 | H |
| 4-3 | 2-benzimidazolyl (NH) | O | 3 | H |
| 4-4 | 2-benzimidazolyl (NH) | O | 4 | H |
| 4-5 | 2-benzimidazolyl (NH) | O | 5 | MeO |
| 4-6 | 2-benzimidazolyl (NH) | S | 1 | H |
| 4-7 | 2-benzimidazolyl (NH) | O | 1 | MeO |
| 4-8 | 2-benzimidazolyl (NH) | O | 1 | Cl |
| 4-9 | 2-benzimidazolyl (NH) | O | 1 | Me |
| 4-10 | 2-benzimidazolyl (NH) | S | 1 | MeO |
| 4-11 | 2-benzimidazolyl (N-Me) | O | 1 | H |
| 4-12 | 2-benzimidazolyl (N-Me) | O | 2 | H |
| 4-13 | 2-benzimidazolyl (N-Me) | O | 3 | H |
| 4-14 | 2-benzimidazolyl (N-Me) | O | 4 | H |

TABLE 4-continued
| Compound No. | X | Y | m | R |
|---|---|---|---|---|
| 4-15 | 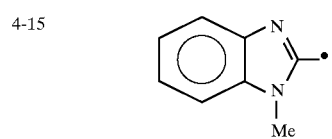 | O | 5 | H |
| 4-16 | 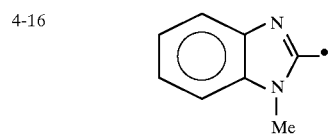 | S | 1 | H |
| 4-17 | 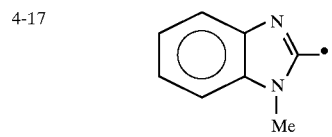 | S | 2 | H |
| 4-18 | 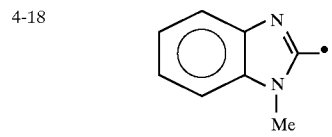 | O | 1 | MeO |
| 4-19 | 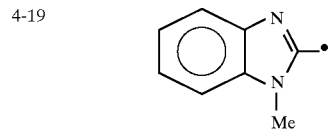 | O | 1 | EtO |
| 4-20 | 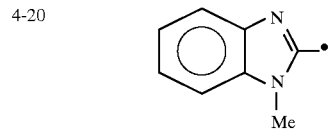 | O | 1 | Cl |
| 4-21 | 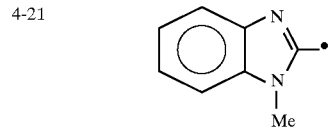 | O | 1 | F |
| 4-22 | 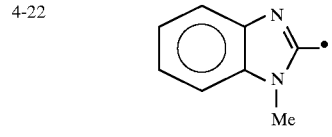 | O | 1 | Me |
| 4-23 | 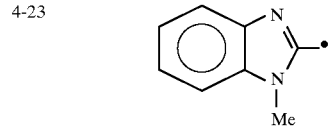 | O | 1 | iPr |
| 4-24 | 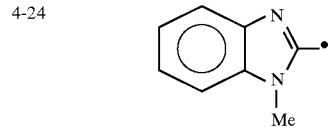 | O | 2 | Et |
| 4-25 | 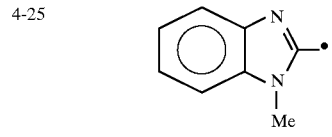 | S | 1 | Cl |
TABLE 4-continued
| Compound No. | X | Y | m | R |
|---|---|---|---|---|
| 4-26 | 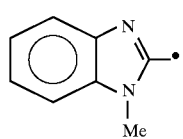 | S | 1 | Me |
| 4-27 | 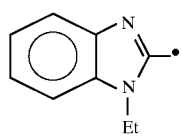 | O | 1 | H |
| 4-28 | 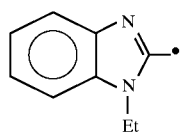 | O | 2 | H |
| 4-29 | 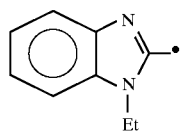 | O | 3 | tBu |
| 4-30 | 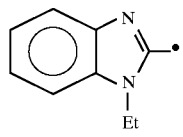 | O | 1 | Me |
| 4-31 | 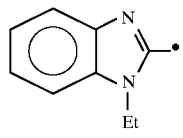 | O | 1 | MeO |
| 4-32 | 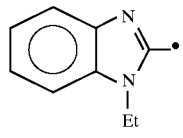 | S | 1 | H |
| 4-33 | 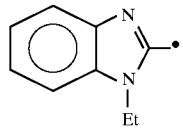 | S | 1 | PrO |
| 4-34 | 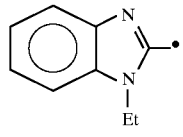 | S | 1 | Me |
| 4-35 | 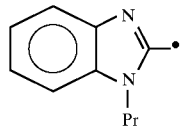 | O | 1 | H |
| 4-36 | 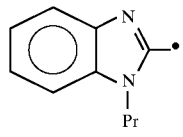 | O | 3 | H |

TABLE 4-continued
| Compound No. | X | Y | m | R |
|---|---|---|---|---|
| 4-37 | 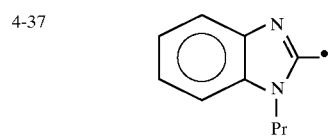 | O | 1 | F |
| 4-38 | 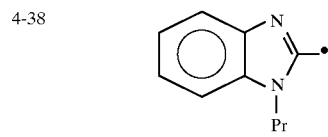 | S | 1 | H |
| 4-39 | 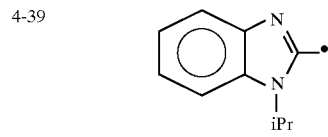 | O | 1 | H |
| 4-40 | 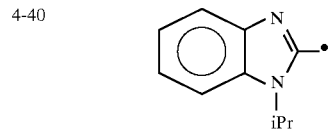 | O | 2 | H |
| 4-41 | 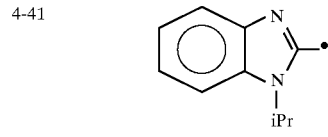 | S | 1 | H |
| 4-42 | 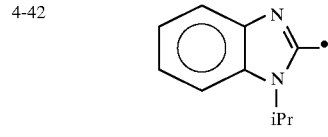 | S | 5 | Cl |
| 4-43 | 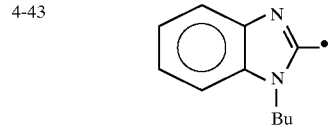 | O | 1 | H |
| 4-44 | 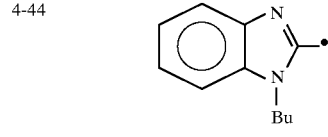 | O | 4 | H |
| 4-45 | 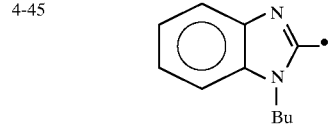 | S | 1 | H |
| 4-46 | 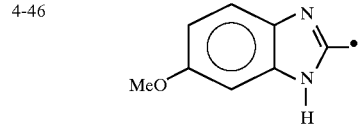 | O | 1 | H |
| 4-47 | 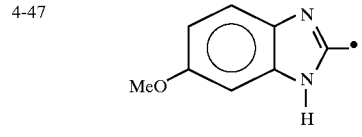 | O | 3 | H |
TABLE 4-continued
| Compound No. | X | Y | m | R |
|---|---|---|---|---|
| 4-48 | 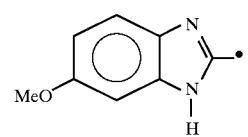 | S | 1 | H |
| 4-49 | 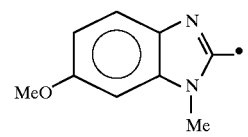 | O | 1 | H |
| 4-50 | 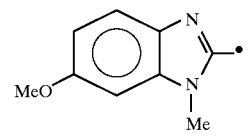 | O | 2 | H |
| 4-51 | 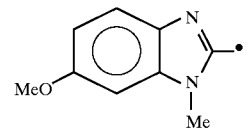 | O | 3 | H |
| 4-52 | 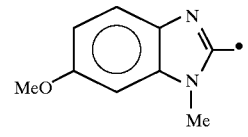 | O | 4 | H |
| 4-53 | 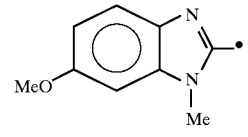 | O | 5 | H |
| 4-54 | 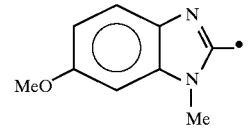 | S | 1 | H |
| 4-55 | 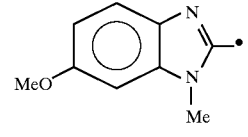 | S | 2 | H |
| 4-56 | 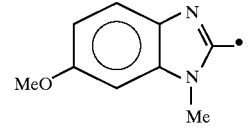 | O | 1 | Me |
| 4-57 | 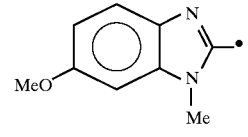 | O | 1 | MeO |
| 4-58 | 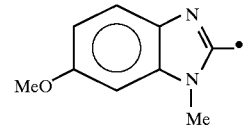 | O | 1 | F |

TABLE 4-continued
| Compound No. | X | Y | m | R |
|---|---|---|---|---|
| 4-59 | 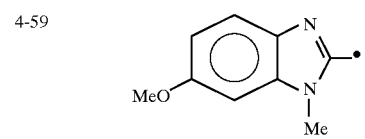 | O | 1 | Cl |
| 4-60 | 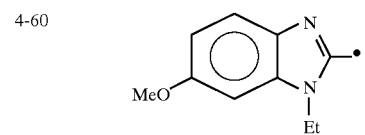 | O | 1 | H |
| 4-61 | 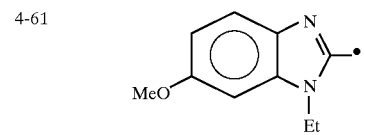 | O | 2 | H |
| 4-62 | 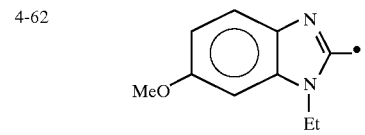 | O | 1 | MeO |
| 4-63 | 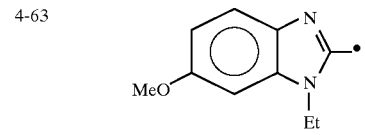 | S | 1 | H |
| 4-64 | 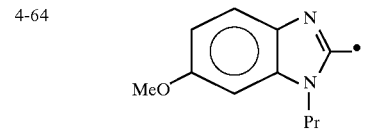 | O | 1 | H |
| 4-65 | 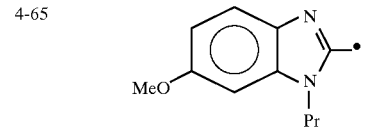 | S | 1 | H |
| 4-66 | 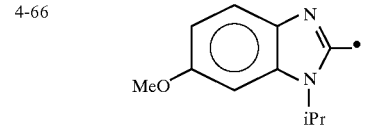 | O | 1 | H |
| 4-67 | 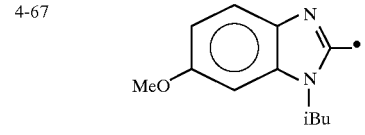 | O | 1 | H |
| 4-68 | 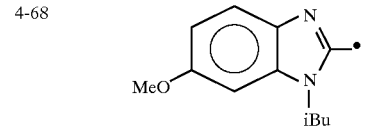 | S | 1 | H |
| 4-69 | 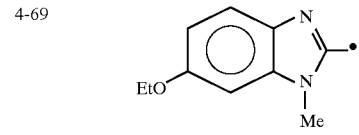 | O | 1 | H |
TABLE 4-continued
| Compound No. | X | Y | m | R |
|---|---|---|---|---|
| 4-70 | 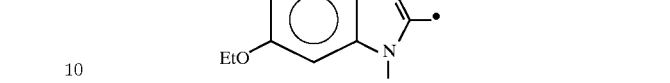 | O | 1 | MeO |
| 4-71 | 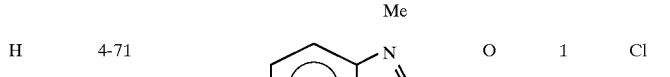 | O | 1 | Cl |
| 4-72 | 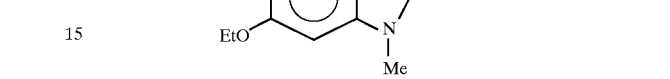 | O | 2 | H |
| 4-73 | 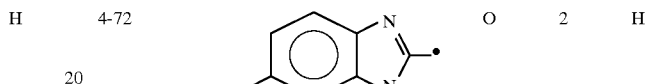 | O | 3 | H |
| 4-74 | 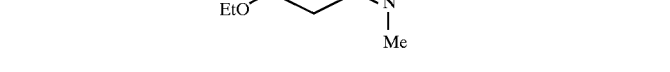 | S | 1 | H |
| 4-75 |  | S | 4 | Et |
| 4-76 | 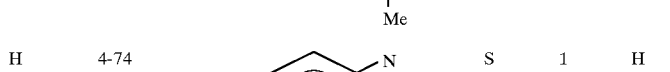 | O | 1 | H |
| 4-77 | 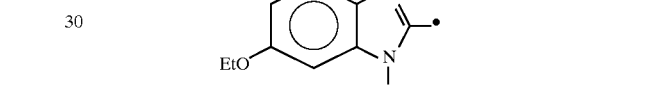 | S | 1 | H |
| 4-78 | 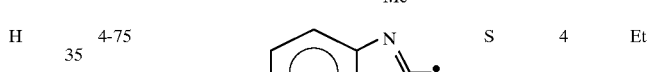 | O | 1 | H |
| 4-79 | 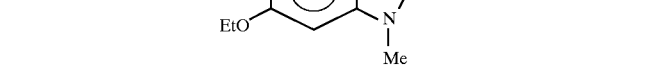 | O | 3 | H |
| 4-80 | 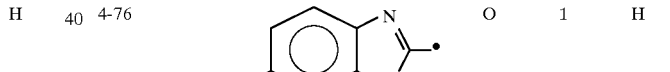 | O | 1 | H |

TABLE 4-continued

| Compound No. | X | Y | m | R |
|---|---|---|---|---|
| 4-81 | 6-iBuO, 1-Me-benzimidazol-2-yl | O | 1 | H |
| 4-82 | 6-sBuO, 1-Me-benzimidazol-2-yl | O | 1 | H |
| 4-83 | 6-tBuO, 1-Me-benzimidazol-2-yl | O | 1 | H |
| 4-84 | 6-BuO, 1-Pr-benzimidazol-2-yl | O | 1 | H |
| 4-85 | 6-BzO, 1-Me-benzimidazol-2-yl | O | 1 | H |
| 4-86 | 5-MeO, 6-Me, 1-Me-benzimidazol-2-yl | O | 1 | H |
| 4-87 | 5-MeO, 6-Br, 1-Me-benzimidazol-2-yl | O | 1 | H |
| 4-88 | 5-EtO, 6-F, 1-Me-benzimidazol-2-yl | O | 1 | H |
| 4-89 | 5,7-diF, 1-Me-benzimidazol-2-yl | O | 1 | H |
| 4-90 | 6-F, 1-Me-benzimidazol-2-yl | O | 1 | H |
| 4-91 | 5-Cl, 6-Me, 1-Me-benzimidazol-2-yl | O | 1 | H |
| 4-92 | 5-Cl, 6-Et, 1-Et-benzimidazol-2-yl | O | 1 | H |
| 4-93 | 5-Et, 1-Me-benzimidazol-2-yl | O | 1 | H |
| 4-94 | 6-Br, benzimidazol-2-yl | O | 1 | H |
| 4-95 | 5-CF$_3$, 7-Br, 1-Me-benzimidazol-2-yl | O | 1 | H |
| 4-96 | 5-CF$_3$, 7-Cl, 1-Me-benzimidazol-2-yl | O | 1 | H |
| 4-97 | 7-CF$_3$, 1-Me-benzimidazol-2-yl | O | 1 | H |
| 4-98 | 6-CF$_3$, 1-Me-benzimidazol-2-yl | O | 1 | H |
| 4-99 | 5-Br, 6-Me, 7-Me, 1-Me-benzimidazol-2-yl | O | 1 | H |
| 4-100 | 5-F, 6-Cl, 1-Me-benzimidazol-2-yl | O | 1 | H |

TABLE 4-continued
| Compound No. | X | Y | m | R |
|---|---|---|---|---|
| 4-101 | 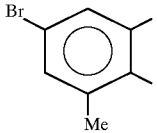 | O | 1 | H |
| 4-102 | 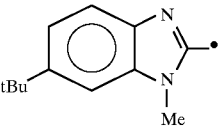 | O | 1 | H |
| 4-103 | 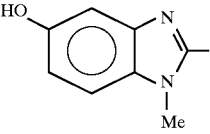 | O | 1 | H |
| 4-104 | 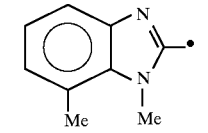 | O | 1 | H |
| 4-105 | 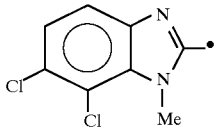 | O | 1 | H |
| 4-106 | 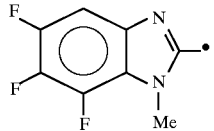 | O | 1 | H |
| 4-107 | 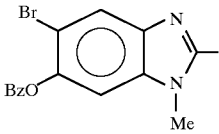 | O | 1 | H |
| 4-108 | 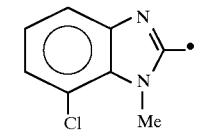 | O | 1 | H |
| 4-109 | 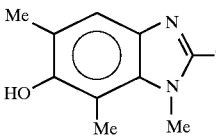 | O | 1 | H |
| 4-110 | 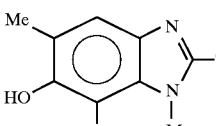 | O | 2 | H |
| 4-111 | 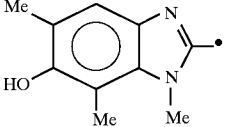 | O | 3 | H |
| 4-112 | 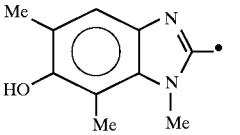 | S | 1 | H |
| 4-113 | 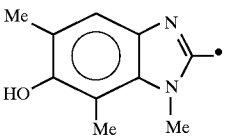 | O | 1 | Me |
| 4-114 | 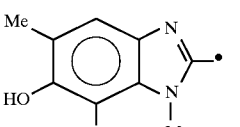 | O | 1 | MeO |
| 4-115 | 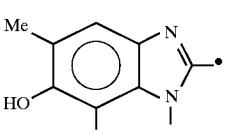 | O | 1 | Cl |
| 4-116 | 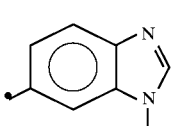 | O | 1 | H |
| 4-117 | 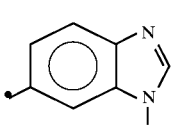 | S | 1 | H |
| 4-118 | 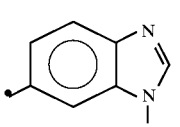 | O | 1 | H |
| 4-119 | 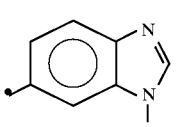 | O | 2 | H |
| 4-120 | 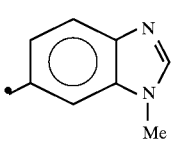 | O | 3 | H |

TABLE 4-continued

| Compound No. | X | Y | m | R |
|---|---|---|---|---|
| 4-121 | benzimidazole-N-Me | O | 4 | H |
| 4-122 | benzimidazole-N-Me | O | 5 | H |
| 4-123 | benzimidazole-N-Me | O | 1 | MeO |
| 4-124 | benzimidazole-N-Me | O | 1 | Cl |
| 4-125 | benzimidazole-N-Me | S | 1 | H |
| 4-126 | benzimidazole-N-Me | S | 3 | H |
| 4-127 | benzimidazole-N-Et | O | 1 | H |
| 4-128 | benzimidazole-N-Et | S | 1 | H |
| 4-129 | benzimidazole-N-Pr | O | 1 | H |
| 4-130 | benzimidazole-N-Pr | O | 1 | Cl |
| 4-131 | benzimidazole-N-iPr | O | 1 | H |
| 4-132 | benzimidazole-N-iPr | S | 1 | H |
| 4-133 | benzimidazole-N-Bu | O | 1 | H |
| 4-134 | benzimidazole-N-Bz | O | 1 | H |
| 4-135 | benzimidazole-N-Bz | O | 3 | H |
| 4-136 | benzimidazole-N-Bz | S | 1 | H |
| 4-137 | benzimidazole-N-Me (alt) | O | 1 | H |
| 4-138 | benzimidazole-N-Et (alt) | O | 1 | H |
| 4-139 | benzimidazole-N-Bz (alt) | O | 1 | H |
| 4-140 | benzimidazole-N-Bz (alt) | S | 1 | H |
| 4-141 | benzimidazole (alt) | O | 1 | H |
| 4-142 | benzimidazole-N-Me (alt) | O | 1 | H |

TABLE 4-continued

| Compound No. | X | Y | m | R |
|---|---|---|---|---|
| 4-143 | benzimidazole (N-Me) | O | 1 | H |
| 4-144 | 2-Me, N-Me benzimidazole | O | 1 | H |
| 4-145 | 2-Me, N-Me benzimidazole | S | 1 | H |
| 4-146 | 1-Me, 5-MeO benzimidazole | O | 1 | H |
| 4-147 | 1-Me, 5-MeO benzimidazole | O | 2 | H |
| 4-148 | 1-Me, 5-MeO benzimidazole | O | 3 | H |
| 4-149 | 1-Me, 5-MeO benzimidazole | O | 4 | H |
| 4-150 | 1-Me, 5-MeO benzimidazole | O | 5 | H |
| 4-151 | 1-Me, 5-MeO benzimidazole | S | 1 | H |
| 4-152 | 1-Me, 5-MeO benzimidazole | S | 2 | H |
| 4-153 | 1-Me, 5-MeO benzimidazole | O | 1 | Me |
| 4-154 | 1-Me, 5-MeO benzimidazole | O | 2 | Me |
| 4-155 | 1-Me, 5-MeO benzimidazole | O | 1 | F |
| 4-156 | 1-Me, 5-MeO benzimidazole | O | 1 | Cl |
| 4-157 | 1-Et, 5-MeO benzimidazole | O | 1 | H |
| 4-158 | 1-Et, 5-MeO benzimidazole | O | 2 | H |
| 4-159 | 1-Et, 5-MeO benzimidazole | O | 1 | MeO |
| 4-160 | 1-Et, 5-MeO benzimidazole | S | 1 | H |
| 4-161 | 1-Pr, 5-MeO benzimidazole | O | 1 | H |
| 4-162 | 1-Pr, 5-MeO benzimidazole | S | 1 | H |

TABLE 4-continued

| Compound No. | X | Y | m | R |
|---|---|---|---|---|
| 4-163 | 1-iPr, 5-MeO benzimidazol-2-yl | O | 1 | H |
| 4-164 | 1-iBu, 5-MeO benzimidazol-2-yl | O | 1 | H |
| 4-165 | 1-iBu, 5-MeO benzimidazol-2-yl | S | 1 | H |
| 4-166 | 1-Me, 5-EtO benzimidazol-2-yl | O | 1 | H |
| 4-167 | 1-Me, 5-EtO benzimidazol-2-yl | O | 1 | MeO |
| 4-168 | 1-Me, 5-EtO benzimidazol-2-yl | O | 1 | Cl |
| 4-169 | 1-Me, 5-EtO benzimidazol-2-yl | O | 2 | H |
| 4-170 | 1-Me, 5-EtO benzimidazol-2-yl | O | 3 | H |
| 4-171 | 1-Me, 5-EtO benzimidazol-2-yl | S | 1 | H |
| 4-172 | 1-Me, 5-EtO benzimidazol-2-yl | S | 4 | Et |
| 4-173 | 1-Me, 5-PrO benzimidazol-2-yl | O | 1 | H |
| 4-174 | 1-Me, 5-PrO benzimidazol-2-yl | S | 1 | H |
| 4-175 | 1-Me, 5-iPrO benzimidazol-2-yl | O | 1 | H |
| 4-176 | 1-Me, 5-iPrO benzimidazol-2-yl | O | 3 | H |
| 4-177 | 1-Me, 5-BuO benzimidazol-2-yl | O | 1 | H |
| 4-178 | 1-Me, 5-iBuO benzimidazol-2-yl | O | 1 | H |
| 4-179 | 1-Me, 5-sBuO benzimidazol-2-yl | O | 1 | H |
| 4-180 | 1-Me, 5-tBuO benzimidazol-2-yl | O | 1 | H |
| 4-181 | 1-Pr, 5-BuO benzimidazol-2-yl | O | 1 | H |
| 4-182 | 1-Me, 5-BzO benzimidazol-2-yl | O | 1 | H |

TABLE 4-continued

| Compound No. | X | Y | m | R |
|---|---|---|---|---|
| 4-183 | MeO-, Me- benzimidazole (N-Me) | O | 1 | H |
| 4-184 | MeO-, Br- benzimidazole (N-Me) | O | 1 | H |
| 4-185 | EtO-, F- benzimidazole (N-Me) | O | 1 | H |
| 4-186 | F-, F- benzimidazole (N-Me) | O | 1 | H |
| 4-187 | F- benzimidazole (N-Me) | O | 1 | H |
| 4-188 | Cl-, Me- benzimidazole (N-Me) | O | 1 | H |
| 4-189 | Cl-, Et- benzimidazole (N-Et) | O | 1 | H |
| 4-190 | Et- benzimidazole (N-Me) | O | 1 | H |
| 4-191 | Br- benzimidazole (N-Me) | O | 1 | H |
| 4-192 | CF₃-, Br- benzimidazole (N-Me) | O | 1 | H |
| 4-193 | CF₃-, Cl- benzimidazole (N-Me) | O | 1 | H |
| 4-194 | CF₃- benzimidazole (N-Me) | O | 1 | H |
| 4-195 | CF₃- benzimidazole (N-Me) | O | 1 | H |
| 4-196 | Br-, Me-, Me- benzimidazole (N-Me) | O | 1 | H |
| 4-197 | F-, Cl- benzimidazole (N-Me) | O | 1 | H |
| 4-198 | Br-, Me- benzimidazole (N-Me) | O | 2 | H |
| 4-199 | tBu- benzimidazole (N-Me) | O | 1 | H |
| 4-200 | HO- benzimidazole (N-Me) | O | 1 | H |
| 4-201 | Me- benzimidazole (N-Me) | O | 1 | H |

TABLE 4-continued

| Compound No. | X | Y | m | R |
|---|---|---|---|---|
| 4-202 | 4,5-dichloro-1-methylbenzimidazol-2-yl | O | 1 | H |
| 4-203 | 4,5,6-trifluoro-1-methylbenzimidazol-2-yl | O | 1 | H |
| 4-204 | 5-bromo-6-benzoyloxy-1-methylbenzimidazol-2-yl | O | 1 | H |
| 4-205 | 4-chloro-1-methylbenzimidazol-2-yl | O | 1 | H |
| 4-206 | 4,6-dimethyl-5-hydroxy-1-methylbenzimidazol-2-yl | O | 1 | H |
| 4-207 | 4,6-dimethyl-5-hydroxy-1-methylbenzimidazol-2-yl | O | 2 | H |
| 4-208 | 4,6-dimethyl-5-hydroxy-1-methylbenzimidazol-2-yl | O | 3 | H |
| 4-209 | 4,6-dimethyl-5-hydroxy-1-methylbenzimidazol-2-yl | S | 1 | H |
| 4-210 | 4,6-dimethyl-5-hydroxy-1-methylbenzimidazol-2-yl | O | 1 | Me |
| 4-211 | 4,6-dimethyl-5-hydroxy-1-methylbenzimidazol-2-yl | O | 1 | MeO |
| 4-212 | 4,6-dimethyl-5-hydroxy-1-methylbenzimidazol-2-yl | O | 1 | Cl |
| 4-213 | 1-methylbenzimidazol-5-yl | O | 1 | H |
| 4-214 | 1-methylbenzimidazol-5-yl | O | 2 | H |
| 4-215 | 1-methylbenzimidazol-5-yl | O | 3 | H |
| 4-216 | 1-methylbenzimidazol-5-yl | O | 4 | H |
| 4-217 | 1-methylbenzimidazol-5-yl | O | 5 | H |
| 4-218 | 1-methylbenzimidazol-5-yl | O | 1 | MeO |
| 4-219 | 1-methylbenzimidazol-5-yl | O | 1 | Cl |
| 4-220 | 1-methylbenzimidazol-5-yl | S | 1 | H |

TABLE 4-continued

| Compound No. | X | Y | m | R |
|---|---|---|---|---|
| 4-221 | 6-(1-Me-benzimidazolyl) | S | 3 | H |
| 4-222 | 6-(1-Et-benzimidazolyl) | O | 1 | H |
| 4-223 | 6-(1-Et-benzimidazolyl) | S | 1 | H |
| 4-224 | 6-(1-Pr-benzimidazolyl) | O | 1 | H |
| 4-225 | 6-(1-Pr-benzimidazolyl) | O | 1 | Cl |
| 4-226 | 6-(1-iPr-benzimidazolyl) | O | 1 | H |
| 4-227 | 6-(1-iPr-benzimidazolyl) | S | 1 | H |
| 4-228 | 6-(1-Bu-benzimidazolyl) | O | 1 | H |
| 4-229 | 6-(1-Bz-benzimidazolyl) | O | 1 | H |
| 4-230 | 6-(1-Bz-benzimidazolyl) | O | 3 | H |
| 4-231 | 6-(1-Bz-benzimidazolyl) | S | 1 | H |

TABLE 4-continued

| Compound No. | X | Y | m | R |
|---|---|---|---|---|
| 4-232 | 4-(1-Me-benzimidazolyl) | O | 1 | H |
| 4-233 | 4-(1-Et-benzimidazolyl) | O | 1 | H |
| 4-234 | 4-(1-Bz-benzimidazolyl) | O | 1 | H |
| 4-235 | 4-(1-Bz-benzimidazolyl) | S | 1 | H |
| 4-236 | 6-(1,2-diMe-benzimidazolyl) | O | 1 | H |

TABLE 5

| Compound No. | X | Y | m | R |
|---|---|---|---|---|
| 5-1 | 2-benzimidazolyl (NH) | O | 1 | H |
| 5-2 | 2-benzimidazolyl (NH) | O | 2 | H |
| 5-3 | 2-benzimidazolyl (NH) | O | 3 | H |
| 5-4 | 2-benzimidazolyl (NH) | O | 4 | H |

TABLE 5-continued

| Compound No. | X | Y | m | R |
|---|---|---|---|---|
| 5-5 | benzimidazole-NH | O | 5 | MeO |
| 5-6 | benzimidazole-NH | S | 1 | H |
| 5-7 | benzimidazole-NH | O | 1 | MeO |
| 5-8 | benzimidazole-NH | O | 1 | Cl |
| 5-9 | benzimidazole-NH | O | 1 | Me |
| 5-10 | benzimidazole-NH | S | 1 | MeO |
| 5-11 | benzimidazole-NMe | O | 1 | H |
| 5-12 | benzimidazole-NMe | O | 2 | H |
| 5-13 | benzimidazole-NMe | O | 3 | H |
| 5-14 | benzimidazole-NMe | O | 4 | H |
| 5-15 | benzimidazole-NMe | O | 5 | H |
| 5-16 | benzimidazole-NMe | S | 1 | H |
| 5-17 | benzimidazole-NMe | S | 2 | H |
| 5-18 | benzimidazole-NMe | O | 1 | MeO |
| 5-19 | benzimidazole-NMe | O | 1 | EtO |
| 5-20 | benzimidazole-NMe | O | 1 | Cl |
| 5-21 | benzimidazole-NMe | O | 1 | F |
| 5-22 | benzimidazole-NMe | O | 1 | Me |
| 5-23 | benzimidazole-NMe | O | 1 | iPr |
| 5-24 | benzimidazole-NMe | O | 2 | Et |
| 5-25 | benzimidazole-NMe | S | 1 | Cl |
| 5-26 | benzimidazole-NMe | S | 1 | Me |

TABLE 5-continued
| Compound No. | X | Y | m | R |
|---|---|---|---|---|
| 5-27 | 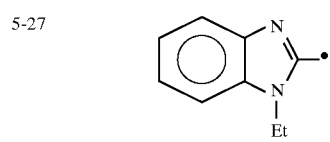 | O | 1 | H |
| 5-28 | 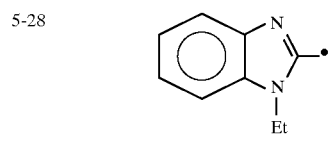 | O | 2 | H |
| 5-29 | 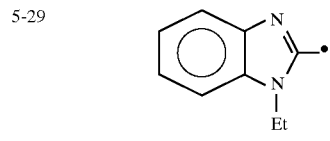 | O | 3 | tBu |
| 5-30 | 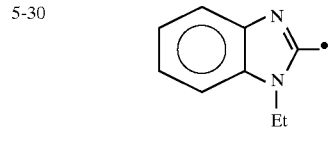 | O | 1 | Me |
| 5-31 | 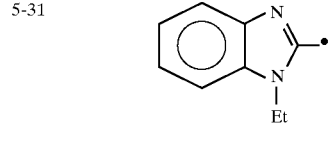 | O | 1 | MeO |
| 5-32 | 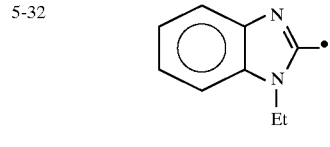 | S | 1 | H |
| 5-33 | 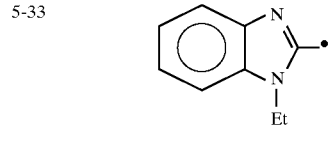 | S | 1 | PrO |
| 5-34 | 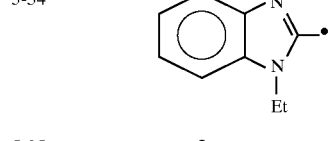 | S | 1 | Me |
| 5-35 | 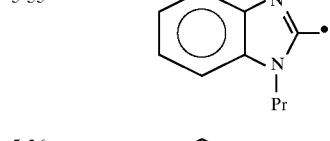 | O | 1 | H |
| 5-36 | 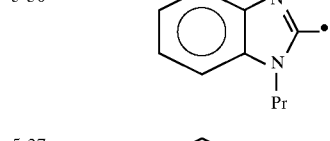 | O | 3 | H |
| 5-37 | 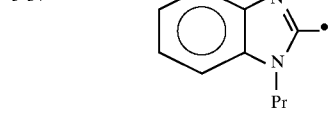 | O | 1 | F |
TABLE 5-continued
| Compound No. | X | Y | m | R |
|---|---|---|---|---|
| 5-38 | 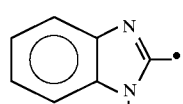 | S | 1 | H |
| 5-39 | 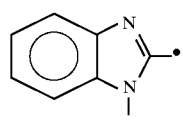 | O | 1 | H |
| 5-40 | 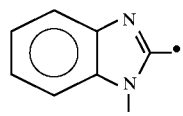 | O | 2 | H |
| 5-41 | 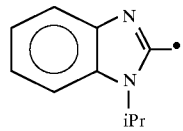 | S | 1 | H |
| 5-42 | 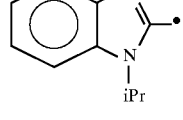 | S | 5 | Cl |
| 5-43 | 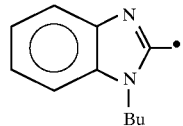 | O | 1 | H |
| 5-44 | 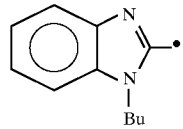 | O | 4 | H |
| 5-45 | 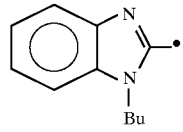 | S | 1 | H |
| 5-46 | 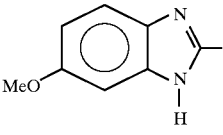 | O | 1 | H |
| 5-47 | 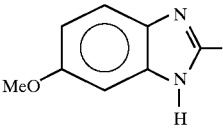 | O | 3 | H |
| 5-48 | 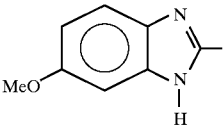 | S | 1 | H |

TABLE 5-continued

| Compound No. | X | Y | m | R |
|---|---|---|---|---|
| 5-49 | MeO-benzimidazole, N-Me | O | 1 | H |
| 5-50 | MeO-benzimidazole, N-Me | O | 2 | H |
| 5-51 | MeO-benzimidazole, N-Me | O | 3 | H |
| 5-52 | MeO-benzimidazole, N-Me | O | 4 | H |
| 5-53 | MeO-benzimidazole, N-Me | O | 5 | H |
| 5-54 | MeO-benzimidazole, N-Me | S | 1 | H |
| 5-55 | MeO-benzimidazole, N-Me | S | 2 | H |
| 5-56 | MeO-benzimidazole, N-Me | O | 1 | Me |
| 5-57 | MeO-benzimidazole, N-Me | O | 1 | MeO |
| 5-58 | MeO-benzimidazole, N-Me | O | 1 | F |
| 5-59 | MeO-benzimidazole, N-Me | O | 1 | Cl |

TABLE 5-continued

| Compound No. | X | Y | m | R |
|---|---|---|---|---|
| 5-60 | MeO-benzimidazole, N-Et | O | 1 | H |
| 5-61 | MeO-benzimidazole, N-Et | O | 2 | H |
| 5-62 | MeO-benzimidazole, N-Et | O | 1 | MeO |
| 5-63 | MeO-benzimidazole, N-Et | S | 1 | H |
| 5-64 | MeO-benzimidazole, N-Pr | O | 1 | H |
| 5-65 | MeO-benzimidazole, N-Pr | S | 1 | H |
| 5-66 | MeO-benzimidazole, N-iPr | O | 1 | H |
| 5-67 | MeO-benzimidazole, N-iBu | O | 1 | H |
| 5-68 | MeO-benzimidazole, N-iBu | S | 1 | H |
| 5-69 | EtO-benzimidazole, N-Me | O | 1 | H |
| 5-70 | EtO-benzimidazole, N-Me | O | 1 | MeO |

TABLE 5-continued

| Compound No. | X | Y | m | R |
|---|---|---|---|---|
| 5-71 | EtO-[benzimidazole]-N-Me | O | 1 | Cl |
| 5-72 | EtO-[benzimidazole]-N-Me | O | 2 | H |
| 5-73 | EtO-[benzimidazole]-N-Me | O | 3 | H |
| 5-74 | EtO-[benzimidazole]-N-Me | S | 1 | H |
| 5-75 | EtO-[benzimidazole]-N-Me | S | 4 | Et |
| 5-76 | PrO-[benzimidazole]-N-Me | O | 1 | H |
| 5-77 | PrO-[benzimidazole]-N-Me | S | 1 | H |
| 5-78 | iPrO-[benzimidazole]-N-Me | O | 1 | H |
| 5-79 | iPrO-[benzimidazole]-N-Me | O | 3 | H |
| 5-80 | BuO-[benzimidazole]-N-Me | O | 1 | H |
| 5-81 | iBuO-[benzimidazole]-N-Me | O | 1 | H |
| 5-82 | sBuO-[benzimidazole]-N-Me | O | 1 | H |
| 5-83 | tBuO-[benzimidazole]-N-Me | O | 1 | H |
| 5-84 | BuO-[benzimidazole]-N-Pr | O | 1 | H |
| 5-85 | BzO-[benzimidazole]-N-Me | O | 1 | H |
| 5-86 | MeO,Me-[benzimidazole]-N-Me | O | 1 | H |
| 5-87 | MeO,Br-[benzimidazole]-N-Me | O | 1 | H |
| 5-88 | EtO,F-[benzimidazole]-N-Me | O | 1 | H |
| 5-89 | F,F-[benzimidazole]-N-Me | O | 1 | H |
| 5-90 | F-[benzimidazole]-N-Me | O | 1 | H |
| 5-91 | Cl,Me-[benzimidazole]-N-Me | O | 1 | H |

TABLE 5-continued

| Compound No. | X | Y | m | R |
|---|---|---|---|---|
| 5-92 | 5,6-disubst benzimidazole: 5-Cl, 6-Et, N-Et | O | 1 | H |
| 5-93 | 5-Et, N-Me benzimidazole | O | 1 | H |
| 5-94 | 5-Br, N-Me benzimidazole | O | 1 | H |
| 5-95 | 5-CF3, 7-Br, N-Me benzimidazole | O | 1 | H |
| 5-96 | 5-CF3, 7-Cl, N-Me benzimidazole | O | 1 | H |
| 5-97 | 7-CF3, N-Me benzimidazole | O | 1 | H |
| 5-98 | 5-CF3, N-Me benzimidazole | O | 1 | H |
| 5-99 | 5-Br, 6-Me, 7-Me, N-Me benzimidazole | O | 1 | H |
| 5-100 | 5-F, 6-Cl, N-Me benzimidazole | O | 1 | H |
| 5-101 | 5-Br, 7-Me, N-Me benzimidazole | O | 1 | H |
| 5-102 | 5-tBu, N-Me benzimidazole | O | 1 | H |
| 5-103 | 5-OH, N-Me benzimidazole | O | 1 | H |
| 5-104 | 7-Me, N-Me benzimidazole | O | 1 | H |
| 5-105 | 5-Cl, 6-Cl, N-Me benzimidazole | O | 1 | H |
| 5-106 | 5-F, 6-F, 7-F, N-Me benzimidazole | O | 1 | H |
| 5-107 | 5-Br, 6-BzO, N-Me benzimidazole | O | 1 | H |
| 5-108 | 7-Cl, N-Me benzimidazole | O | 1 | H |
| 5-109 | 5-Me, 6-OH, 7-Me, N-Me benzimidazole | O | 1 | H |
| 5-110 | 5-Me, 6-OH, 7-Me, N-Me benzimidazole | O | 2 | H |
| 5-111 | 5-Me, 6-OH, 7-Me, N-Me benzimidazole | O | 3 | H |

TABLE 5-continued

| Compound No. | X | Y | m | R |
|---|---|---|---|---|
| 5-112 | Me, HO, Me, Me benzimidazole | S | 1 | H |
| 5-113 | Me, HO, Me, Me benzimidazole | O | 1 | Me |
| 5-114 | Me, HO, Me, Me benzimidazole | O | 1 | MeO |
| 5-115 | Me, HO, Me, Me benzimidazole | O | 1 | Cl |
| 5-116 | benzimidazole N-H | O | 1 | H |
| 5-117 | benzimidazole N-H | S | 1 | H |
| 5-118 | benzimidazole N-Me | O | 1 | H |
| 5-119 | benzimidazole N-Me | O | 2 | H |
| 5-120 | benzimidazole N-Me | O | 3 | H |
| 5-121 | benzimidazole N-Me | O | 4 | H |
| 5-122 | benzimidazole N-Me | O | 5 | H |
| 5-123 | benzimidazole N-Me | O | 1 | MeO |
| 5-124 | benzimidazole N-Me | O | 1 | Cl |
| 5-125 | benzimidazole N-Me | S | 1 | H |
| 5-126 | benzimidazole N-Me | S | 3 | H |
| 5-127 | benzimidazole N-Et | O | 1 | H |
| 5-128 | benzimidazole N-Et | S | 1 | H |
| 5-129 | benzimidazole N-Pr | O | 1 | H |
| 5-130 | benzimidazole N-Pr | O | 1 | Cl |
| 5-131 | benzimidazole N-iPr | O | 1 | H |
| 5-132 | benzimidazole N-iPr | S | 1 | H |
| 5-133 | benzimidazole N-Bu | O | 1 | H |

TABLE 5-continued

| Compound No. | X | Y | m | R |
|---|---|---|---|---|
| 5-134 | benzimidazolyl-N-Bz | O | 1 | H |
| 5-135 | benzimidazolyl-N-Bz | O | 3 | H |
| 5-136 | benzimidazolyl-N-Bz | S | 1 | H |
| 5-137 | benzimidazolyl-N-Me | O | 1 | H |
| 5-138 | benzimidazolyl-N-Et | O | 1 | H |
| 5-139 | benzimidazolyl-N-Bz | O | 1 | H |
| 5-140 | benzimidazolyl-N-Bz | S | 1 | H |
| 5-141 | benzimidazolyl-NH | O | 1 | H |
| 5-142 | benzimidazolyl-N-Me | O | 1 | H |
| 5-143 | benzimidazolyl-N-Me | O | 1 | H |
| 5-144 | 2-Me-1-Me-benzimidazolyl | O | 1 | H |
| 5-145 | 2-Me-1-Me-benzimidazolyl | S | 1 | H |
| 5-146 | 1-Me-5-MeO-benzimidazol-2-yl | O | 1 | H |
| 5-147 | 1-Me-5-MeO-benzimidazol-2-yl | O | 2 | H |
| 5-148 | 1-Me-5-MeO-benzimidazol-2-yl | O | 3 | H |
| 5-149 | 1-Me-5-MeO-benzimidazol-2-yl | O | 4 | H |
| 5-150 | 1-Me-5-MeO-benzimidazol-2-yl | O | 5 | H |
| 5-151 | 1-Me-5-MeO-benzimidazol-2-yl | S | 1 | H |
| 5-152 | 1-Me-5-MeO-benzimidazol-2-yl | S | 2 | H |
| 5-153 | 1-Me-5-MeO-benzimidazol-2-yl | O | 1 | Me |

TABLE 5-continued

| Compound No. | X | Y | m | R |
|---|---|---|---|---|
| 5-154 | 1-Me, 5-MeO-benzimidazol-2-yl | O | 2 | Me |
| 5-155 | 1-Me, 5-MeO-benzimidazol-2-yl | O | 1 | F |
| 5-156 | 1-Me, 5-MeO-benzimidazol-2-yl | O | 1 | Cl |
| 5-157 | 1-Et, 5-MeO-benzimidazol-2-yl | O | 1 | H |
| 5-158 | 1-Et, 5-MeO-benzimidazol-2-yl | O | 2 | H |
| 5-159 | 1-Et, 5-MeO-benzimidazol-2-yl | O | 1 | MeO |
| 5-160 | 1-Et, 5-MeO-benzimidazol-2-yl | S | 1 | H |
| 5-161 | 1-Pr, 5-MeO-benzimidazol-2-yl | O | 1 | H |
| 5-162 | 1-Pr, 5-MeO-benzimidazol-2-yl | S | 1 | H |
| 5-163 | 1-iPr, 5-MeO-benzimidazol-2-yl | O | 1 | H |
| 5-164 | 1-iBu, 5-MeO-benzimidazol-2-yl | O | 1 | H |
| 5-165 | 1-iBu, 5-MeO-benzimidazol-2-yl | S | 1 | H |
| 5-166 | 1-Me, 5-EtO-benzimidazol-2-yl | O | 1 | H |
| 5-167 | 1-Me, 5-EtO-benzimidazol-2-yl | O | 1 | MeO |
| 5-168 | 1-Me, 5-EtO-benzimidazol-2-yl | O | 1 | Cl |
| 5-169 | 1-Me, 5-EtO-benzimidazol-2-yl | O | 2 | H |
| 5-170 | 1-Me, 5-EtO-benzimidazol-2-yl | O | 3 | H |
| 5-171 | 1-Me, 5-EtO-benzimidazol-2-yl | S | 1 | H |
| 5-172 | 1-Me, 5-EtO-benzimidazol-2-yl | S | 4 | Et |
| 5-173 | 1-Me, 5-PrO-benzimidazol-2-yl | O | 1 | H |

TABLE 5-continued

| Compound No. | X | Y | m | R |
|---|---|---|---|---|
| 5-174 | 1-Me, 5-PrO-benzimidazol-2-yl | S | 1 | H |
| 5-175 | 1-Me, 5-iPrO-benzimidazol-2-yl | O | 1 | H |
| 5-176 | 1-Me, 5-iPrO-benzimidazol-2-yl | O | 3 | H |
| 5-177 | 1-Me, 5-BuO-benzimidazol-2-yl | O | 1 | H |
| 5-178 | 1-Me, 5-iBuO-benzimidazol-2-yl | O | 1 | H |
| 5-179 | 1-Me, 5-sBuO-benzimidazol-2-yl | O | 1 | H |
| 5-180 | 1-Me, 5-tBuO-benzimidazol-2-yl | O | 1 | H |
| 5-181 | 1-Pr, 5-BuO-benzimidazol-2-yl | O | 1 | H |
| 5-182 | 1-Me, 5-BzO-benzimidazol-2-yl | O | 1 | H |
| 5-183 | 1-Me, 5-MeO, 6-Me-benzimidazol-2-yl | O | 1 | H |
| 5-184 | 1-Me, 5-MeO, 6-Br-benzimidazol-2-yl | O | 1 | H |
| 5-185 | 1-Me, 5-EtO, 6-F-benzimidazol-2-yl | O | 1 | H |
| 5-186 | 1-Me, 5,7-diF-benzimidazol-2-yl | O | 1 | H |
| 5-187 | 1-Me, 5-F-benzimidazol-2-yl | O | 1 | H |
| 5-188 | 1-Me, 5-Cl, 6-Me-benzimidazol-2-yl | O | 1 | H |
| 5-189 | 1-Et, 5-Cl, 6-Et-benzimidazol-2-yl | O | 1 | H |
| 5-190 | 1-Me, 5-Et-benzimidazol-2-yl | O | 1 | H |
| 5-191 | 1-Me, 5-Br-benzimidazol-2-yl | O | 1 | H |
| 5-192 | 1-Me, 5-CF$_3$, 7-Br-benzimidazol-2-yl | O | 1 | H |
| 5-193 | 1-Me, 5-CF$_3$, 7-Cl-benzimidazol-2-yl | O | 1 | H |

TABLE 5-continued

| Compound No. | X | Y | m | R |
|---|---|---|---|---|
| 5-194 | 1-Me-4-CF₃-benzimidazol-2-yl | O | 1 | H |
| 5-195 | 1-Me-5-CF₃-benzimidazol-2-yl | O | 1 | H |
| 5-196 | 1,4-diMe-5-Br-benzimidazol-2-yl (Br, Me, Me substituents) | O | 1 | H |
| 5-197 | 1-Me-5-F-6-Cl-benzimidazol-2-yl | O | 1 | H |
| 5-198 | 5-Br-1,7-diMe-benzimidazol-2-yl | O | 2 | H |
| 5-199 | 1-Me-5-tBu-benzimidazol-2-yl | O | 1 | H |
| 5-200 | 1-Me-5-HO-benzimidazol-2-yl | O | 1 | H |
| 5-201 | 1-Me-7-Me-benzimidazol-2-yl | O | 1 | H |
| 5-202 | 1-Me-5-Cl-6-Cl-benzimidazol-2-yl | O | 1 | H |
| 5-203 | 1-Me-5,6,7-triF-benzimidazol-2-yl | O | 1 | H |
| 5-204 | 1-Me-5-Br-6-BzO-benzimidazol-2-yl | O | 1 | H |
| 5-205 | 1-Me-7-Cl-benzimidazol-2-yl | O | 1 | H |
| 5-206 | 1,4,6-triMe-5-HO-benzimidazol-2-yl | O | 1 | H |
| 5-207 | 1,4,6-triMe-5-HO-benzimidazol-2-yl | O | 2 | H |
| 5-208 | 1,4,6-triMe-5-HO-benzimidazol-2-yl | O | 3 | H |
| 5-209 | 1,4,6-triMe-5-HO-benzimidazol-2-yl | S | 1 | H |
| 5-210 | 1,4,6-triMe-5-HO-benzimidazol-2-yl | O | 1 | Me |
| 5-211 | 1,4,6-triMe-5-HO-benzimidazol-2-yl | O | 1 | MeO |

TABLE 5-continued

| Compound No. | X | Y | m | R |
|---|---|---|---|---|
| 5-212 | 1,4,6-trimethyl-5-hydroxy-benzimidazol-2-yl | O | 1 | Cl |
| 5-213 | 1-methyl-benzimidazol-5-yl | O | 1 | H |
| 5-214 | 1-methyl-benzimidazol-5-yl | O | 2 | H |
| 5-215 | 1-methyl-benzimidazol-5-yl | O | 3 | H |
| 5-216 | 1-methyl-benzimidazol-5-yl | O | 4 | H |
| 5-217 | 1-methyl-benzimidazol-5-yl | O | 5 | H |
| 5-218 | 1-methyl-benzimidazol-5-yl | O | 1 | MeO |
| 5-219 | 1-methyl-benzimidazol-5-yl | O | 1 | Cl |
| 5-220 | 1-methyl-benzimidazol-5-yl | S | 1 | H |
| 5-221 | 1-methyl-benzimidazol-5-yl | S | 3 | H |
| 5-222 | 1-ethyl-benzimidazol-5-yl | O | 1 | H |
| 5-223 | 1-ethyl-benzimidazol-5-yl | S | 1 | H |
| 5-224 | 1-propyl-benzimidazol-5-yl | O | 1 | H |
| 5-225 | 1-propyl-benzimidazol-5-yl | O | 1 | Cl |
| 5-226 | 1-isopropyl-benzimidazol-5-yl | O | 1 | H |
| 5-227 | 1-isopropyl-benzimidazol-5-yl | S | 1 | H |
| 5-228 | 1-butyl-benzimidazol-5-yl | O | 1 | H |
| 5-229 | 1-benzyl-benzimidazol-5-yl | O | 1 | H |
| 5-230 | 1-benzyl-benzimidazol-5-yl | O | 3 | H |
| 5-231 | 1-benzyl-benzimidazol-5-yl | S | 1 | H |

TABLE 5-continued

| Compound No. | Structure | X | Y | m | R |
|---|---|---|---|---|---|
| 5-232 | benzimidazole | Me | O | 1 | H |
| 5-233 | benzimidazole | Et | O | 1 | H |
| 5-234 | benzimidazole | Bz | O | 1 | H |
| 5-235 | benzimidazole | Bz | S | 1 | H |
| 5-236 | 2-methylbenzimidazole | Me | O | 1 | H |

Of the compounds listed above, we particularly prefer the following, that is to say Compounds No. 1-11, 1-16, 1-18, 1-22, 1-27, 1-49, 1-50, 1-54, 1-56, 1-98, 1-100, 1-109, 1-129, 1-146, 1-155, 1-156, 1-229, 1-237, 1-238, 1-247, 1-250, 2-11, 2-49, 2-146, 2-229, 2-237, 2-250, 3-11, 3-49, 3-146, 3-229, 3-237, 3-250, 4-11, 4-49, 4-146, 4-229, 4-237, 4-250, 5-11, 5-49, 5-146, 5-229, 5-237 and 5-250, of which Compounds No. 1-11, 1-16, 1-18, 1-22, 1-27, 1-49, 1-50, 1-54, 1-56, 1-98, 1-100, 1-109, 1-129, 1-146, 1-229, 1-237, 1-238, 1-247, 1-250, 2-11, 2-49, 2-146, 2-229, 2-237, 2-250, 3-11, 3-49, 3-146, 3-229, 3-237and 3-250 are more preferred. Still more preferred compounds are Compounds No. 1-11, 1-16, 1-27, 1-49, 1-50, 1-54, 1-98, 1-100, 1-109, 1-129, 1-146, 1-229, 1-237, 1-238 and 1-250.

The most preferred compounds are Compounds No.:

1-11. 5-[4-(1-Methylbenzimidazol-2-ylmethoxy)benzyl]thiazolidine-2,4-dione;

1-49. 5-[4-(6-Methoxy-1-methylbenzimidazol-2-ylmethoxy)benzyl]thiazolidine-2,4-dione;

1-146. 5-[4-(5-Methoxy-1-methylbenzimidazol-2-ylmethoxy)benzyl]thiazolidine-2,4-dione;

1-229. 5-[4-(1-Benzylbenzimidazol-5-ylmethoxy)benzyl]thiazolidine-2,4-dione;

1-237. 5-[4-(5-Hydroxy-1,4,6,7-tetramethylbenzimidazol-2-ylmethoxy)benzyl]thiazolidine-2,4-dione; and 1-250. 5-[4-(5-Acetoxy-1,4,6,7-tetramethylbenzimidazol-2-ylmethoxy)benzyl]thiazolidine-2,4-dione;

and pharmaceutically acceptable salts thereof.

The compounds of the present invention may be prepared by a variety of processes well known in the art for the preparation of compounds of this general type. For example they may be prepared by the following Reaction Schemes A, B, C, D and E:

Reaction Scheme A

This reaction scheme provides for the preparation of compounds of formula (I) in which Z represents any of the groups of formula (i), (ii), (iii), and (iv), that is to say compounds (Ia).

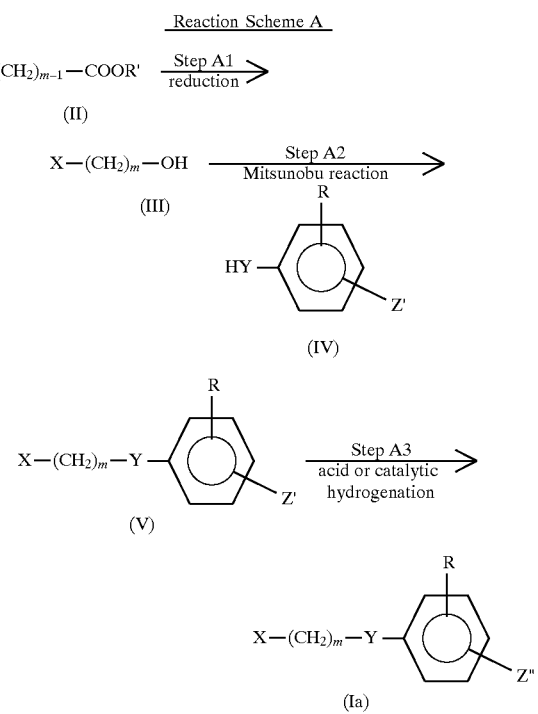

In the above formulae:

X, Y, R and m are as defined above;

R' represents an alkyl group having from 1 to 5 carbon atoms, which may be a straight or branched chain group, for example any of those alkyl groups having from 1 to 5 carbon atoms and included in the examples of groups which may be represented by $R^a$ and $R^b$ above, especially a methyl, ethyl or butyl group;

Z' represents a group of formula (i'), (ii'), (iii') or (iv'):

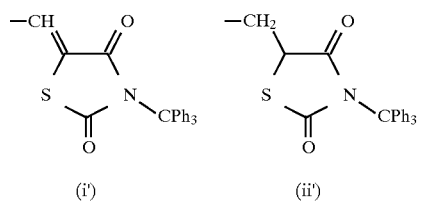

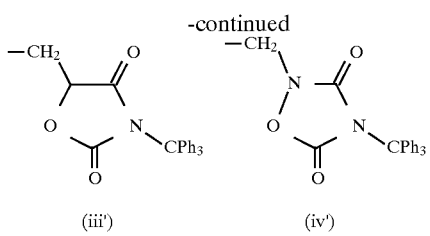

(iii')  (iv')

(in which Ph represents the phenyl group); and

Z" represents a group of formula (i), (ii), (iii) or (iv), as defined above.

Step A1

In Step A1 of this reaction scheme, a compound of formula (III) is prepared by reducing a compound of formula (II).

The reaction is conveniently carried out by reduction using a reducing agent.

There is no particular restriction on the nature of the reducing agents employed in this reaction, and any reducing agent conventionally employed in reactions of this type may equally be employed here. Examples of suitable reducing agents include metal hydrides, such as lithium borohydride, sodium borohydride, sodium cyanoborohydride, lithium aluminum hydride and diisopropylaluminum hydride.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons such as benzene, toluene, xylene, hexane or heptane; ethers such as diethyl ether, tetrahydrofuran or dioxane; amides such as dimethylformamide, dimethylacetamide or hexamethylphosphoric triamide; alcohols such as methanol, ethanol or isopropanol; and mixtures of any two or more of these solvents.

The reaction can take place over a wide range of temperatures, and the precise reaction temperature is not critical to the invention. In general, we find it convenient to carry out the reaction at a temperature of from that of ice-cooling to heating, e.g. to the reflux temperature of the reaction medium, preferably with ice-cooling or at about room temperature. The time required for the reaction may also vary widely, depending on many factors, notably the reaction temperature and the nature of the reagents, especially the reducing agent, and solvent employed. However, provided that the reaction is effected under the preferred conditions outlined above, a period of from 0.5 hour to several days will usually suffice.

The reaction is preferably carried out in an alcohol or in a mixture of alcohols and other organic solvents in the presence of lithium borohydride at a temperature of from room temperature to the reflux temperature of the reaction mixture for a period of from 1 hour to 1 day; or in a hydrocarbon or an ether in the presence of lithium aluminum hydride or diisobutylaluminum hydride with cooling or heating for a period of from 1 to 10 hours.

Step A2

In Step A2, a compound of formula (V) is prepared by reacting together a compound of formula (III), prepared as described in Step A1, and a compound of formula (IV) using the Mitsunobu reaction [O. Mitsunobu: Synthesis, 1 (1981)].

The reaction is usually carried out in a solvent in the presence of at least one azo compound and at least one phosphine.

There is no particular restriction on the nature of the azo compounds used, and any azo compounds commonly used in this type of reaction may equally be employed here used. Examples of such azo compounds include diethyl azodicarboxylate and 1,1'-(azodicarbonyl)dipiperidine. There is likewise no particular restriction on the nature of the phosphines used, and examples include triphenylphosphine and tributylphosphine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or 1,2-dichloroethane; ethers, such as diethyl ether, tetrahydrofuran or dioxane; amides, such as dimethylformamide, dimethylacetamide or hexamethylphosphoric triamide; and mixtures of any two or more of these solvents.

The reaction can take place over a wide range of temperatures, and the precise reaction temperature is not critical to the invention. In general, we find it convenient to carry out the reaction at a temperature of from room temperature to heating, e.g. to the reflux temperature of the reaction mixture, more preferably at a temperature of from room temperature to 60° C. The time required for the reaction may also vary widely, depending on many factors, notably the reaction temperature and the nature of the reagents and solvent employed. However, provided that the reaction is effected under the preferred conditions outlined above, a period of from several hours to several days, more preferably from 5 hours to 3 days will usually suffice.

Step A3

In Step A3, a compound of formula (Ia) is prepared by deprotecting the nitrogen atom in the compound of formula of formula (V). This may be achieved by conventional reactions, for example by treatment with an acid or by catalytic hydrogenation.

Where the reaction is carried out using an acid, there is no particular restriction on the nature of the acid used and any acid conventionally used for reactions of this type may equally be used here. Examples of suitable acids include trifluoroacetic acid, trifluoromethanesulfonic acid, acetic acid, hydrochloric acid and sulfuric acid in the presence or absence of a solvent.

Where a solvent is used, there is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers, such as diethyl ether, tetrahydrofuran or dioxane; amides, such as dimethylformamide, dimethylacetamide or hexamethylphosphoric triamide; esters, such as ethyl acetate or methyl acetate; water; and mixtures of any two or more of these solvents.

The reaction can take place over a wide range of temperatures, and the precise reaction temperature is not critical to the invention. In general, we find it convenient to carry out the reaction at a temperature of from ice-cooling to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to several tens of hours, more preferably from 0.5 to 10 hours, will usually suffice.

This step can also be achieved by catalytic hydrogenation of a compound of formula (V). There is no particular restriction on the nature of the catalysts used, and any hydrogenation catalysts commonly used in this type of reaction may equally be employed here. Examples of such hydrogenation catalysts include palladium-on-charcoal, palladium black, platinum oxide and platinum black, of which we prefer palladium-on-charcoal.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; halogenated hydrocarbons, such as chloroform, methylene chloride or carbon tetrachloride; ethers, such as diethyl ether, tetrahydrofuran or dioxane; alcohols, such as methanol, ethanol or isopropanol; amides, such as dimethylformamide, dimethylacetamide or hexamethylphosphoric triamide; and mixtures of any two or more of these solvents.

The reaction can take place over a wide range of temperatures, and the precise reaction temperature is not critical to the invention. In general, we find it convenient to carry out the reaction at a temperature of from room temperature to heating, e.g. at the reflux temperature of the reaction mixture, preferably at room temperature or with heating. The time required for the reaction may also vary widely, depending on many factors, notably the reaction temperature and the nature of the reagents and solvent employed. However, provided that the reaction is effected under the preferred conditions outlined above, a period of from several hours to several days, more preferably from 1 hour to 1 day will usually suffice.

Reaction Scheme B

This is a process which may be used to prepare compounds of formula (I) in which Y represents an oxygen atom and Z represents a group of formula (i) or (ii), that is a 2,4-dioxothiazolidin-5-ylidenylmethyl or 2,4-dioxothiazolidin-5-ylmethyl group, i.e. compounds of formulae (VII) and (VIII), respectively.

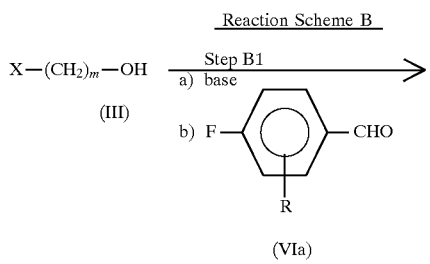

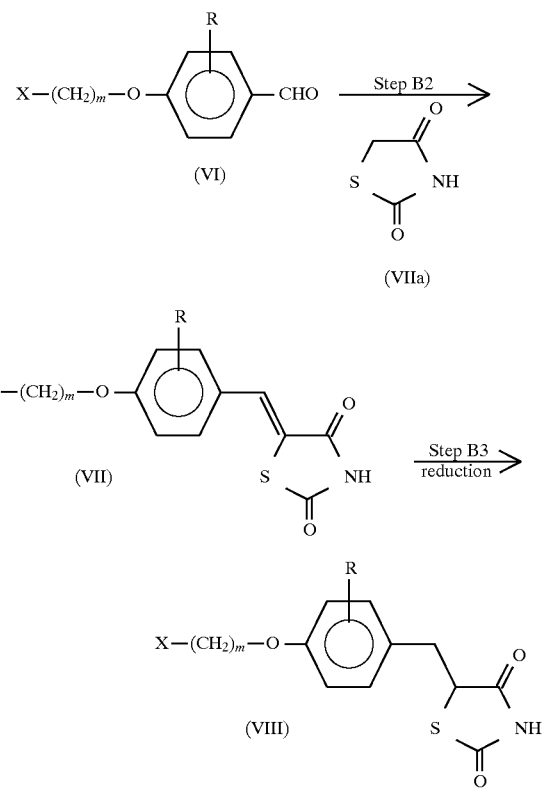

Step B1

In Step B1, a compound of formula (VI) is prepared by treating a compound of formula (III) with a base (the first stage) and then by reacting the resulting product with a p-fluorobenzaldehyde derivative of formula (VIa), such as 2-methoxy-4-fluorobenzaldehyde or 3-methyl-4-fluorobenzaldehyde (the second stage).

There is no particular restriction on the nature of the base used in the first stage, and any base commonly used in this type of reaction may equally be employed here. An example of such a base is sodium hydride.

The reaction in the first stage is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, tetrahydrofuran or dioxane; amides, such as dimethylformamide, dimethylacetamide or hexamethylphosphoric triamide; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to one day, more preferably from 1 to 10 hours, will usually suffice.

After completion of the first stage reaction, the second stage can be carried out by adding a p-fluorobenzaldehyde derivative of formula (VIa) to the reaction mixture and then by allowing the mixture to react. It is not necessary to separate the reaction product of the first stage before carrying out the second stage.

The reaction of the second stage can take place over a wide range of temperatures, and the precise reaction temperature is not critical to the invention. In general, we find it convenient to carry out the reaction at a temperature of from room temperature to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to several days will usually suffice.

Step B2

In Step B2, a compound of formula (VII) is prepared by reacting a compound of formula (VI) with thiazolidine-2,4-dione of formula (VIIa).

The reaction may be carried out in the presence or absence of a catalyst. Where the reaction is carried out in the presence of a catalyst, there is no particular restriction on the nature of the catalyst used, and any catalyst commonly used in this type of reaction may equally be employed here. Examples of such catalysts include sodium acetate, piperidinium acetate and piperidinium benzoate.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, tetrahydrofuran or dioxane; alcohols, such as methanol, ethanol or isopropanol; amides, such as dimethylformamide, dimethylacetamide or hexamethylphosphoric triamide; halogenated hydrocarbons, such as methylene chloride, chloroform or 1,2-dichloroethane; nitriles, such as acetonitrile or propionitrile; esters, such as ethyl formate or ethyl acetate; and mixtures of any two or more of these solvents.

The reaction can take place over a wide range of temperatures, and the reaction temperature is not critical to the invention. In general, we find it convenient to carry out the reaction with heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 1 to 50 hours will usually suffice.

The resulting compound of formula (VII) is a compound of the present invention and may be the desired product; alternatively, it may be subjected to optional Step B3.

Step B3

In Step B3, a compound of formula (VIII) is prepared by reducing a compound of formula (VII) by means of catalytic hydrogenation. There is no particular restriction on the nature of the catalysts used, and any hydrogenation catalysts commonly used in this type of reaction may equally be employed here. Examples of such hydrogenation catalysts include palladium-on-charcoal and palladium black, preferably palladium-on-charcoal.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, dioxane or tetrahydrofuran; alcohols, such as methanol, ethanol or isopropanol; organic acids, such as formic acid, acetic acid or propionic acid; amides such dimethylformamide, dimethylacetamide or hexamethylphosphoric triamide; and mixtures of any two or more of these solvents.

The reaction is normally carried out at atmospheric pressure or under superatmospheric pressure; preferably under superatmospheric pressure.

The reaction can take place over a wide range of temperatures, and the precise reaction temperature is not critical to the invention. In general, we find it convenient to carry out the reaction at a temperature of from room temperature or with heating, e.g. to the reflux temperature of the reaction mixture. The time required for the reaction may also vary widely, depending on many factors, notably the reaction pressure and temperature and the nature of the reagents and solvent employed. However, provided that the reaction is effected under the preferred conditions outlined above, a period of from several hours to several days, more preferably from 1 hour to 1 day, will usually suffice.

This step can also be effected by treating the compound of formula (VII) with a metal hydride according to the procedure disclosed in WO 93/1309A.

Reaction Scheme C

This scheme prepares a compound of formula (I) in which Z is at the para position and is a group of formula (v), that is a compound of formula (X), or in which Z is at the para position and is a group of formula (iv), that is a compound of formula (XI).

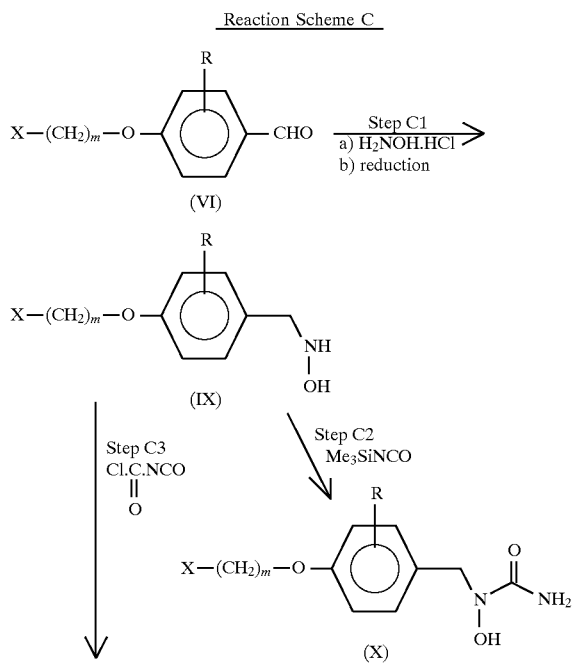

-continued
Reaction Scheme C

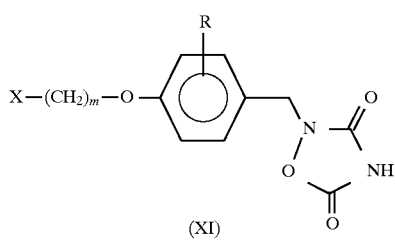

(XI)

In the above formula, R, X and m are as defined above.

Step C1

In Step C1, a compound of formula (IX) is prepared by reacting a compound of formula (VI) (which may have been prepared as described in Step B1 of Reaction Scheme B) with hydroxylamine (preferably as the hydrochloride), in a first stage, followed, in a second stage, by reducing the product.

The reaction of the compound of formula (VI) with hydroxylamine (hydrochloride) is, in general, preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, dioxane or tetrahydrofuran; alcohols, such as methanol, ethanol or isopropanol; amides, such as dimethylformamide, dimethylacetamide or hexamethylphosphoric triamide; halogenated hydrocarbons, such as methylene chloride, chloroform or 1,2-dichloroethane; nitriles, such as acetonitrile or propionitrile; esters, such as ethyl formate or ethyl acetate; amines, such as pyridine, triethylamine or N,N-diisopropyl-N-ethylamine; and mixtures of any two or more of these solvents.

The reaction can take place over a wide range of temperatures, and the precise reaction temperature is not critical to the invention. In general, we find it convenient to carry out the reaction at a temperature of from room temperature to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several hours to several tens of hours will usually suffice.

The subsequent reduction in the second stage of this step may be carried out by hydrogenation in the presence of a reducing agent. There is no particular restriction on the nature of the reducing agent used, and any reducing agent commonly used in this type of reaction may equally be employed here. Examples of such reducing agents include metal hydrides, such as lithium aluminum hydride, diisobutylaluminum hydride, lithium borohydride, sodium borohydride or sodium cyanoborohydride.

The second stage reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, dioxane or tetrahydrofuran; amides, such as dimethylformamide, dimethylacetamide or hexamethylphosphoric triamide; alcohols, such as methanol, ethanol or isopropanol; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to one day, more preferably from 1 to 10 hours, will usually suffice.

Step C2

In Step C2, a compound of formula (X) is prepared by reacting a compound of formula (IX) with trimethylsilyl isocyanate, $Me_3SiNCO$ (Me represents the methyl group).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene, hexane or heptane; ethers, such as diethyl ether, dioxane or tetrahydrofuran; amides, such as dimethylformamide, dimethylacetamide or hexamethylphosphoric triamide; halogenated hydrocarbons, such as methylene chloride, chloroform or 1,2-dichloroethane; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to several days will usually suffice.

The resulting compound of formula (X) is a compound of the present invention. However, if desired, the compound of formula (IX) may be subjected to optional Step C3.

Step C3

In Step C3, a compound of formula (XI) is prepared by reacting a compound of formula (IX) with N-(chlorocarbonyl)isocyanate, Cl.CO.NCO.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, tetrahydrofuran or dioxane; amides, such as dimethylformamide, dimethylacetamide or hexamethylphosphoric triamide; halogenated hydrocarbons, such as methylene chloride, chloroform or 1,2-dichloroethane; nitriles, such as acetonitrile or propionitrile; esters, such as ethyl formate or ethyl acetate; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from several tens of minutes to several tens of hours will usually suffice.

Reaction Scheme D

This is a process which may be used to prepare compounds of formula (I) in which Z represents a group of formula (ii) or (iii), that is a 2,4-dioxothiazolidin-5-ylmethyl or 2,4-dioxooxazolidin-5-ylmethyl group, i.e. compounds of formula (XV).

Reaction Scheme D

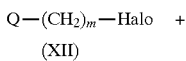

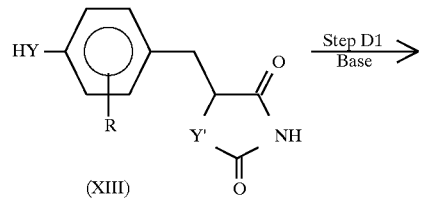

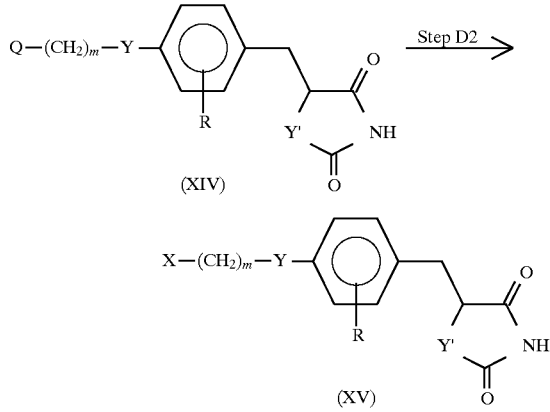

In the above formulae:
X, Y, R and m are as defined above;
Y' represents an oxygen or sulfur atom;
Q represents a lower alkoxycarbonyl group, a formyl group, a protected formyl group, a carboxyl group or a hydroxy group; and
Halo represents a halogen atom.

Step D1

In Step D1, a compound of formula (XIV) is prepared by reacting a compound of formula (XII) with a compound of formula (XIII) in the presence of a base.

There is no particular restriction on the nature of the base used, and any base commonly used in this type of reaction may equally be employed here. Examples of such bases include: inorganic bases, for example hydrides (such as sodium hydride or potassium hydride) and carbonates (such as potassium carbonate or cesium carbonate); and organic bases, such as triethylamine.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, tetrahydrofuran or dioxane; amides, such as dimethylformamide, dimethylacetamide or hexamethylphosphoric triamide; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 0.5 hour to several days will usually suffice.

The reaction is most preferably carried out with cooling or heating or at room temperature in an amide or in a mixture of at least one amide with at least one other organic solvent, in the presence of sodium hydride and for a period of from 1 to 10 hours.

The compounds of formula (XIV), which are prepared by this method, are important intermediates for the preparation of the compounds of formula (I) of the present invention, as well as for the preparation of other valuable compounds. These compounds of formula (XIV) thus also form part of the present invention.

Step D2

In Step D2, a compound of formula (XV) is prepared by one of the following two methods (a) and (b).

Step D2(a)

The compound of formula (XV) can be produced by reacting a compound of formula (XIV), in which Q represents a lower alkoxycarbonyl group, with a 1,2-diaminobenzene derivative.

Where Q represents a lower alkoxycarbonyl group, this preferably has a total of from 2 to 7 carbon atoms (i.e. the alkoxy part has from 1 to 6 carbon atoms), and may be a straight or branched chain group. Examples of such groups include the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl, 2-ethylbutoxycarbonyl, hexyloxycarbonyl and isohexyloxycarbonyl groups. Of these, we prefer those alkoxycarbonyl groups having from 2 to 5 carbon atoms, preferably the methoxycarbonyl, ethoxycarbonyl, propoxycarbonyl, isopropoxycarbonyl, butoxycarbonyl and isobutoxycarbonyl groups, more preferably the methoxycarbonyl and ethoxycarbonyl groups, and most preferably the ethoxycarbonyl group.

The reaction is normally and preferably effected in the presence or the absence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, preferably aromatic hydrocarbons, such as benzene, toluene or xylene; ethers, such as diethyl ether, tetrahydrofuran or dioxane; amides, such as dimethylformamide, dimethylacetamide or hexamethylphosphoric triamide; alcohols, such as methanol, ethanol or butanol; acids, such as acetic acid or propionic acid; and mixtures of any two or more of these solvents.

The reaction can take place over a wide range of temperatures, and the precise reaction temperature is not critical to the invention. In general, we find it convenient to carry out the reaction with heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 3 hours to several days will usually suffice.

The reaction is most preferably carried out in the absence of a solvent with heating at a temperature of from 50° C. to 150° C. for a period of from 5 hours to 2 days.

Step D2(b)

As an alternative, the compound of formula (XV) can be produced by reacting a compound of formula (XIV), in which Q represents a formyl group, in a first stage, with a 1,2-diaminobenzene derivative, and then, in a second stage, treating the product with an oxidizing agent.

The reaction in the first stage is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, which may be aliphatic or aromatic, such as benzene, toluene, xylene, hexane or heptane; ethers, such as diethyl ether, tetrahydrofuran, dioxane or 1,2-dimethoxyethane; amides, such as dimethylformamide, dimethylacetamide or hexamethylphosphoric triamide; alcohols, such as methanol, ethanol or isopropanol; acids, such as acetic acid or propionic acid; sulfoxides, such as dimethyl sulfoxide; and mixtures of any two or more of these solvents.

The reaction can take place over a wide range of temperatures, and the precise reaction temperature is not critical to the invention. In general, we find it convenient to carry out the reaction at about room temperature or with heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 1 hour to several days will usually suffice.

The product is then treated, in the second stage, with an oxidizing agent. There is no particular restriction on the nature of the oxidizing agent used, and any oxidizing agent commonly used in this type of reaction may equally be employed here. Examples of such oxidizing agents include iodine, silver oxide and lead tetraacetate, of which we prefer iodine.

The treatment with the oxidizing agent in this second stage is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include the solvents cited above for use in the first stage, preferably the ethers.

The reaction can take place over a wide range of temperatures, and the precise reaction temperature is not critical to the invention. In general, we find it convenient to carry out the reaction with heating. The time required for the reaction may also vary widely, depending on many factors, notably the reaction temperature and the nature of the reagents and solvent employed. However, provided that the reaction is effected under the preferred conditions outlined above, a period of from 1 hour to several days will usually suffice.

In the compound of formula (XIV), where Q represents a protected formyl group, the formyl-protecting group may be removed prior to subjecting the compound to the reaction of Step D2. Examples of such protected formyl groups include: for example, the dimethoxymethyl, diethoxymethyl, 1,3-dioxan-2-yl, 1,3-dioxolan-2-yl, 1,3-dithian-2-yl and 1,3-dithiolan-2-yl groups. The formyl-protecting group can be removed by conventional methods well known in the art, for example by contacting the compound of formula (XIV) with a conventional deprotecting agent under the conditions conventionally used for deprotection. These conditions are described in T. W. Green: Protective Groups in Organic Synthesis (John Wiley & Sons Ed.) or J. F. W. McOmie: Protective Groups in Organic Chemistry (Plenum Press Ed.).

Reaction Scheme E

This is a process which may be used to prepare compounds of formula (I) in which Z represents a group of formula (ii) or (iii), that is a 2,4-dioxothiazolidin-5-ylmethyl or 2,4-dioxooxazolidin-5-ylmethyl group, i.e. compounds of formula (XV).

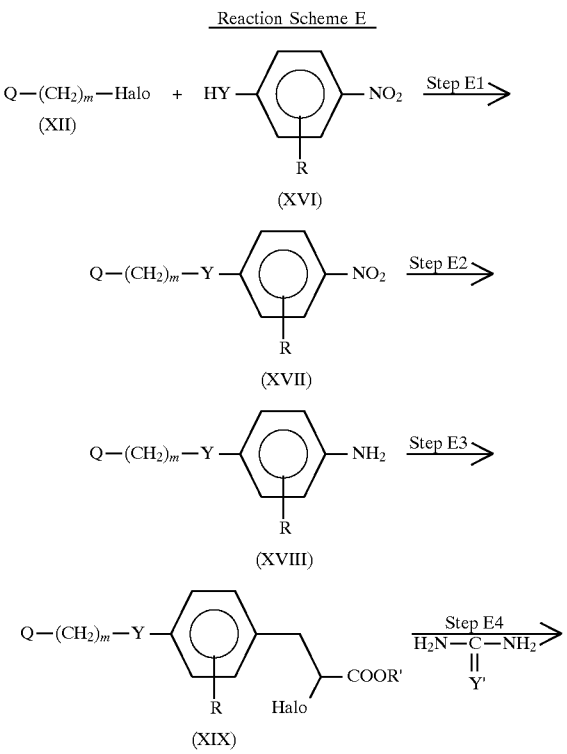

Reaction Scheme E -continued

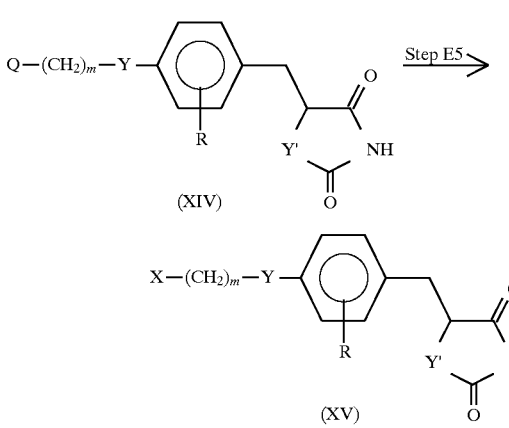

In the above formulae, Q, X, Y, Y', R, R', Halo and m are as defined above;

Step E1

In Step E1, a compound of formula (XVII) is prepared by reacting a compound of formula (XII) with a compound of formula (XVI) in the presence of a base. This reaction is essentially the same as that described in Step D1 of Reaction Scheme D, and may be carried out using the same reagents and reaction conditions.

Step E2

In Step E2, a compound of formula (XVIII) is prepared by reducing a compound of formula (XVII).

The reaction may be carried out by a conventional catalytic hydrogenation or by using any reducing agent capable of reducing a nitro group to form an amino group, such as zinc-acetic acid or tin-hydrochloric acid. This is a conventional type of reaction and the reaction conditions, solvents etc. which may be employed are well known in the art.

Step E3

In Step E3, a compound of formula (XIX) is prepared by subjecting a compound of formula (XVIII) to a Meerwein arylation reaction.

The conditions employed for the reaction are well known and are generally similar to those disclosed in Japanese Patent Kokai Application No. Sho 55-22657 or reported by S. Oae et al.: Bull. Chem. Soc. Japan, 53, 1065 (1980).

Step E4

In Step E4, a compound of formula (XIV) is prepared by reacting a compound of formula (XIX) with urea or thiourea and then subjecting the product to hydrolysis.

The conditions employed for this reaction are well known and are generally similar to those disclosed in Japanese Patent Kokai Application No. Sho 55-22657.

Step E5

In Step E5, a compound of formula (XV) is prepared from the compound (XIV), by one of Steps D(a) and D(b). The reaction is exactly the same as that shown in those Steps and may be carried out using the same reagents and reaction conditions.

In the steps described above, the products of each step can, if desired, be recovered from the reaction mixture by conventional means at the end of each reaction and, if necessary, the compounds obtained can be further purified by conventional means, for example, by column chromatography, recrystallization, reprecipitation or similar well known procedures. An example of one such technique comprises: adding a solvent to the reaction mixture; extracting the desired compound; and finally distilling off the solvent from the extract. The residue obtained may be purified by column chromatography through silica gel or like adsorbent to afford the desired compound as a pure specimen.

PREPARATION OF STARTING MATERIALS

Reaction Scheme F

This is a process which may be used to prepare compounds of formula (II) in which X represents a 1-benzimidazolyl group, that is a compound of formula (IIa).

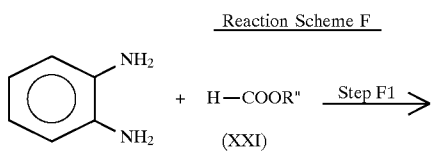

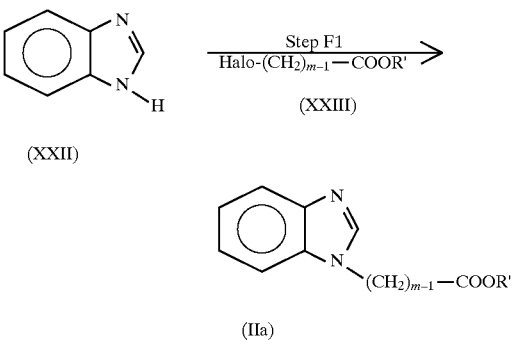

In the above formulae, R', m and Halo are as defined above; and R" represents a hydrogen atom or an alkyl group having from 1 to 6 carbon atoms. The benzimidazole ring in the compounds of formulae (XXII) and (IIa) may be unsubstituted or it may be substituted at any one or more of the 2-, 4-, 5-, 6- and 7-positions by a substituent selected from the group consisting of substituents α, defined and exemplified above. Similarly, the benzene ring of the compound of formula (XX) may be unsubstituted or it may have from 1 to 4 substituents selected from the group consisting of substituents α, defined and exemplified above. Also, the hydrogen atom shown in the compound of formula (XXI) may be replaced by one of substituents α. Where one or more of substituents α is present in any of the compounds of formulae (XX), (XXI), (XXII) and (IIa), it is preferably an alkyl group having from 1 to 4 carbon atoms, an aryl group having from 6 to 10 carbon atoms in a carbocyclic ring or an aralkyl group having a total of from 7 to 11 carbon atoms in the aryl and alkyl parts; the aryl and aralkyl groups may be unsubstituted or they may be substituted, preferably with from 1 to 3 substituents selected from the group consisting of substituents β, defined and exemplified above.

Where R" represents a lower alkyl group, this may be a straight or branched chain alkyl group having from 1 to 6 carbon atoms. Examples of such groups include: the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms; most preferably the methyl or ethyl groups.

Step F1

In Step F1, a compound of formula (XXII) is prepared by reacting a compound of formula (XX) with a compound of formula (XXI). This reaction is essentially the same as that described in Step D2 of Reaction Scheme D, and may be carried out using the same reagents and reaction conditions.

Step F2

In Step F2, a compound of formula (IIa) is prepared by condensing a compound of formula (XXII) with a compound of formula (XXIII). This is a well known type of reaction and may be carried out by well known procedures, for example that described in Liebigs Ann. Chem., 1078 (1983).

Reaction Scheme G

This is a process which may be used to prepare compounds of formula (II) in which X represents a benzimidazole group which is substituted by the group of formula —(CH$_2$)$_{m-1}$—COOR' at the 4-, 5-, 6- or 7-position, that is a compound of formula (IIb).

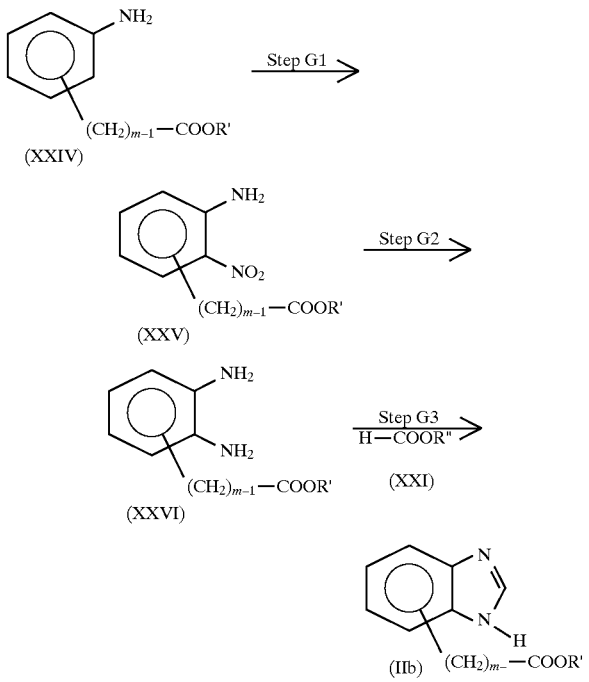

In the above formulae, R' and m are as defined above.

The benzimidazole ring in the compound of formula (IIb) may be unsubstituted or it may be substituted at from 1 to 5 of the 1-, 2-, 4-, 5-, 6- and 7-positions by a substituent selected from the group consisting of substituents α, defined and exemplified above. Similarly, the benzene ring of the compounds of formulae (XXIV), (XXV) and (XXVI) may be unsubstituted or it may have from 1 to 3 substituents selected from the group consisting of substituents α, defined and exemplified above [provided that no more than one of the positions ortho to the amino group of the compound of formula (XXIV) may be so substituted]. Also, the hydrogen atom shown in the compound of formula (XXI) may be replaced by one of substituents α. Furthermore, the amino group or one of the amino groups of the compounds of formulae (XXIV), (XXV) and (XXVI) may have a single substituent selected from the group consisting of substituents α, defined and exemplified above. Where one or more of substituents α is present in any of the compounds of formulae (XXI), (XXIV), (XXV), (XXVI) and (IIb), it is preferably an alkyl group having from 1 to 4 carbon atoms, an aryl group having from 6 to 10 carbon atoms in a carbocyclic ring or an aralkyl group having a total of from 7 to 11 carbon atoms in the aryl and alkyl parts; the aryl and aralkyl groups may be unsubstituted or they may be substituted, preferably with from 1 to 3 substituents selected from the group consisting of substituents β, defined and exemplified above.

Step G1

In Step G1, a compound of formula (XXV) is prepared by nitrating a compound of formula (XXIV). This type of nitration reaction is well known and it may be carried out according to the known procedure described by, for example: J. G. Hoggett, R. B. Moodie, J. R. Peton, K. Schofield, Nitration and Aromatic Reactivity, Cambridge University Press, Cambridge, 1971; K. Schofield, Aromatic Nitration, Cambridge University Press, Cambridge, 1980; P. B. D. de la Mare and J. H. Ridd, Aromatic Substitution, Nitration and Halogenation, Academic Press, New York, 1959; A. V. Topchiev, Nitration of Hydrocarbons and Other Organic Compounds, Pergamon Press, New York, 1959; L. F. Albright. in Kirk-Othmer, Encyclopedia of Chemical Technology, 2nd ed. Vol. 13; The Interscience Encyclopedia, Inc., New York, pp.784, 1967; H. A. Lubs, Chemistry of Synthetic Dyes and Pigments, Reinhold Publishing Corp., New York, 1955, pp.12, 71, 350 etc.

Step G2

In Step G2, a compound of formula (XXVI) is prepared by reducing a compound of formula (XXV).

There is no particular restriction on the nature of the reducing agent employed in this reaction and any reducing agent commonly used in reactions of this type may equally be employed here. Examples of suitable reducing agents include: a combination of tin and hydrochloric acid; zinc and alcoholic alkali; zinc and acetic acid; sodium amalgam and water; sodium borohydride and tin; and similar combinations.

The reaction may be conducted in the presence or the absence of a solvent. Where a solvent is employed, there is no particular restriction on its nature, provided that it has no adverse effect on the reaction or on the reagents involved and that it can dissolve the reagents, at least to some extent. Examples of suitable solvents include: hydrocarbons such as benzene, toluene, xylene, hexane or heptane; ethers such as diethyl ether, tetrahydrofuran or dioxane; amides such as dimethylformamide, dimethylacetamide or hexamethylphosphoric triamide; alcohols such as methanol, ethanol, propanol or t-butanol; esters such as ethyl acetate; water; and mixtures of any two or more of these solvents.

The reaction can take place over a wide range of temperatures, and the precise reaction temperature is not critical to the invention. In general, we find it convenient to carry out the reaction at a temperature of from ice-cooling to heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 0.5 hour to several days will usually suffice.

This step can also be carried out by catalytic hydrogenation.

There is no particular restriction on the nature of the catalyst employed in this reaction and any catalyst commonly used in reactions of this type may equally be employed here. Examples of suitable catalysts include:

Raney nickel, palladium-on-charcoal, palladium-black, ruthenium and platinum oxide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons such as benzene, toluene, xylene, hexane or heptane; ethers such as diethyl ether, tetrahydrofuran or dioxane; amides such as dimethylformamide, dimethylacetamide or hexamethylphosphoric triamide; alcohols such as methanol, ethanol, propanol or ethylene glycol; halogenated hydrocarbons such as chloroform or methylene dichloride; water; and mixtures of any two or more of these solvents.

The reaction can take place over a wide range of temperatures, and the precise reaction temperature is not critical to the invention. In general, we find it convenient to carry out the reaction at about room temperature or with heating, e.g. to the reflux temperature of the reaction mixture. The time required for the reaction may also vary widely, depending on many factors, notably the reaction temperature and the nature of the reagents and solvent employed. However, provided that the reaction is effected under the preferred conditions outlined above, a period of from 0.5 hour to several days will usually suffice.

Step G3

In Step G3, a compound of formula (IIb) is prepared by reacting a compound of formula (XXVI) with a compound of formula (XXI). This reaction is essentially the same as that described in Step D2 of Reaction Scheme D, and may be carried out using the same reagents and reaction conditions.

Reaction Scheme H

The 1,2-diaminobenzene derivative, which is used in Step D2 of Reaction Scheme D and in Step F1 of Reaction Scheme F, can be prepared by the procedure described in the following reaction scheme H.

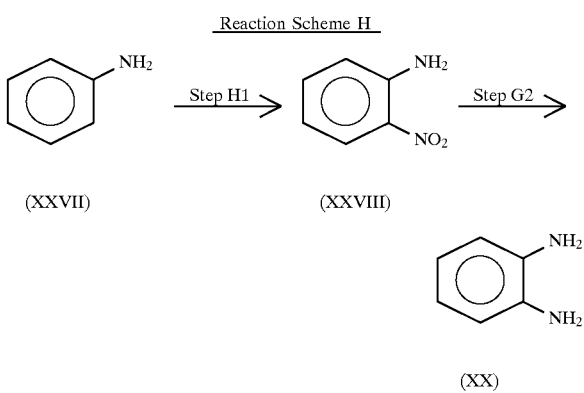

Step H1

In Step H1, a compound of formula (XXVIII) is prepared by nitrating a compound of formula (XXVII). This reaction is essentially the same as that described in Step G1 of Reaction Scheme G, and may be carried out using the same reagents and reaction conditions.

SteP H2

In Step H2, a compound of formula (XX) is prepared by reducing a compound of formula (XXVIII). This reaction is essentially the same as that described in Step G2 of reaction Scheme C, and may be carried out using the same reagents and reaction conditions.

BIOLOGICAL ACTIVITY

The compounds of formula (I) and salts thereof possess the ability to reduce insulin resistance, hyperlipidemia, hyperglycemia, gestational diabetes mellitus, obesity, impaired glucose tolerance, diabetic complications, arteriosclerosis, cataracts, and polycystic ovary syndrome, and, in addition, have aldose reductase inhibitory activity, 5-lipoxygenase inhibitory activity and the ability to inhibit the formation of lipid peroxide. They are thus useful for the prevention and/or therapy of hyperlipidemia, hyperglycemia, obesity, impaired glucose tolerance, hypertension, osteoporosis, cachexia, fatty liver, diabetic complications, arteriosclerosis, and cataracts; for the prevention and/or therapy of other diseases caused by insulin resistance, including gestational diabetes mellitus, and polycystic ovary syndrome; and for the prevention and/or therapy of inflammatory diseases, acne, sunburn, psoriasis, eczema, allergic diseases, asthma, GI ulcer, cardiovascular diseases, atherosclerosis, and cellullar injury induced by ischemic diseases.

The compounds of the present invention can be administered in various forms, depending on the disorder to be treated and the age, condition and body weight of the patient, as is well known in the art. For example, where the compounds are to be administered orally, they may be formulated as tablets, capsules, granules, powders or syrups; or for parenteral administration, they may be formulated as injections (intravenous, intramuscular or subcutaneous), drop infusion preparations or suppositories. For application by the ophthalmic mucous membrane route, they may be formulated as eyedrops or eye ointments. These formulations can be prepared by conventional means, and, if desired, the active ingredient may be mixed with any conventional additive, such as an excipient, a binder, a disintegrating agent, a lubricant, a corrigent, a solubilizing agent, a suspension aid, an emulsifying agent or a coating agent.

Examples of vehicles which may be employed include: organic vehicles including; sugar derivatives, such as lactose, sucrose, glucose, mannitol and sorbitol; starch derivatives, such as corn starch, potato starch, α-starch, dextrin and carboxymethylstarch; cellulose derivatives, such as crystalline cellulose, low-substituted hydroxypropylcellulose, hydroxypropylmethylcellulose, carboxymethylcellulose, calcium carboxymethylcellulose and internally bridged sodium carboxymethylcelluilose; gum arabic; dextran; Pullulane; and inorganic vehicles including silicate derivatives, such as light silicic anhydride, synthetic aluminum silicate and magnesium aluminate metasilicate; phosphates, such as calcium phosphate; carbonates, such as calcium carbonate; and sulfates, such as calcium sulfate.

Examples of lubricants which may be employed include: stearic acid; metal stearates, such as calcium stearate and magnesium stearate; talc; colloidal silica; waxes, such as bee gum and spermaceti wax; boric acid; adipic acid; sulfates, such as sodium sulfate; glycol; fumaric acid; sodium benzoate; DL-leucine; fatty acid sodium salts; lauryl sulfates, such as sodium lauryl sulfate and magnesium lauryl sulfate; silicates, such as silicic anhydride and silicic acid hydrate; and the aforementioned starch derivatives.

Examples of binders which may be employed include: polyvinylpyrrolidone; macrogol; and the same compounds as are mentioned above for the vehicles.

Examples of disintegrators which may be employed include: the same compounds as are mentioned above for the vehicles; and chemically modified starches and celluloses, such as sodium crosscarmellose, sodium carboxymethylstarch and bridged polyvinylpyrrolidone.

Examples of stabilizers which may be employed include: paraoxybenzoates, such as methylparabene and propylparabene; alcohols, such as chlorobutanol, benzylalcohol and phenylethylalchol; benzalkonium chloride; phenols, such as phenol and cresol; thimerosal; dehydroacetic acid; and sorbic acid.

Examples of corrigents which may be employed include: sweetening agents, acidifiers and spices.

Although the dosage will vary depending on the symptoms, age and body weight of the patient, the nature and severity of the disorder to be treated or prevented, the route of administration and the form of the drug, in general, where the drug to to be administered orally, a daily dosage ranging from a minimum of 0.1 mg (preferably 1 mg) to a maximum of 2000 mg (preferably 500 mg and more preferably 100 mg) of the compound is recommended for an adult human patient, and this may be administered in a single dose or in divided doses. Where the drug to be administered intravenously, a daily dosage ranging from a minimum of 0.01 mg (preferably 0.1 mg) to a maximum of 500 mg (preferably 50 mg) of the compound is recommended for an adult human patient, and this may be administered in a single dose or in divided doses.

The activity of the compounds of the present invention is illustrated by the following Experiments.

Experiment 1
Hypoglycemic activity

The test animals used were hyperglycemic male mice of the KK strain, each having a body weight of at least 40 g. The compounds under test were mixed with a 1:1 by volume mixture of polyethylene glycol 400 and water. Each animal was orally administered a test compound in the amount shown in the following Table 6 and then allowed to feed freely for 18 hours. At the end of this time, blood was collected from the tail veins without anesthesia. The blood glucose level (BGL) was determined by means of a glucose analyzer (GL-101, manufactured by Mitsubishi Kasei Co. or a Glucoroder-F manufactured by Shino Test Co.).

The hypoglycemic effect was calculated by the following equation:

Hypoglycemic effect (%)=[(BGL$_s$−BGL$_t$)/BGL$_s$]×100 where:

BGL$_s$ is the blood glucose level in the group administered a solvent only, but no active compound; and BGL$_t$ is the blood glucose level in the group administered a test compound.

The results are shown in the following Table 6, in which each compound of the present invention is identified by the number of one of the following Examples in which its preparation is illustrated.

TABLE 6

| Cpd. of Example No. | Dose (mg/kg) | Hypoglycemic effect (%) |
|---|---|---|
| 1 | 1 | 36.2 |
| 2 | 1 | 27.2 |
| 3 | 1 | 11.2 |
| 4 | 1 | 19.3 |

As is apparent from Table 6, the compounds of the present invention exhibited excellent activity.

Experiment 2
Inhibition of Aldose reductase

Bovine lens aldose reductase was separated and partially purified by the method of S. Hyman and J. H. Kinoshita [J. Biol. Chem. 240, 877 (1965)] and K. Inagaki, I. Miwa and J. Okuda [Arch. Biochem. Biophys., 216, 337 (1982)], and its activity was determined photometrically by the method of Varma et al. [Biochem. Pharmac., 25, 2505 (1976)]. Inhibition of enzyme activity was measured for the compounds of the present invention at a concentration of 5 µg/ml, and the measured values were used to calculate the IC$_{50}$ values. The results are shown in the following Table 7.

TABLE 7

| Cpd. of Example No. | Inhibition (%) at 5 µg/ml | IC$_{50}$ (µg/ml) |
|---|---|---|
| 1 | 80.3 | 0.77 |
| 3 | 79.6 | 1.40 |

Experiment 3
Toxicity

The toxicity of the compounds of the present invention was tested on male F344 rats, divided into groups of 5. The test compound was adminstered orally to each test animal at a dose of 50 mg/kg of body weight per day for 2 weeks. The test compounds used were those of Examples 1 and 2. The animals were observed for 2 successive weeks, and, during that period, they showed no abnormalities which could be attributed to the test compounds. In view of the substantial dose adminstered to each animal, the zero mortality rate indicates that the compounds of the present invention have very low toxicity.

The compounds of the present invention thus have excellent activities combined with a very low toxicity, rendering them ideally suited to therapeutic use.

EXAMPLE 1

5-[4-(1-Methylbenzimidazol-2-ylmethoxy)benzyl]thiazolidine-2,4-dione (Compound No. 1-11)

A mixture of 1.0 g of N-methyl-1,2-phenylenediamine, 3.8 g of 5-[4-(ethoxycarbonylmethoxy)benzyl]thiazolidine-2,4-dione (prepared as described in Preparation 4), 20 ml of concentrated aqueous hydrochloric acid, 10 ml of 1,4-dioxane and 10 ml of water was heated under reflux for 5 hours. At the end of this time, the insoluble materials which had precipitated from the reaction mixture were collected by filtration and the precipitate thus obtained was dissolved in tetrahydrofuran. Water was then added to the solution. The resulting aqueous mixture was neutralized by adding sodium hydrogencarbonate and then extracted with ethyl acetate. The extract was washed with an aqueous solution of sodium chloride and dried over anhydrous sodium sulfate. The solvent was then removed by evaporation under reduced pressure, and the resulting residue was purified by column chromatography through silica gel using ethyl acetate and then ethanol as the eluent. The product was then recrystallized twice from a mixture of tetrahydrofuran and ethyl acetate, to give 1.3 g of the title compound, melting at 230°–231° C.

EXAMPLE 2

5-[4-(6-Methoxy-1-methylbenzimidazol-2-ylmethoxy)benzyl]thiazolidine-2,4-dione (Compound No. 1-49)

A mixture of 21.8 g of 5-methoxy-N-methyl-1,2-phenylenediamine (prepared as described in Preparation 9), 63.4 g of 5-(4-methoxycarbonylmethoxybenzyl)thiazolidin-2,4-dione (prepared as described in Preparation 21), 250 ml of 1,4-dioxane and 750 ml of concentrated aqueous hydrochloric acid was heated under reflux for 60 hours. At the end of this time, the reaction mixture was cooled with ice, after which the solid matter was collected by filtration. 800 ml of a 5% w/v aqueous solution of sodum hydrogencarbonate was added to this matter, and the resulting mixture was stirred at room temperature for 2 hours. Insoluble materials were then collected by filtration and dissolved in a mixture of 1000 ml of dimethylformamide and 200 ml of methanol. The resulting solution was decolorized by treatment with activated charcoal, which was then removed by filtration. The filtrate was then concentrated by evaporation under reduced pressure to a volume of about 50 ml. The resulting concentrate was added to 750 ml of diethyl ether and the solution thus obtained was allowed to stand for 2 days. At the end of this time, the resulting precipitate was collected by filtration, to give 20.1 g of the title compound, melting at 267°–271 20 C. and having an Rf value=0.68 (on thin layer chromatography on silica gel; using a developing solvent of methylene chloride containing 5% v/v ethanol).

EXAMPLE 3

5-[4-(5-Hydroxy-1,4,6,7-tetramethylbenzimidazol-2-ylmethoxy)benzyl]thiazolidine-2,4-dione (Compound No. 1-237)

A mixture of 1.0 g of 4-acetoxy-N-methyl-3,5,6-trimethyl-1,2-phenylenediamine (prepared as described in Preparation 19), 2.7 g of 5-(4-methoxycarbonylmethoxybenzyl)thiazolidine-2,4-dione (prepared as described in Preparation 21), 5 ml of 1,4-dioxane and 25 ml of concentrated aqueous hydrochloric acid was heated under reflux for 2 days. At the end of this time, the reaction mixture was added to ice-water and the resulting mixture was neutralized by the addition of sodium hydrogencarbonate. It was then extracted with ethyl acetate. The extract was washed with a saturated aqueous solution of sodium chloride and dried over anhydrous magnesium sulfate. The solvent was then removed by distillation under reduced pressure, after which the residue was purified by column chromatography through silica gel, using ethyl acetate as the eluent. Fractions containing the title compound were collected and the solvent was removed by distillation under reduced pressure, to give a red residual oil. 150 ml of diethyl ether were added to the oil, and the mixture was agitated ultrasonically for 5 minutes. The precipitate which separated out was collected by filtration and dissolved in 300 ml of tetrahydrofuran. The resulting solution was concentrated to a volume of between about 10 ml and 20 ml by evaporation under reduced pressure. 200 ml of ethyl acetate were added to the concentrate, and the mixture was agitated ultrasonically for 20 minutes. The precipitate which separated out was collected by filtration, to give 0.52 g of the title compound, melting at 240°–244° C. and having an Rf value=0.44 (on thin layer chromatography on silica gel; developing solvent: ethyl acetate).

EXAMPLE 4

5-[4-(5-Hydroxy-1,4,6,7-tetramethylbenzimidazol-2-ylmethoxy)benzyl]thiazolidine-2,4-dione hydrochloride (Hydrochloride of Compound No. 1-237)

A suspension of 0.12 g of 5-[4-(5-hydroxy-1,4,6,7-tetramethylbenzimidazol-2-ylmethoxy)benzyl]thiazolidine-2,4-dione (prepared as described in Example 3) in 3 ml of a 4N solution of hydrogen chloride in ethyl acetate was stirred for 3 hours at room temperature, after which it was allowed to stand overnight. Insoluble substances were collected by filtration and washed with tetrahydrofuran, with ethyl acetate and with diethyl ether, in that order, to give 0.11 g of the title compound, melting at 228°–231° C.

EXAMPLE 5

5-[4-(5-Acetoxy-1,4,6,7-tetramethylbenzimidazol-2-ylmethoxy)benzyl]thiazolidine-2,4-dione (Compound No. 1-250)

0.032 ml of acetic anhydride were added at room temperature to a solution of 0.12 g of 5-[4-(5-hydroxy-1,4,6,7-tetramethylbenzimidazol-2-ylmethoxy)benzyl]thiazolidine-2,4-dione (prepared as described in Example 3) in 2 ml of pylidine, and the resulting mixture was stirred for 3 hours, after which it was allowed to stand overnight. At the end of this time, the reaction mixture was freed from the solvent by evaporation under reduced pressure, and the resulting residue was mixed with water. The aqueous mixture was then extracted with ethyl acetate. The extract was washed with water and then with a saturated aqueous solution of sodium chloride and dried over anhydrous magnesium sulfate. The solvent was removed by distillation under reduced pressure, after which the solid residue was triturated with diethyl ether and collected by filtration. It was then washed with diethyl ether, to give 0.12 g of the title compound, melting at 250°–253° C.

EXAMPLE 6

5-[4-(5-Methoxy-1-methylbenzimidazol-2-ylmethoxy)benzyl]thiazolidine-2,4-dione (Compound No. 1-146)

A mixture of 1.17 g of 4-methoxy-N-methyl-1,2-phenylenediamine (prepared as described in Preparation 25), 3.0 g of 5-(4-methoxycarbonylmethoxybenzyl)thiazolidine-2,4-dione (prepared as described in Preparation 21), 20 ml of 1,4-dioxane and 60 ml of concentrated hydrochloric acid was heated under reflux for 2 days. At the end of this time, the reaction mixture was poured into ice-water and the resulting mixture was neutralized with sodium hydrogencarbonate, after which it was extracted with ethyl acetate. The extract was washed with a saturated aqueous solution of sodium chloride and dried over anhydrous sodium sulfate. The solvent was then removed by distillation under reduced pressure, after which the residue was purified by column chromatography through silica gel, using a solution of methylene chloride containing 3% by volume ethanol as the eluent, to give 0.3 g of the title compound, melting at 209°–210° C. and having an Rf value=0.56 (on thin layer chromatography on silica gel; developing solvent: methylene chloride containing 5% by volume ethanol).

EXAMPLE 7

5-[4-(1-Benzylbenzimidazol-5-ylmethoxy)benzyl]thiazolidine-2,4-dione hemihydrate (Hemihydrate of Compound No. 1-229)

A mixture of 0.26 g of 5-[4-(1-benzylbenzimidazol-5-ylmethoxy)benzyl]-3-triphenylmethylthiazolidine-2,4-dione (prepared as described in Preparation 29), 3 ml of acetic acid and 1 ml of water was stirred for 3 hours at 50° C. in oil bath. At the end of this time, the reaction mixture was neutralized with sodium hydrogencarbonate and then extracted with ethyl acetate. The extract was washed with a saturated aqueous solution of sodium chloride and dried over anhydrous sodium sulfate. The solvent was then removed by evaporation under reduced pressure, and the resulting residue was recrystallized from a mixture of ethanol and methanol, to give 116 mg of the title compound, melting at 185°–187° C.

Preparation 1

Methyl 4-nitrophenoxyacetate

A mixture of 56 g of 4-nitrophenol, 90 g of methyl bromoacetate, 100 g of potassium carbonate and 500 ml of dimethylformamide was stirred at room temperature for 2 days. At the end of this time, the solvent was removed by distillation under reduced pressure. The resulting residue was mixed with water and the aqueous mixture was extracted with ethyl acetate. The extract was washed with water and dried over anhydrous sodium sulfate, after which the solvent was removed by distillation under reduced pressure. The resulting residue was triturated with hexane to give 63.3 g of the title compound, melting at 98°–99° C.

Preparation 2

Methyl 4-aminophenoxyacetate

A solution of 30.8 g of methyl 4-nitrophenoxyacetate (prepared as described in Preparation 1) in 500 ml of methanol was shaken in an atmosphere of hydrogen and in the presence of 5.0 g of 10% w/w palladium-on-charcoal for 6 hours. At the end of this time, the reaction mixture was filtered and the filtrate was concentrated by evaporation under reduced pressure, to give 25.8 g of the title compound having an Rf value=0.79 (on thin layer chromatography on silica gel; developing solvent: ethyl acetate).

Preparation 3

Methyl 4-(2-bromo-2-butoxycarbonylethyl-1-yl) phenoxyacetate 98 g of 47% w/W aqueous hydrobromic acid, followed by 33 ml of an aqueous solution containing 12.8 g of sodium nitrite, were added to a solution of 25.8 g of methyl 4-aminophenoxyacetate (prepared as described in Preparation 2) in 263 ml of a 2:5 by volume mixture of methanol and acetone, whilst ice-cooling, and the resulting mixture was stirred, whilst ice-cooling, for 30 minutes. 18.2 g of butyl acrylate were then added, and the reaction mixture was stirred for a further 30 minutes, whilst ice-cooling. 3.2 g of copper(I) bromide were then added to the mixture, and the mixture was stirred overnight at room temperature. At the end of this time, the reaction mixture was freed from the solvent by distillation under reduced pressure, and the residue was mixed with an aqueous solution of sodium chloride. It was then extracted with ethyl acetate. The extract was washed with an aqueous solution of sodium chloride and dried over anhydrous sodium sulfate. On distilling off the solvent, there were obtained 51.7 g of the title compound having an Rf value=0.46 (on thin layer chromatography on silica gel; developing solvent: a 5:1 by volume mixture of hexane and ethyl acetate) as a crude product.

Preparation 4

5-[4-(Ethoxycarbonylmethoxy)benzyl]thiazolidine-2,4-dione

A mixture of 100 g of methyl 4-(2-bromo-2-butoxycarbonylethyl-1-yl)phenoxyacetate (prepared as described in Preparation 3), 22 g of thiourea and 200 ml of ethanol was heated under reflux for 2.5 hours, after which 2N aqueous hydrochloric acid was added to the reaction mixture. The mixture was then heated under reflux for 5 hours. At the end of this time, the reaction mixture was freed from the solvent by distillation under reduced pressure. The resulting residue was diluted with water and the aqueous mixture was extracted with ethyl acetate. The extract was dried over anhydrous magnesium sulfate, after which the solvent was removed by distillation under reduced pressure. The resulting residue was purified by column chromatography through silica gel using a 2:5 by volume mixture of ethyl acetate and hexane as the eluent, to give 19.4 g of the title compound, melting at 105°–106° C.

Preparation 5

5-Methoxy-2-nitroaniline 70 ml of a 28% w/v methanolic solution of sodium methoxide were added at room temperature to a solution of 25 g of 5-chloro-2-nitroaniline in 500 ml of 1,4-dioxane, and the resulting mixture was heated under reflux for 4 hours, after which the solvent was removed by distillation under reduced pressure. The resulting residue was diluted with water, and the resulting aqueous mixture was extracted with ethyl acetate. The extract was washed with a saturated aqueous solution of sodium chloride and dried over anhydrous sodium sulfate, after which the solvent was removed by distillation under reduced pressure. The resulting residue was purified by column chromatography through silica gel using a gradient elution method, with mixtures of ethyl acetate and hexane in ratios ranging from 1:4 to 1:2 by volume as the eluent, to give 16.3 g of the title compound, melting at 124°–128° C.

Preparation 6

N-t-Butoxycarbonyl-5-methoxy-2-nitroaniline 25 g of di-t-butyl dicarbonate, 15 ml of pyridine and 0.6 g of 4-dimethylaminopyridine were added at room temperature to a solution of 16 g of 5-methoxy-2-nitroaniline (prepared as described in Preparation 5) in 500 ml of dehydrated tetrahydrofuran, and the resulting mixture was stirred for 2 hours. At the end of this time, the reaction mixture was freed from the solvent by distillation under reduced pressure, and the resulting residue was diluted with water. The resulting aqueous mixture was extracted with ethyl acetate. The extract was washed with a saturated aqueous solution of sodium chloride and dried over anhydrous sodium sulfate, after which the solvent was removed by distillation under reduced pressure. The resulting residue was purified by column chromatography through silica gel using a 1:10 by volume mixture of ethyl acetate and hexane as the eluent, to give 12.5 g of the title compound, melting at 112°–114° C.

Preparation 7

N-t-Butoxycarbonyl-N-methyl-5-methoxy-2-nitroaniline

A solution of 49.6 g of N-t-butoxycarbonyl-5-methoxy-2-nitroaniline (prepared as described in Preparation 6) in 300 ml of dehydrated dimethylformamide was added, whilst ice-cooling, to a suspension of 12.0 g of sodium hydride (as a 55% w/w dispersion in mineral oil) in 300 ml of dehydrated dimethylformamide, and the resulting mixture was stirred at room temperature for 30 minutes, after which 17.2 ml of methyl iodide were added at room temperature. The reaction mixture was stirred for 1 hour, after which it was allowed to stand overnight at room temperature. It was then concentrated to about one-fifth of its original volume by evaporation under reduced pressure. The concentrate was mixed with ice-water and the resulting aqueous mixture was extracted with ethyl acetate. The extract was washed with water and with a saturated aqueous solution of sodium chloride, in that order, after which it was dried over anhydrous sodium sulfate. On distilling off the solvent, there were obtained 52.1 g of the title compound, melting at 122°–124° C.

Preparation 8

N-Methyl-5-methoxy-2-nitroaniline 750 ml of a 4N solution of hydrogen chloride in 1,4-dioxane were added to 52 g of N-t-butoxycarbonyl-N-methyl-5-methoxy-2-nitroaniline (prepared as described in Preparation 7) at room temperature, and the resulting mixture was stirred for 2) hours. At the end of this time, the reaction mixture was freed from the solvent by distillation under reduced pressure, and the resulting residue was mixed with water and ethyl acetate. The mixture was then neutralized by the addition of sodium hydrogencarbonate, after which it was extracted with ethyl acetate. The extract was washed with a saturated aqueous solution of sodium chloride and dried over anhydrous sodium sulfate. On distilling off the solvent, there were obtained 35.3 g of the title compound, melting at 107°–110° C.

Preparation 9

5-Methoxy-N-methyl-1,2-phenylenediamine 346 g of stannous chloride were added to a mixture of 35 g of N-methyl-5-methoxy-2-nitroaniline (prepared as described in Preparation 8), 900 ml of t-butanol and 100 ml of ethyl acetate at room temperature, and the resulting mixture was stirred at 60° C. for 2 hours, after which 11 g of sodium borohydride were added in portions at 60° C. over a period of about 1 hour. The reaction mixture was then stirred at 60° C. for 3 hours, after which it was allowed to stand at room temperature for 2 days. It was then poured into ice-water and the aqueous mixture was neutralized by the addition of sodium hydrogencarbonate. The mixture was extracted with ethyl acetate, and the extract was washed with a saturated aqueous solution of sodium chloride and dried over anhydrous sodium sulfate. The solvent was removed from the mixture by distillation under reduced pressure, and the resulting residue was purified by column chromatography through silica gel using a 3:2 by volume mixture of ethyl acetate and hexane as the eluent, to give 21.9 g of the title compound having an Rf value=0.18 (on thin layer chromatography on silica gel; developing solvent: a 1:1 by volume mixture of ethyl acetate and hexane).

Preparation 10

Trimethylbenzoquinone

A suspension of 25.6 g of ferric chloride in 50 ml of water was added at room temperature to a solution of 20 g of trimethylhydroquinone in 150 ml of acetone, and the resulting mixture was stirred for 1 hour, after which it was allowed to stand for 2 days. At the end of this time, it was concentrated to about one half of its original volume, and the concentrate was mixed with water. The resulting aqueous mixture was extracted with ethyl acetate, and the extract was washed with water and with a saturated aqueous solution of sodium chloride, in that order, after which it was dried over anhydrous sodium sulfate. The solvent was removed by distillation under reduced pressure, and the resulting residue was purified by column chromatography through silica gel, using a 1:6 by volume mixture of ethyl acetate and hexane as the eluent, to give 16.9 g of the title compound having an Rf value=0.48 (on thin layer chromatography on silica gel; developing solvent: a 1:6 by volume mixture of ethyl acetate and hexane).

Preparation 11

2,3,6-Trimethylbenzoquinone-4-oxime

A solution of 7.04 g of hydroxylamine hydrochloride in 30 ml of water was added at room temperature to a solution of 16.9 g of trimethylbenzoquinone (prepared as described in Preparation 10) in 150 ml of methanol, and the resulting mixture was stirred for 2 hours, after which it was allowed to stand for 2 days. At the end of this time, the reaction mixture was diluted with 1000 ml of water. The precipitate which separated out was collected by filtration and recrystallized from a mixture of ethyl acetate and hexane, to give 11.2 g of the title compound, melting at 188°–190° C.

Preparation 12

4-Hydroxy-2,3,5-trimethylaniline 152 g of sodium hydrosulfite were added, whilst ice-cooling, to a mixture of 36.15 g of 2,3,6-trimethyl-benzoquinone-4-oxime (prepared as described in Preparation 11) and 880 ml of a 1N aqueous solution of sodium hydroxide, and the resulting mixture was stirred at room temperature for 1 hour, after which it was allowed to stand overnight. The reaction mixture was then poured into ice-water and the pH of the aqueous mixture was adjusted to a value of 4 to 5 by the addition of 5N aqueous hydrochloric acid, after which it was neutralized with sodium hydrogencarbonate. The mixture thus obtained was extracted with ethyl acetate. The extract was washed with a saturated aqueous solution of sodium chloride and dried over anhydrous sodium sulfate. The solvent was then removed by distillation under reduced pressure, after which the crystalline residue was triturated with diisopropyl ether and collected by filtration. On washing with diisopropyl ether, there were obtained 30.1 g of the title compound, melting at 131°–134° C.

Preparation 13

N-t-Butoxycarbonyl-4-hydroxy-2,3,5-trimethylaniline 22.0 ml of triethylamine were added at room temperature to a solution of 20 g of 4-hydroxy-2,3,5-trimethylaniline (prepared as described in Preparation 12) in 500 ml of tetrahydrofuran, followed by 34.6 g of di-t-butyl dicarbonate, and the resulting mixture was stirred for 6 hours, after which it was allowed to stand overnight. At the end of this time, the reaction mixture was freed from the solvent by distillation under reduced pressure, and the resulting residue was mixed with water. The resulting aqueous mixture was extracted with ethyl acetate. The extract was washed with a saturated aqueous solution of sodium chloride and dried over anhydrous sodium sulfate. The solvent was removed by distillation under reduced pressure, after which the crystalline residue was triturated with hexane, to give 31.9 g of the title compound, melting at 158°–161° C.

Preparation 14

N-Methyl-4-hydroxy-2,3,5-trimethylaniline

A solution of 15 g of N-t-butoxycarbonyl-4-hydroxy-2,3,5-trimethylaniline (prepared as described in Preparation 13) in 200 ml of dehydrated tetrahydrofuran was added to a suspension of 6.8 g of lithium aluminum hydride in 300 ml of dehydrated tetrahydrofuran, whilst ice-cooling, and the resulting mixture was stirred at room temperature for 3 hours, after which it was heated under reflux for 2 hours. At the end of this time, a mixture of 10 ml of water and 30 ml of tetrahydrofuran was added to the reaction mixture in order to destroy any excess of lithium aluminum hydride. The reaction mixture was then stirred at room temperature for 1.5 hours, after which insoluble materials were filtered off with the aid of a Celite (trade mark) filter aid. These materials were washed with ethyl acetate, and the ethyl acetate washings were combined and dried over anhydrous sodium sulfate. The solvent was removed by distillation under reduced pressure, and the resulting residue was purified by column chromatography through silica gel using a 1:3 by volume mixture of ethyl acetate and hexane as the eluent, to give 5.1 g of the title compound, melting at 120°–122° C.

Preparation 15

N-t-Butoxycarbonyl-N-methyl-4-hydroxy-2,3,5-trimethylaniline 5.0 ml of triethylamine and a solution of 7.92 g of di-t-butyl dicarbonate in 30 ml of tetrahydrofuran were added at room temperature to a solution of 5.0 g of N-methyl-4-hydroxy-2,3,5-trimethylaniline (prepared as described in Preparation 14) in 70 ml of tetrahydrofuran, and the resulting mixture was stirred for 1 hour, after which it was allowed to stand overnight. At the end of this time, the reaction mixture was freed from the solvent by distillation under reduced pressure, and the resulting residue was mixed with water. The aqueous mixture was extracted with ethyl acetate. The extract was washed with water and with a saturated aqueous solution of sodium chloride, in that order, after which it was dried over anhydrous magnesium sulfate. After distilling off the solvent, the residual crystals were triturated with hexane and collected by filtration. There were obtained 7.35 g of the title compound, melting at 163°–166° C.

Preparation 16

N-t-Butoxycarbonyl-N-methyl-4-acetoxy-2,3,5-trimethylaniline 5.64 ml of dehydrated triethylamine and 2.9 ml of acetyl chloride were added at room temperature to a solution of 7.2 g of N-t-butoxycarbonyl-N-methyl-4-hydroxy-2,3,5-trimethylaniline (prepared as described in Preparation 15) in 100 ml of dehydrated tetrahydrofuran, and the resulting mixture was stirred for 1 hour, after which it was allowed to stand overnight. The reaction mixture was then diluted with water and the aqueous mixture was extracted with ethyl acetate. The extract was washed with water and with a saturated aqueous solution of sodium chloride, in that order, after which it was dried over anhydrous magnesium sulfate. The solvent was removed by distillation under reduced pressure, after which the residue was triturated with ice-cooled hexane to cause crystallization. The crystals were collected by filtration and washed with ice-cooled hexane to give 6.25 g of the title compound, melting at 103°–104° C.

Preparation 17

N-Methyl-4-acetoxy-2,3,5-trimethylaniline hydrochloride

A mixture prepared by adding 100 ml of a 4N solution of hydrogen chloride in 1,4-dioxane to 5.45 g of N-t-butoxycarbonyl-N-methyl-4-acetoxy-2,3,5-trimethylaniline (prepared as described in Preparation 16) at room temperature was stirred for 3 hours. At the end of this time, the reaction mixture was freed from the solvent by distillation under reduced pressure, and the resulting residue was triturated with diisopropyl ether. The crystals thus obtained were collected by filtration, after which they were washed with diisopropyl ether to give 4.36 g of the title compound, melting at 172°–176° C.

Preparation 18

N-Methyl-4-acetoxy-2,3,5-trimethyl-6-nitroaniline 4.3 g of N-methyl-4-acetoxy-2,3,5-trimethylaniline hydrochloride (prepared as described in Preparation 17) were added to ice-cooled concentrated aqueous nitric acid, and the resulting mixture was stirred, whilst ice-cooling, for 10 minutes and then at room temperature for 10 minutes. At the end of this time, the reaction mixture was poured into ice-water and the aqueous mixture was neutralized by the addition of sodium hydrogencarbonate, after which it was extracted with ethyl acetate. The extract was washed with a saturated aqueous solution of sodium chloride and dried over anhydrous sodium sulfate. The solvent was then removed by distillation under reduced pressure, after which 50 ml of diisopropyl ether and 50 ml of hexane were added to the residue. The mixture was then agitated ultrasonically for 5 minutes. Insoluble precipitates were triturated with a 1:1 by volume mixture of diisopropyl ether and hexane. The resulting crystals were collected by filtration, after which they were washed with a 1:1 by volume mixture of diisopropyl ether and hexane to give 2.76 g of the title compound, melting at 143°–146° C.

Preparation 19

4-Acetoxy-N-methyl-3,5,6-trimethyl-1,2-phenylenediamine

A solution of 2.65 g of N-methyl-4-acetoxy-2,3,5-trimethyl-6-nitroaniline (prepared as described in Preparation 18) in a mixture of 20 ml ethanol and 20 ml of ethyl acetate was shaken at room temperature for 3.5 hours and then at 40° C. for 3 hours in an atmosphere of hydrogen and in the presence of 0.2 g of platinum oxide. At the end of this time, the reaction mixture was filtered to remove the platinum oxide and the filtrate was freed from the solvent by distillation under reduced pressure. The resulting residue was purified by column chromatography through silica gel, using a 1:1 by volume mixture of ethyl acetate and hexane as the eluent, to give 1.3 g of title compound, melting at 113°–116° C.

Preparation 20

5-(4-Methoxycarbonylmethoxybenzyl)-3-triphenylmethylthiazolidine-2,4-dione 126 g of cesium carbonate were added at room temperature to a solution of 120 g of 5-(4-hydroxybenzyl)-3- triphenylmethylthiazolidine-2,4-dione in 2.5 liters of acetone, followed by 36 ml of methyl bromoacetate, and the resulting mixture was stirred for 1 hour. At the end of this time, the reaction mixture was freed from the solvent by distillation under reduced pressure, and the resulting residue was mixed with water. The aqueous mixture was then extracted with ethyl acetate. The extract was washed with water and then with a saturated aqueous solution of sodium chloride, after which it was dried over anhydrous magnesium sulfate. The solvent was removed by distillation under reduced pressure, after which 1 liter of diethyl ether was added to the oily residue. The mixture was then agitated ultrasonically for 10 minutes. The solid substance precipitated was collected by filtration, to give 126.3 g of the title compound, melting at 158°–162° C.

Preparation 21

5-(4-Methoxycarbonylmethoxybenzyl)thiazolidine-2,4-dione 1700 ml of acetic acid and then 400 ml of water were added at room temperature to a suspension of 344 g of 5-(4-methoxycarbonylmethoxybenzyl)-3-triphenylmethylthiazolidine-2,4-dione (prepared as described in Preparation 20) in 400 ml of 1,4-dioxane and the resulting mixture was stirred for 5 hours at 80° C. At the end of this time, the reaction mixture was freed from the solvent by evaporation under reduced pressure, and the resulting residue was purified by column chromatography through silica gel using a 1:2 by volume mixture of ethyl acetate and hexane, a 2:1 by volume mixture of ethyl acetate and hexane and then ethyl acetate as eluents, to give 161.7 g of the title compound, melting at 100°–106° C.

Preparation 22

N-t-Butoxycarbonyl-4-methoxy-2-nitroaniline

A solution of 2.5 g of 4-methoxy-2-nitroaniline in 30 ml of dehydrated dimethylformamide was added at room temperature to a suspension of 0.72 g of sodium hydride (as a 55% w/w dispersion in mineral oil) in 30 ml of dehydrated dimethylformamide, and the resulting mixture was stirred at room temperature for 10 minutes, after which a solution of 3.57 g of di-t-butyl dicarbonate in 20 ml of dehydrated dimethylformamide was added at room temperature and then the mixture was stirred for 1 hour. At the end of this time, the reaction mixture was poured into ice-water and the resulting mixture was extracted with ethyl acetate. The extract was washed with water and then with a saturated aqueous solution of sodium chloride, after which it was dried over anhydrous sodium sulfate. The extract was freed from the solvent by distillation under reduced pressure, after which the resulting residue was purified by column chromatography through silica gel, using a 1:20 by volume mixture of ethyl acetate and hexane as the eluent, to give 1.94 g of the title compound having an Rf value=0.39 (on thin layer chromatography on silica gel; developing solvent: a 1:20 by volume mixture of ethyl acetate and hexane).

Preparation 23

N-t-Butoxycarbonyl-N-methyl-4-methoxy-2-nitroaniline

A procedure similar to that described in Preparation 7 was repeated, except that 0.46 g of sodium hydride (as a 55% w/w dispersion in mineral oil), 15 ml of dehydrated dimethylformamide, 0.66 ml of methyl iodide and a solution of 1.9 g of N-t-butoxycarbonyl-4-methoxy-2-nitroaniline (prepared as described in Preparation 22) in 15 ml of dehydrated dimethylformamide were used, to give 2.0 g of the title compound having an Rf value=0.34 (on thin layer chromatography on silica gel; developing solvent: a 1:5 by volume mixture of ethyl acetate and hexane).

Preparation 24

N-Methyl-4-methoxy-2-nitroaniline

A procedure similar to that described in Preparation 8 was repeated, except that 2.0 g of N-t-butoxycarbonyl-N-methyl-4-methoxy-2-nitroaniline (prepared as described in Preparation 23) and 30 ml of a 4N solution of hydrogen chloride in 1,4-dioxane were used, to give 1.17 g of the title compound having an Rf value=0.62 (on thin layer chromatography on silica gel; developing solvent: a 1:5 by volume mixture of ethyl acetate and hexane).

Preparation 25

4-Methoxy-N-methyl-1,2-phenylenediamine

A solution of 1.16 g of N-methyl-4-methoxy-2-nitroaniline (prepared as described in Preparation 24) in 50 ml of ethanol was shaken in an atmosphere of hydrogen and in the presence of 0.3 g of 10% w/w palladium-on-charcoal for 3 hours. At the end of this time, the palladium-on-charcoal was filtered off, and the filtrate was freed from the solvent by evaporation under reduced pressure, to give 1.17 g of the title compound having an Rf value=0.50 (on thin layer chromatography on silica gel; developing solvent: a 1:3 by volume mixture of ethyl acetate and hexane).

Preparation 26

Methyl 5-benzimidazolecarboxylate

A mixture of 10 g of 5-benzimidazolecarboxylic acid, 150 ml of methanol and 100 ml of a 4N solution of hydrogen chloride in 1,4-dioxane was agitated ultrasonically for 4 hours. At the end of this time, the solvent was removed by distillation under reduced pressure, after which 300 ml of methanol and 3.5 g of lithium borohydride were added to the residue and the mixture was stirred for 1 hour. The solvent was then removed by evaporation under reduced pressure and the residue was mixed with an aqueous solution of sodium chloride, after which it was extracted with ethyl acetate. The solvent was removed by distillation under reduced pressure, to give 5.44 g of the title compound, melting at 136°–138° C.

Preparation 27

Methyl 1-benzyl-5-benzimidazolecarboxylate

A mixture of 2.8 g of methyl 5-benzimidazolecarboxylate (prepared as described in Preparation 26), 3.52 g of benzyl bromide, 3 g of potassium carbonate and 50 ml of acetone was stirred for 3 days at room temperature. At the end of this time, the solvent was removed by evaporation under reduced pressure and the residue was mixed with an aqueous solution of sodium chloride, after which it was extracted with ethyl acetate. The extract was dried over anhydrous sodium sulfate, after which the solvent was removed by distillation under reduced pressure. The residue was then recrystallized from a mixture of ethyl acetate and hexane, to give 0.94 g of the title compound, melting at 156°–162° C.

Preparation 28

1-Benzyl-5-benzimidazolemethanol 0.87 g of methyl 1-benzyl-5-benzimidazolecarboxylate (prepared as described in Preparation 27) in 18 ml of dehydrated tetrahydrofuran were added to a suspension of 0.23 g of lithium aluminum hydride in 10 ml of dehydrated tetrahydrofuram, whilst ice-cooling, and the resulting mixture was stirred for 2 hours at room temperature. A further 0.11 g of lithium aluminum hydride and 10 ml of dehydrated tetrahydrofuran were then added to the reaction mixture and the mixture was stirred for 1 hour at room temperature and then for 4.5 hours at 50° C. in oil bath, after which it was heated under reflux for 2 hours. The reaction mixture was cooled to room temperature by allowing it to stand, after which sodium sulfate decahydrate was added to it in excess and the mixture was stirred for 2 hours at room temperature. At the end of this time, the reaction mixture was filtered with the aid of a Celite (trade mark) filter aid and the filtrate was freed from the solvent by distillation under reduced pressure. The residue was then recrystallized from a mixture of ethanol and diisopropyl ether, to give 383 mg of the title compound, melting at 148°–150° C.

Preparation 29

5-[4-(1-Benzylbenzimidazol-5-ylmethoxy)benzyl]-3-triphenylmethylthiazolidine-2,4-dione A mixture of 822 mg of 5-(4-hydroxybenzyl)-3-triphenylmethylthiazolidine-2,4-dione, 454 mg of azodicarbonyldipiperidine, 6 ml of dehydrated toluene and 0.44 ml of tributylphosphine was stirred for 30 minutes at room temperature. At the end of this time, 349 mg of 1-benzyl-5-benzimidazolemethanol were added to the reaction mixture and then the mixture was stirred for 3 hours, after which it was allowed to stand for 10 days at room temperature. The solvent was then removed by distillation under reduced pressure and the resulting residue was purified by column chromatography through silica gel using a gradient elution method, with mixtures of ethyl acetate and hexane in ratios ranging from 3:1 to 1:0 by volume as the eluent, to give 0.32 g of the title compound, softening at 90°–91° C.

Formulation 1

Powder preparation 4 g of 5-[4-(6-methoxy-1-methylbenzimidazol-2-ylmethoxy)benzyl]thiazolidine-2,4-dione (Compound No. 1-49), 10 g of polyvinylpyrrolidone and 0.5 g of hydroxypropylmethylcellulose (Commercial name: TC-5E; a product of Shin-Etsu Chemical Industry Co., Ltd.) are mixed and pulverized using a vibrating mill for 30 minutes to obtain the desired powder preparation.

Formulation 2

Capsule preparation 20 g of 5-[4-(6-methoxy-1-methylbenzimidazol-2-ylmethoxy)benzyl]thiazolidine-2,4-dione (Compound No. 1-49) and 20 g of polyvinylpyrrolidone are dissolved in a mixture of 100 g of acetone and 100 g of ethanol, and then the solution is sprayed onto 200 g of cross-carmellose sodium, using a fluidized bed granulator, to obtain granules. 0.1 g of hydroxypropylmethylcellulose (Commercial name: TC-5E; a product of Shin-Etsu Chemical Industry Co., Ltd.) and 1.9 g of lactose are then added to 10 g of these granules and mixed. A gelatin capsule is then filled with 0.24 g of this mixture, to obtain a capsule preparation. The capsule preparation contains 0.1 g of the active compound per capsule.

Formulation 3

Tablet preparation 1 g of 5-[4-(6-methoxy-1-methylbenzimidazol-2-ylmethoxy)benzyl]thiazolidine-2,4-dione (Compound No. 1-49) and 1 g of polyvinylpyrrolidone are dissolved in a mixture of 5 g of acetone and 5 g of ethanol, and then using a rotary evaporator, the organic solvent is removed by evaporation under reduced pressure. The resulting solid matter is pulverized, to obtain fine granules. 0.25 g of crystalline cellulose, 0.25 g of low-substituted hydroxypropylcellulose, 0.05 g of hydroxypropylmethylcellulose (Commercial name: TC-5E; a product of Shin-Etsu Chemical Industry Co., Ltd.), 0.18 g of lactose and 0.2 g of magnesium stearate are added to 1 g of these fine granules and mixed. Tablets are then prepared using a tableting machine.

We claim:

1. A compound of formula (I):

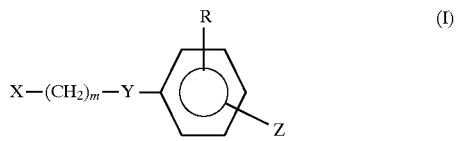

wherein:

X represents a benzimidazole group which is unsubstituted or is substituted by at least one substituent selected from the group consisting of substituents α, defined below;

Y represents an oxygen atom or a sulfur atom;

Z represents a group of formula (i), (ii), (iii), (iv) or (v):

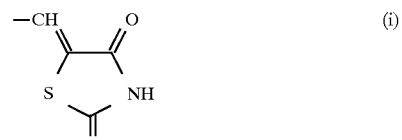

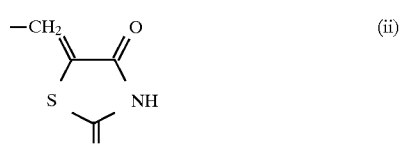

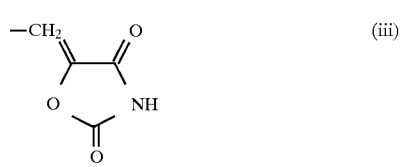

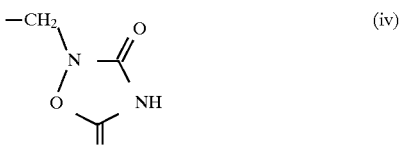

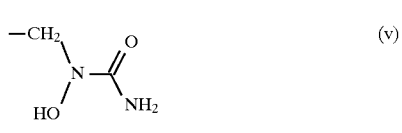

R represents:
  a hydrogen atom;
  an alkyl group having from 1 to 4 carbon atoms;
  an alkoxy group having from 1 to 4 carbon atoms;

a halogen atom;
a hydroxy group;
a nitro group;
a group of formula —NR$^a$R$^b$,
  in which R$^a$ and R$^b$ are the same or different and each represents a hydrogen atom, an alkyl group having from 1 to 8 carbon atoms, an aralkyl group in which an alkyl group having from 1 to 5 carbon atoms is substituted by a carbocyclic aryl group having from 6 to 10 carbon atoms; a carbocyclic aryl group having from 6 to 10 carbon atoms; an aliphatic acyl group having from 1 to 11 carbon atoms; an aryl-aliphatic acyl group in which an aliphatic acyl group having from 2 to 6 carbon atoms is substituted by at least one carbocyclic aryl group having from 6 to 10 carbon atoms; or an aromatic acyl group having from 7 to 11 carbon atoms; or
an aralkyl group in which an alkyl group having from 1 to 5 carbon atoms is substituted by a carbocyclic aryl group having from 6 to 10 carbon atoms; and
m represents an integer from 1 to 5;
said substituents α are selected from the group consisting of:
  an alkyl group having from 1 to 4 carbon atoms;
  an alkoxy group having from 1 to 4 carbon atoms;
  a benzyloxy group;
  a halogen atom;
  a hydroxy group;
  an acetoxy group;
  a phenylthio group;
  an alkylthio group having from 1 to 4 carbon atoms;
  a trifluoromethyl group;
  a nitro group;
  a group of formula —NR$^a$R$^b$, in which R$^a$ and R$^b$ are as defined above;
  a carbocyclic aryl group having from 6 to 10 carbon atoms which is unsubstituted or is substituted by at least one substituent selected from the group consisting of substituents β, defined below; or
  an aralkyl group in which an alkyl group having from 1 to 5 carbon atoms is substituted by a carbocyclic aryl group which has from 6 to 10 carbon atoms and which is unsubstituted or is substituted by at least one substituent selected from the group consisting of substituents β, defined below;
said substituents β are selected from the group consisting of alkyl groups having from 1 to 4 carbon atoms, alkoxy groups having from 1 to 4 carbon atoms, halogen atoms, hydroxy groups, nitro groups, phenyl groups, trifluoromethyl groups and groups of formula —NR$^a$R$^b$, in which R$^a$ and R$^b$ are as defined above;
and salts thereof.

2. The compound of claim 1, wherein X represents a benzimidazole group, which is unsubstituted or is substituted by from 1 to 5 of a substituent selected from the group consisting of
  an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$,
  wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms,
  an aryl group having from 6 to 10 carbon atoms which is unsubstituted or is substituted by at least one substituent selected from the group consisting of substituents β,
    said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above;
  and an aralkyl group having from 7 to 11 carbon atoms which is unsubstituted or is substituted by at least one substituent selected from the group consisting of substituents β.

3. The compound of claim 1, wherein R represents a hydrogen atom, an alkyl group having from 1 to 4 carbon atoms, an alkoxy group having from 1 to 4 carbon atoms or a halogen atom.

4. The compound of claim 1, wherein:
X represents a benzimidazole group, which is unsubstituted or is substituted by from 1 to 5 of a substituent selected from the group consisting of
  an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$,
  wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms,
  an aryl group having from 6 to 10 carbon atoms which is unsubstituted or is substituted by at least one substituent selected from the group consisting of substituents β,
    said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above;
  and an aralkyl group having from 7 to 11 carbon atoms which is unsubstituted or is substituted by at least one substituent selected from the group consisting of substituents β; and
R represents a hydrogen atom, an alkyl group having from 1 to 4 carbon atoms, an alkoxy group having from 1 to 4 carbon atoms or a halogen atom.

5. The compound of claim 1, wherein Y represents an oxygen atom.

6. The compound of claim 1, wherein Z represents a 2,4-dioxothiazolidin-5-ylidenylmethyl, 2,4-dioxothiazolidin-5-ylmethyl or 2,4,-dioxooxazolidin-5-ylmethyl group.

7. The compound of claim 1, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, and an aralkyl group having from 7 to 11 carbon atoms which is unsubstituted or is substituted by at least one substituent selected from the group consisting of substituents β;

Y represents an oxygen atom;

Z represents a 2,4-dioxothiazolidin-5-ylidenylmethyl, 2,4-dioxothiazalidin-5-ylmethyl or 2,4,-dioxooxazolidin-5-ylmethyl group; and R represents a hydrogen atom, an alkyl group having from 1 to 4 carbon atoms, an alkoxy group having from 1 to 4 carbon atoms or a halogen atom.

8. The compound of claim 1, wherein X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, and an aralkyl group having from 7 to 11 carbon atoms which is unsubstituted or is substituted by from 1 to 3 substituents selected from the group consisting of substituents β.

9. The compound of claim 1, wherein Z represents a 2,4-dioxothiazolidin-5-ylidenylmethyl or 2,4-dioxothiazolidin-5-ylmethyl group.

10. The compound of claim 1, wherein R represents a hydrogen atom, a methyl group, a methoxy group, an ethoxy group, a fluorine atom or a chlorine atom.

11. The compound of claim 1, wherein m represents an integer from 1 to 3.

12. The compound of claim 1, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, and an aralkyl group having from 7 to 11 carbon atoms which is unsubstituted or is substituted by from 1 to 3 substituents selected from the group consisting of substituents β;

Y represents an oxygen atom;

Z represents a 2,4-dioxothiazolidin-5-ylidenylmethyl or 2,4-dioxothiazolidin-5-ylmethyl group;

R represents a hydrogen atom, a methyl group, a methoxy group, an ethoxy group, a fluorine atom or a chlorine atom; and m represents an integer from 1 to 3.

13. The compound of claim 1, wherein X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group, a hydroxy group, an acetoxy group, a benzyl group and a phenyl group.

14. The compound of claim 1, wherein Z represents a 2,4-dioxothiazolidin-5-ylmethyl group.

15. The compound of claim 1, wherein R represents a hydrogen atom, a methyl group or a methoxy group.

16. The compound of claim 1, wherein:
X represents a benzimidazole group, which is unsubstituted or is substituted by from 1 to 5 of a substituent selected from the group consisting of
an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group, a hydroxy group, an acetoxy group, a benzyl group and a phenyl group;
Y represents an oxygen atom;
Z represents a 2,4-dioxothiazolidin-5-ylmethyl group;
R represents a hydrogen atom, a methyl group or a methoxy group; and
m represents an integer from 1 to 3.

17. The compound of claim 1, wherein X represents a benzimidazole group, which is unsubstituted or is substituted by from 1 to 5 of a substituent selected from the group consisting of
a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group and a phenyl group.

18. The compound of claim 1, wherein R represents a hydrogen atom.

19. The compound of claim 1, wherein m represents the integer 1 or 2.

20. The compound of claim 1, wherein:
X represents a benzimidazole group, which is unsubstituted or is substituted by from 1 to 5 of a substituent selected from the group consisting of
a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group and a phenyl group;
Y represents an oxygen atom;
Z represents a 2,4-dioxothiazolidin-5-ylmethyl group;
R represents a hydrogen atom; and
m represents the integer 1 or 2.

21. The compound of claim 1, wherein X represents a benzimidazole group, which is unsubstituted or is substituted by from 1 to 5 of a substituent selected from the group consisting of
a methyl group, a methoxy group, a hydroxy group, a benzyl group and an acetoxy group.

22. The compound of claim 1, wherein m represents the integer 1.

23. The compound of claim 1, wherein:
X represents a benzimidazole group, which is unsubstituted or is substituted by from 1 to 5 of a substituent selected from the group consisting of
a methyl group, a methoxy group, a hydroxy group, a benzyl group and an acetoxy group;
Y represents an oxygen atom;
Z represents a 2,4-dioxothiazolidin-5-ylmethyl group;
R represents a hydrogen atom; and
m represents the integer 1.

24. The compound of claim 1, selected from the group consisting of 5-[4-(1-methylbenzimidazol-2-ylmethoxy) benzyl]thiazolidine-2,4-dione and pharmaceutically acceptable salts thereof.

25. The compound of claim 1, selected from the group consisting of 5-[4-(6-methoxy-1-methylbenzimidazol-2-ylmethoxy)benzyl]thiazolidine-2,4-dione and pharmaceutically acceptable salts thereof.

26. The compound of claim 1, selected from the group consisting of 5-[4-(5-methoxy-1-methylbenzimidazol-2-ylmethoxy)benzyl]thiazolidine-2,4-dione and pharmaceutically acceptable salts thereof.

27. The compound of claim 1, selected from the group consisting of 5-[4-(1-benzylbenzimidazol-5-ylmethoxy) benzyl]thiazolidine-2,4-dione and pharmaceutically acceptable salts thereof.

28. The compound of claim 1, selected from the group consisting of 5-[4-(5-hydroxy-1,4,6,7-tetramethylbenzimidazol-2-ylmethoxy)benzyl]thiazolidine-2,4-dione and pharmaceutically acceptable salts thereof.

29. The compound of claim 1, selected from the group consisting of 5-[4-(5-acetoxy-1,4,6,7-tetramethylbenzimidazol-2-ylmethoxy)benzyl]thiazolidine-2,4-dione and pharmaceutically acceptable salts thereof.

30. The compound of claim 1, wherein Z is selected from the group consisting of

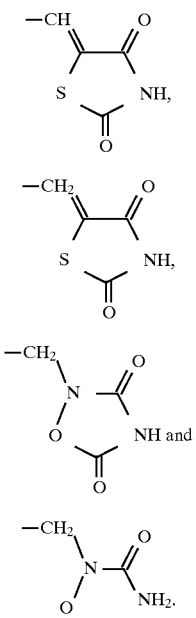

31. The compound of claim 1, wherein Y is a sulfur atom.

32. A pharmaceutical composition for the treatment or prophylaxis of insulin resistance, diabetes, hyperglycemia, arteriosclerosis, cataracts, hyperlipemia, obesity, impaired glucose tolerance, hypertension, polycystic ovary syndrome, gestational diabetes mellitus or insulin resistant non-IGT, and complications thereof, or for the inhibition of aldose reductase, 5-lipoxygenase or lipid peroxide, and complications thereof, which composition comprises an effective amount of an active compound in admixture with a pharmaceutically acceptable carrier or diluent, wherein said active compound is selected from the group consisting of compounds of formula (I):

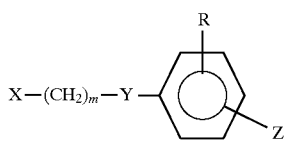

wherein:
X represents a benzimidazole group which is unsubstituted or is substituted by at least one substituent selected from the group consisting of a substituent α, defined below;
Y represents an oxygen atom or a sulfur atom;
Z represents a group of formula (i), (ii), (iii), (iv) or (v):

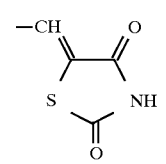

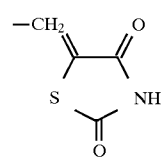

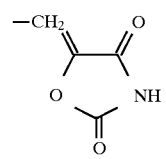

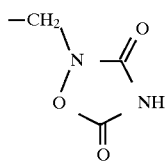

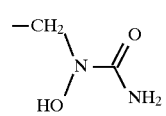

R represents:
a hydrogen atom;
an alkyl group having from 1 to 4 carbon atoms;
an alkoxy group having from 1 to 4 carbon atoms;
a halogen atom;
a hydroxy group;
a nitro group;
a group of formula —NR$^a$R$^b$,
in which R$^a$ and R$^b$ are the same or different and each represents a hydrogen atom, an alkyl group having from 1 to 8 carbon atoms, an aralkyl group in which an alkyl group having from 1 to 5 carbon atoms is substituted by a carbocyclic aryl group having from 6 to 10 carbon atoms; a carbocyclic aryl group having from 6 to 10 carbon atoms; an aliphatic acyl group having from 1 to 11 carbon atoms; an aryl-aliphatic acyl group in which an aliphatic acyl group having from 2 to 6 carbon atoms is substituted by at least one carbocyclic aryl group having from 6 to 10 carbon atoms; or an aromatic acyl group having from 7 to 11 carbon atoms; or an aralkyl group in which an alkyl group having from 1 to 5 carbon atoms is substituted by a carbocyclic aryl group having from 6 to 10 carbon atoms; and
m represents an integer from 1 to 5;
said substituents 2 are selected from the group consisting of:
an alkyl group having from 1 to 4 carbon atoms;
an alkoxy group having from 1 to 4 carbon atoms;
a benzyloxy group;
a halogen atom;
a hydroxy group;
an acetoxy group;
a phenylthio group;
an alkylthio group having from 1 to 4 carbon atoms;
a trifluoromethyl group;
a nitro group;
a group of formula —NR$^a$R$^b$, in which R$^a$ and R$^b$ are as defined above;
a carbocyclic aryl group having from 6 to 10 carbon atoms which is unsubstituted or is substituted by at least one substituent selected from the group consisting of substituents β, defined below; or
an aralkyl group in which an alkyl group having from 1 to 5 carbon atoms is substituted by a carbocyclic aryl group which has from 6 to 10 carbon atoms and which is unsubstituted or is substituted by at least one substituent selected from the group consisting of substituents β, defined below;
said substituents β are selected from the group consisting of alkyl groups having from 1 to 4 carbon atoms, alkoxy groups having from 1 to 4 carbon atoms, halogen atoms, hydroxy groups, nitro groups, phenyl groups, trifluoromethyl groups and groups of formula —NR$^a$R$^b$, in which R$^a$ and R$^b$ are as defined above;
and salts thereof.

33. The composition of claim 29, wherein X represents a benzimidazole group, which is unsubstituted or is substituted by from 1 to 5 of a substituent selected from the group consisting of
an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$,
wherein R$^a$ and R$^b$ are the same or different and each represents a hydrogen atom, an alkyl group having from 1 to a carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms,
an aryl group having from 6 to 10 carbon atoms which is unsubstituted or is substituted by at least one substituent selected from the group consisting of substituents β,
said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above;
and an aralkyl group having from 7 to 11 carbon atoms which is unsubstituted or is substituted by at least one substituent selected from the group consisting of substituents β.

34. The composition of claim 32, wherein R represents a hydrogen atom, an alkyl group having from 1 to 4 carbon atoms, an alkoxy group having from 1 to 4 carbon atoms or a halogen atom.

35. The composition of claim 32, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an arylaliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above;

and an aralkyl group having from 7 to 11 carbon atoms which is unsubstituted or is substituted by at least one substituent selected from the group consisting of substituents β; and R represents a hydrogen atom, an alkyl group having from 1 to 4 carbon atoms, an alkoxy group having from 1 to 4 carbon atoms or a halogen atom.

36. The composition of claim 32, wherein Y represents an oxygen atom.

37. The composition of claim 32, wherein Z represents a 2,4-dioxothiazolidin-5-ylidenylmethyl, 2,4-dioxothiazolidin-5-ylmethyl or 2,4,-dioxooxazolidin-5-ylmethyl group.

38. The composition of claim 32, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to a carbon atoms, an aralkyl group having from 7 to 11 carbon atoms, an aryl group having from 6 to 10 carbon atoms, an aliphatic acyl group having from 1 to 11 carbon atoms, an arylaliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, and an aralkyl group having from 7 to 11 carbon atoms which is unsubstituted or is substituted by at least one substituent selected from the group consisting of substituents β;

Y represents an oxygen atom;

Z represents a 2,4-dioxothiazolidin-5-ylidenylmethyl, 2,4-dioxothiazolidin-5-ylmethyl or 2,4,-dioxooxazolidin-5-ylmethyl group; and R represents a hydrogen atom, an alkyl group having from 1 to 4 carbon atoms, an alkoxy group having from 1 to 4 carbon atoms or a halogen atom.

39. The composition of claim 32, wherein X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, and an aralkyl group having from 7 to 11 carbon atoms which is unsubstituted or is substituted by from 1 to 3 substituents selected from the group consisting of substituents β.

40. The composition of claim 32, wherein Z represents a 2,4-dioxothiazolidin-5-ylidenylmethyl or 2,4-dioxothiazolidin-5-ylmethyl group.

41. The composition of claim 32, wherein R represents a hydrogen atom, a methyl group, a methoxy group, an ethoxy group, a fluorine atom or a chlorine atom.

42. The composition of claim 32, wherein m represents an integer from 1 to 3.

43. The composition of claim 32, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, and an aralkyl group having from 7 to 11 carbon atoms which is unsubstituted or is substituted by from 1 to 3 substituents selected from the group consisting of substituents β;

Y represents an oxygen atom;

Z represents a 2,4-dioxothiazolidin-5-ylidenylmethyl or 2,4-dioxothiazolidin-5-ylmethyl group;

R represents a hydrogen atom, a methyl group, a methoxy group, an ethoxy group, a fluorine atom or a chlorine atom; and m represents an integer from 1 to 3.

44. The composition of claim 32, wherein X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group, a hydroxy group, an acetoxy group, a benzyl group and a phenyl group.

45. The composition of claim 32, wherein Z represents a 2,4-dioxothiazolidin-5-ylmethyl group.

46. The composition of claim 32, wherein R represents a hydrogen atom, a methyl group or a methoxy group.

47. The composition of claim 32, wherein:

X represents a benzimidazole group, which is unsubstituted or is substituted by from 1 to 5 of a substituent selected from the group consisting of
an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group, a hydroxy group, an acetoxy group, a benzyl group and a phenyl group;

Y represents an oxygen atom;

Z represents a 2,4-dioxothiazolidin-5-ylmethyl group;

R represents a hydrogen atom, a methyl group or a methoxy group; and m represents an integer from 1 to 3.

48. The composition of claim 32, wherein X represents a benzimidazole group, which is unsubstituted or is substituted by from 1 to 5 of a substituent selected from the group consisting of a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group and a phenyl group.

49. The composition of claim 32, wherein R represents a hydrogen atom.

50. The composition of claim 32, wherein m represents the integer 1 or 2.

51. The composition of claim 32, wherein:

X represents a benzimidazole group, which is unsubstituted or is substituted by from 1 to 5 of a substituent selected from the group consisting of
a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group and a phenyl group;

Y represents an oxygen atom;

Z represents a 2,4-dioxothiazolidin-5-ylmethyl group;

R represents a hydrogen atom; and m represents the integer 1 or 2.

52. The composition of claim 32, wherein X represents a benzimidazole group, which is unsubstituted or is substituted by from 1 to 5 of a substituent selected from the group consisting of a methyl group, a methoxy group, a hydroxy group, a benzyl group and an acetoxy group.

53. The composition of claim 32, wherein m represents the integer 1.

54. The composition of claim 32, wherein:

X represents a benzimidazole group, which is unsubstituted or is substituted by from 1 to 5 of a subtituent selected from the group consisting of
a methyl group, a methoxy group, a hydroxy group, a benzyl group and an acetoxy group;

Y represents an oxygen atom;

Z represents a 2,4-dioxothiazolidin-5-ylmethyl group;

R represents a hydrogen atom; and m represents the integer 1.

55. The composition of claim 32, wherein said active compound is selected from the group consisting of:

5-[4-(1-Methylbenzimidazol-2-ylmethoxy)benzyl]thiazolidine-2,4-dione;

5-[4-(6-Methoxy-1-methylbenzimidazol-2-ylmethoxy)benzyl]thiazolidine-2,4-dione;

5-[4-(5-Methoxy-1-methylbenzimidazol-2-ylmethoxy)benzyl]thiazolidine-2,4-dione;

5-[4-(1-Benzylbenzimidazol-5-ylmethoxy)benzyl]thiazolidine-2,4-dione;

5-[4-(5-Hydroxy-1,4,6,7-tetramethylbenzimidazol-2-ylmethoxy)benzyl]thiazolidine-2,4-dione; and 5-[4-(5-Acetoxy-1,4,6,7-tetramethylbenzimidazol-2-ylmethoxy)benzyl]thiazolidine-2,4-dione;

and pharmaceutically acceptable salts thereof.

56. A method for the treatment or prophylaxis of insulin resistance, diabetes, hyperglycemia, arteriosclerosis, hyperlipemia, obesity, impaired glucose tolerance, hypertension, polycystic ovary syndrome, gestational diabetes mellitus or insulin resistant non-IGT, cataracts and complications thereof in a mammal, which may be human, which method comprises administering to said mammal an effective amount of an active compound, wherein said active compound is selected from the group consisting of compounds of formula (I):

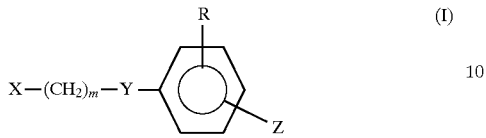

wherein:
X represents a benzimidazole group which is unsubstituted or is substituted by at least one substituent selected from the group consisting of substituents α, defined below;
Y represents an oxygen atom or a sulfur atom;
Z represents a group of formula (i), (ii), (iii), (iv) or (v):

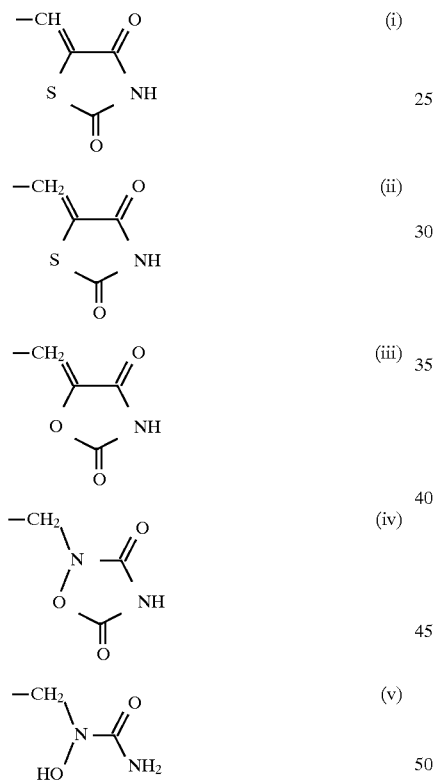

R represents:
a hydrogen atom;
an alkyl group having from 1 to 4 carbon atoms;
an alkoxy group having from 1 to 4 carbon atoms;
a halogen atom;
a hydroxy group;
a nitro group;
a group of formula —$NR^aR^b$,
in which $R^a$ and $R^b$ are the same or different and each represents a hydrogen atom, an alkyl group having from 1 to 8 carbon atoms, an aralkyl group in which an alkyl group having from 1 to 5 carbon atoms is substituted by a carbocyclic aryl group having from 6 to 10 carbon atoms; a carbocyclic aryl group having from 6 to 10 carbon atoms; an aliphatic acyl group having from 1 to 11 carbon atoms; an aryl-aliphatic acyl group in which an aliphatic acyl group having from 2 to 6 carbon atoms is substituted by at least one carbocyclic aryl group having from 6 to 10 carbon atoms; or an aromatic acyl group having from 7 to 11 carbon atoms; or
an aralkyl group in which an alkyl group having from 1 to 5 carbon atoms is substituted by a carbocyclic aryl group having from 6 to 10 carbon atoms; and
m represents an integer from 1 to 5;
said substituents a are selected from the group consisting of:
an alkyl group having from 1 to 4 carbon atoms;
an alkoxy group having from 1 to 4 carbon atoms;
a benzyloxy group;
a halogen atom;
a hydroxy group;
an acetoxy group;
a phenylthio group;
an alkylthio group having from 1 to 4 carbon atoms;
a trifluoromethyl group;
a nitro group;
a group of formula —$NR^aR^b$, in which $R^a$ and $R^b$ are as defined above;
a carbocyclic aryl group having from 6 to 10 carbon atoms which is unsubstituted or is substituted by at least one substituent selected from the group consisting of substituents β, defined below; or
an aralkyl group in which an alkyl group having from 1 to 5 carbon atoms is substituted by a carbocyclic aryl group which has from 6 to 10 carbon atoms and which is unsubstituted or is substituted by at least one substituent selected from the group consisting of substituents β, defined below;
said substituents β are selected from the group consisting of alkyl groups having from 1 to 4 carbon atoms, alkoxy groups having from 1 to 4 carbon atoms, halogen atoms, hydroxy groups, nitro groups, phenyl groups, trifluoromethyl groups and groups of formula —$NR^aR^b$, in which $R^a$ and $R^b$ are as defined above;
and salts thereof.

57. The method of claim 56, wherein X represents a benzimidazole group, which is unsubsittuted or is substituted by from 1 to 5 of a substituent selected from the group consisting of
an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$,
wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β,
said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above;

and an aralkyl group having from 7 to 11 carbon atoms which is unsubstituted or is substituted by at least one substituent selected from the group consisting of substituents β.

58. The method of claim 56, wherein R represents a hydrogen atom, an alkyl group having from 1 to 4 carbon atoms, an alkoxy group having from 1 to 4 carbon atoms or a halogen atom.

59. The method of claim 56, wherein:

X represents a benzimidazole group, which is unsubstituted or is substituted by from 1 to 5 of a substituent selected from the group consisting of
an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$,
wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms,
an aryl group having from 6 to 10 carbon atoms which is unsubstituted or is substituted by at least one substituent selected from the group consisting of substituents β,
said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above;
and an aralkyl group having from 7 to 11 carbon atoms which is unsubstituted or is substituted by at least one substituent selected from the group consisting of substituents β; and
R represents a hydrogen atom, an alkyl group having from 1 to 4 carbon atoms, an alkoxy group having from 1 to 4 carbon atoms or a halogen atom.

60. The method of claim 54, wherein Y represents an oxygen atom.

61. The method of claim 56, wherein Z represents a 2,4-dioxothiazolidin-5-ylidenylmethyl, 2,4-dioxothiazolidin-5-ylmethyl or 2,4,-dioxooxazolidin-5-ylmethyl group.

62. The method of claim 56, wherein:

X represents a benzimidazole group, which is unsubstituted or is substituted by from 1 to 5 of a substituent selected from the croup consisting of
an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$,
wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-
aliphatic acyl group having from 8 to 12 carbon atoms or an aromatic acyl group having from 7 to 11 carbon atoms,
an aryl group having from 6 to 10 carbon atoms which is unsubstituted or is substituted by at least one substituent selected from the group consisting of substituents β,
substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above,
and an aralkyl group having from 7 to 11 carbon atoms which is unsubstituted or is substituted by at least one substituent selected from the group consisting of substituents β;

Y represents an oxygen atom;

Z represents a 2,4-dioxothiazolidin-5-ylidenylmethyl, 2,4-dioxothiazolidin-5-ylmethyl or 2,4,-dioxooxazolidin-5-ylmethyl group; and R represents a hydrogen atom, an alkyl group having from 1 to 4 carbon atoms, an alkoxy group having from 1 to 4 carbon atoms or a halogen atom.

63. The method of claim 56, wherein X represents a benzimidazole group, which is unsubstituted or is substituted by from 1 to 5 of substituent selected from the group consisting of
an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$,
wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-alphatic acyl group having from 8 to 12 carbon atoms or an aromatic acyl group having from 7 to 11 carbon atoms,
an aryl group having from 6 to 10 carbon atoms which is unsubstituted or is substituted by from 1 to 3 substituents selected from the group consisting of substituents β,
substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above,
and an aralkyl group having from 7 to 11 carbon atoms which is unsubstituted or is substituted by from 1 to 3 substituents selected from the group consisting of substituents β.

64. The method of claim 56, wherein Z represents a 2,4-dioxothiazolidin-5-ylidenylmethyl or 2,4-dioxothiazolidin-5-ylmethyl group.

65. The method of claim 56, wherein R represents a hydrogen atom, a methyl group, a methoxy group, an ethoxy group, a fluorine atom or a chlorine atom.

66. The method of claim 56, wherein m represents an integer from 1 to 3.

67. The method of claim 56, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —$NR^aR^b$, wherein $R^a$ and $R^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —$NR^aR^b$, wherein $R^a$ and $R^b$ are as defined above, or an aralkyl group having from 7 to 11 carbon atoms which is unsubstituted or is substituted by from 1 to 3 substituents selected from the group consisting of substituents β;

Y represents an oxygen atom;

Z represents a 2,4-dioxothiazolidin-5-ylidenylmethyl or 2,4-dioxothiazolidin-5-ylmethyl group;

R represents a hydrogen atom, a methyl group, a methoxy group, an ethoxy group, a fluorine atom or a chlorine atom; and m represents an integer from 1 to 3.

68. The method of claim 56, wherein X represents a benzimidazole group, which is unsubstituted or is substituted by from 1 to 5 of a substituent selected from the croup consisting of an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group, a hydroxy group, an acetoxy group, a benzyl group and a phenyl group.

69. The method of claim 56, wherein Z represents a 2,4-dioxothiazolidin-5-ylmethyl group.

70. The method of claim 56, wherein R represents a hydrogen atom, a methyl group or a methoxy group.

71. The method of claim 56, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group, a hydroxy group, an acetoxy group, a benzyl group and a phenyl group;

Y represents an oxygen atom;

Z represents a 2,4-dioxothiazolidin-5-ylmethyl group;

R represents a hydrogen atom, a methyl group or a methoxy group; and m represents an integer from 1 to 3.

72. The method of claim 56, wherein X represents a benzimidazole group, which is unsubstituted or is substituted by from 1 to 5 of a substituent selected from the group consisting of a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group and a phenyl group.

73. The method of claim 56, wherein R represents a hydrogen atom.

74. The method of claim 56, wherein m represents the integer 1 or 2.

75. The method of claim 56, wherein:

X represents a benzimidazole group, which is unsubstituted or is substituted by from 1 to 5 of a substituent selected from the group consisting of a methyl group, an substituent α'" represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group and a phenyl group;

Y represents an oxygen atom;

Z represents a 2,4-dioxothiazolidin-5-ylmethyl group;

R represents a hydrogen atom; and m represents the integer 1 or 2.

76. The method of claim 56, wherein X represents a benzimidazole group, which is unsubstituted or is substituted by from 1 to 5 of a substituent selected from the group consisting of a methyl group, a methoxy group, a hydroxy group, a benzyl group and an acetoxy group.

77. The method of claim 56, wherein m represents the integer 1.

78. The method of claim 56, wherein:

X represents a benzimidazole group, which is unsubstituted or is substituted by from 1 to 5 of a substituent; selected from the group consisting of a methyl group, a methoxy group, a hydroxy group, a benzyl group and an acetoxy group;

Y represents an oxygen atom;

Z represents a 2,4-dioxothiazolidin-5-ylmethyl group;

R represents a hydrogen atom; and m represents the integer 1.

79. The method of claim 56, wherein said active compound is selected from the group consisting of:

5-[4-(1-Methylbenzimidazol-2-ylmethoxy)benzyl] thiazolidine-2,4-dione;

5-[4-(6-Methoxy-1-methylbenzimidazol-2-ylmethoxy) benzyl]thiazolidine-2,4-dione;

5-[4-(5-Methoxy-1-methylbenzimidazol-2-ylmethoxy) benzyl]thiazolidine-2,4-dione;

5-[4-(1-Benzylbenzimidazol-5-ylmethoxy)benzyl] thiazolidine-2,4-dione;

5-[4-(5-Hydroxy-1,4,6,7-tetramethylbenzimidazol-2-ylmethoxy)benzyl]thiazolidine-2,4-dione; and 5-[4-(5-Acetoxy-1,4,6,7-tetramethylbenzimidazol-2-ylmethoxy)benzyl]thiazolidine-2,4-dione;
and pharmaceutically acceptable salts thereof.

80. The method of claim 56, wherein the method is for the treatment or prophylaxis of insulin resistance.

81. The method of claim 56, wherein the method is for the treatment or prophylaxis of diabetes.

82. The method of claim 56, wherein the method is for the treatment or prophylaxis of hyperglycemia.

83. The method of claim 56, wherein the method is for the treatment or prophylaxis of arteriosclerosis.

84. The method of claim 56, wherein the method is for the treatment or prophylaxis of cataracts.

85. The method of claim 56, wherein the method is for the treatment or prophylaxis of hyperlipemia.

86. The method of claim 56, wherein the method is for the treatment or prophylaxis of obesity.

87. The method of claim 56, wherein the method is for the treatment or prophylaxis of impaired glucose tolerance.

88. The method of claim 56, wherein the method is for the treatment or prophylaxis of hypertension.

89. The method of claim 56, wherein the method is for the treatment or prophylaxis of polycystic ovary syndrome.

90. The method of claim 56, wherein the method is for the treatment or prophylaxis of gestational diabetes mellitus.

91. The method of claim 56, wherein the method is for the treatment or prophylaxis of insulin resistance non-IGT.

92. The method of claim 56, wherein the method is for the treatment or prophylaxis of diabetes complications.

93. A method for the inhibition of aldose reductase, 5-lipoxygenase or lipid peroxide, and complications thereof in a mammal, which may be human, which method comprises administering to said mammal an effective amount of an active compound, wherein said active compound is selected from the group consisting of compounds of formula (I):

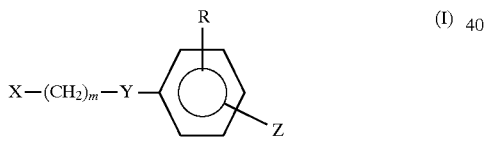

wherein:
X represents a benzimidazole group which is unsubstituted or is substituted by at least one substituent selected from the group consisting of substituents α, defined below;
Y represents an oxygen atom or a sulfur atom;
Z represents a group of formula (i), (ii), (iii), (iv) or (v):

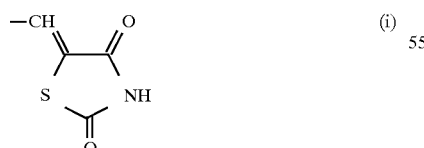

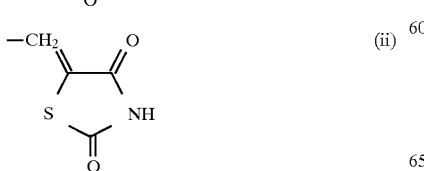

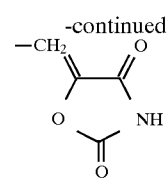

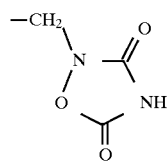

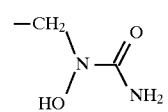

R represents:
a hydrogen atom;
an alkyl group having from 1 to 4 carbon atoms;
an alkoxy group having from 1 to 4 carbon atoms;
a halogen atom;
a hydroxy group;
a nitro group;
a group of formula —NR$^a$R$^b$,
in which R$^a$ and R$^b$ are the same or different and each represents a hydrogen atom, an alkyl group having from 1 to 8 carbon atoms, an aralkyl group in which an alkyl group having from 1 to 5 carbon atoms is substituted by a carbocyclic aryl group having from 6 to 10 carbon atoms; a carbocyclic aryl group having from 6 to 10 carbon atoms; an aliphatic acyl group having from 1 to 11 carbon atoms; an aryl-aliphatic acyl group in which an aliphatic acyl group having from 2 to 6 carbon atoms is substituted by at least one carbocyclic aryl group having from 6 to 10 carbon atoms; or an aromatic acyl group having from 7 to 11 carbon atoms; or
an aralkyl group in which an alkyl group having from 1 to 5 carbon atoms is substituted by a carbocyclic aryl group having from 6 to 10 carbon atoms; and
m represents an integer from 1 to 5;
said substituents a are selected from the group consisting of:
an alkyl group having from 1 to 4 carbon atoms;
an alkoxy group having from 1 to 4 carbon atoms;
a benzyloxy group;
a halogen atom;
a hydroxy group;
an acetoxy group;
a phenylthio group;
an alkylthio group having from 1 to 4 carbon atoms;
a trifluoromethyl group;
a nitro group;
a group of formula —NR$^a$R$^b$, in which R$^a$ and R$^b$ are as defined above;
a carbocyclic aryl group having from 6 to 10 carbon atoms which is unsubstituted or is substituted by at least one substituent selected from the group consisting of substituents β, defined below; or
an aralkyl group in which an alkyl group having from 1 to 5 carbon atoms is substituted by a carbocyclic aryl group which has from 6 to 10 carbon atoms and which is unsubstituted or is substituted by at least one substituent selected from the group consisting of substituents β, defined below;

said substituents β, are selected from the group consisting of alkyl groups having from 1 to 4 carbon atoms, alkoxy groups having from 1 to 4 carbon atoms, halogen atoms, hydroxy groups, nitro groups, phenyl groups, trifluoromethyl groups and groups of formula —NR$^a$R$^b$, in which R$^a$ and R$^b$ are as defined above; and salts thereof.

94. The method of claim 93, wherein X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above;

and an aralkyl group having from 7 to 11 carbon atoms which is unsubstituted or is substituted by at least one substituent selected from the group consisting of substituents β.

95. The method of claim 93, wherein R represents a hydrogen atom, an alkyl group having from 1 to 4 carbon atoms, an alkoxy group having from 1 to 4 carbon atoms or a halogen atom.

96. The method of claim 93, wherein:

X represents a benzimidazole group, which is unsubstituted or is substituted by from 1 to 5 of a subsitutent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, said substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above;

and an aralkyl group having from 7 to 11 carbon atoms which is unsubstituted or is substituted by at least one substituent selected from the group consisting of substituents β; and R represents a hydrogen atom, an alkyl group having from 1 to 4 carbon atoms, an alkoxy group having from 1 to 4 carbon atoms or a halogen atom.

97. The method of claim 93, wherein Y represents an oxygen atom.

98. The method of claim 93, wherein Z represents a 2,4-dioxothiazolidin-5-ylidenylmethyl, 2,4-dioxothiazolidin-5-ylmethyl or 2,4,-dioxooxazolidin-5-ylmethyl group.

99. The method of claim 93, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to a carbon atoms, an aralkyl group having from 7 to 11 carbon atoms, an aryl group having from 6 to 10 carbon atoms, an aliphatic acyl group having from 1 to 11 carbon atoms, an aryl-aliphatic acyl group having from 8 to 12 carbon atoms or an aromatic acyl group having from 7 to 11 carbon atoms, an aryl group having from 6 to 10 carbon atoms which is unsubstituted or is substituted by at least one substituent selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, and an aralkyl group having from 7 to 11 carbon atoms which is unsubstituted or is substituted by at least one substituent selected from the group consisting of substituents β;

Y represents an oxygen atom;

Z represents a 2,4-dioxothiazolidin-5-ylidenylmethyl, 2,4-dioxothiazolidin-5-ylmethyl or 2,4,-dioxooxazolidin-5-ylmethyl group; and R represents a hydrogen atom, an alkyl group having from 1 to 4 carbon atoms, an alkoxy group having from 1 to 4 carbon atoms or a halogen atom.

100. The method of claim 93, wherein X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, and an aralkyl group having from 7 to 11 carbon atoms which is unsubstituted or is substituted by from 1 to 3 substituents selected from the group consisting of substituents β.

101. The method of claim 93, wherein Z represents a 2,4-dioxothiazolidin-5-ylidenylmethyl or 2,4-dioxothiazolidin-5-ylmethyl group.

102. The method of claim 93, wherein R represents a hydrogen atom, a methyl group, a methoxy group, an ethoxy group, a fluorine atom or a chlorine atom.

103. The method of claim 93, wherein m represents an integer from 1 to 3.

104. The method of claim 93, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a hydroxy group, an acetoxy group, a phenylthio group, an alkylthio group having from 1 to 4 carbon atoms, a trifluoromethyl group, a nitro group, an amino group of formula —NR$^a$R$^b$, wherein R$^a$ and R$^b$ are the same or different and each represents a hydrogen atom, an alkyl group having from 1 to 8 carbon atoms, an aralkyl group having from 7 to 11 carbon atoms, an aryl group having from 6 to 10 carbon atoms, an aliphatic acyl group having from 1 to 11 carbon atoms, an aryl-alphatic acyl group having from 8 to 12 carbon atoms or an aromatic acyl group having from 7 to 11 carbon atoms, an aryl group having from 6 to 10 carbon atoms which is unsubstituted or is substituted by from 1 to 3 substituents selected from the group consisting of substituents β, substituent β represents an alkyl group having from 1 to 4 carbon atoms, an alkoxy group having from 1 to 4 carbon atoms, a halogen atom, a hydroxy group, a nitro group, a phenyl group, a trifluoromethyl group or an amino group of formula —NR$^a$R$^b$, wherein R$^a$ and R$^b$ are as defined above, or an aralkyl group having from 7 to 11 carbon atoms which is unsubstituted or is substituted by from 1 to 3 substituents selected from the group consisting of substituents β;

Y represents an oxygen atom;

Z represents a 2,4-dioxothiazolidin-5-ylidenylmethyl or 2,4-dioxothiazolidin-5-ylmethyl group;

R represents a hydrogen atom, a methyl group, a methoxy group, an ethoxy group, a fluorine atom or a chlorine atom; and m represents an integer from 1 to 3.

105. The method of claim 93, wherein X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group, a hydroxy group, an acetoxy group, a benzyl group and a phenyl group.

106. The method of claim 93, wherein Z represents a 2,4-dioxothiazolidin-5-ylmethyl group.

107. The method of claim 93, wherein R represents a hydrogen atom, a methyl group or a methoxy group.

108. The method of claim 93, wherein:

X represents a benzimidazole group, which is unsubstituted or is substituted by from 1 to 5 of a substituent selected from the group consisting of an alkyl group having from 1 to 4 carbon atoms, an alkoxy group having from 1 to 4 carbon atoms, a benzyloxy group, a halogen atom, a phenylthio group, an alkylthio group having from 1 to 4 carbon atoms, a trifluoromethyl group, a hydroxy group, an acetoxy group, a benzyl group and a phenyl group;

Y represents an oxygen atom;

Z represents a 2,4-dioxothiazolidin-5-ylmethyl group;

R represents a hydrogen atom, a methyl group or a methoxy group; and m represents an integer from 1 to 3.

109. The method of claim 93, wherein X represents a benzimidazole group, which is unsubstituted or is substituted by from 1 to 5 of a substituent selected from the group consisting of a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group and a phenyl group.

110. The method of claim 93, wherein R represents a hydrogen atom.

111. The method of claim 93, wherein m represents the integer 1 or 2.

112. The method of claim 93, wherein:

X represents a benzimidazole group, which is unsubstituted or is substituted by from 1 to 5 of a substituent selected from the group consisting of a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group and a phenyl group Y represents an oxygen atom;

Z represents a 2,4-dioxothiazolidin-5-ylmethyl group;

R represents a hydrogen atom; and m represents the integer 1 or 2.

113. The method of claim 93, wherein X represents a benzimidazole group, which is unsubstituted or is substituted by from 1 to 5 of a substituent selected from the group consisting of
- a methyl group, a methoxy group, a hydroxy group, a benzyl group and an acetoxy group.

114. The method of claim 93, wherein m represents the integer 1.

115. The method of claim 93, wherein:

X represents a benzimidazole group, which is unsubstituted or is substituted by from 1 to 5 of a substituent selected from the group consisting of
- a methyl group, a methoxy group, a hydroxy group, a benzyl group and an acetoxy group;

Y represents an oxygen atom;

Z represents a 2,4-dioxothiazolidin-5-ylmethyl group;

R represents a hydrogen atom; and m represents the integer 1.

116. The method of claim 93, wherein said active compound is selected from the group consisting of:

5-[4-(1-Methylbenzimidazol-2-ylmethoxy)benzyl]thiazolidine-2,4-dione;

5-[4-(6-Methoxy-1-methylbenzimidazol-2-ylmethoxy)benzyl]thiazolidine-2,4-dione;

5-[4-(5-Methoxy-1-methylbenzimidazol-2-ylmethoxy)benzyl]thiazolidine-2,4-dione;

5-[4-(1-Benzylbenzimidazol-5-ylmethoxy)benzyl]thiazolidine-2,4-dione;

5-[4-(5-Hydroxy-1,4,6,7-tetramethylbenzimidazol-2-ylmethoxy)benzyl]thiazolidine-2,4-dione; and 5-[4-(5-Acetoxy-1,4,6,7-tetramethylbenzimidazol-2-ylmethoxy)benzyl]thiazolidine-2,4-dione;

and pharmaceutically acceptable salts thereof.

* * * * *

UNITED STATES PATENT AND TRADEMARK OFFICE
CERTIFICATE OF CORRECTION

PATENT NO. : 5,886,014
DATED : March 23, 1999
INVENTOR(S) : Fujita et al

Page 1 of 3

It is certified that error appears in the above-identified patent and that said Letters Patent is hereby corrected as shown below:

Title page:
Item [30] Foreign Application Priority Data, delete "Jun. 1, 1995 [JP] Japan ....8-045845" and insert --Mar. 4, 1996 [JP] Japan .... 8-045845--.

Column 3:
Lines 9-20, delete formulae (ii) and (iii) and replace with

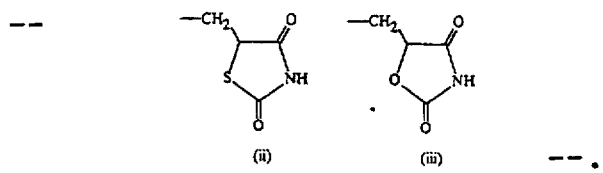

Column 18:
Lines 47-58, delete formulae (ii) and (iii) and replace with

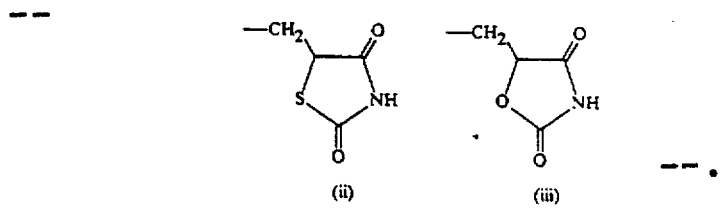

Column 159:
Line 62, delete "SteP" and insert --Step--.

Column 167:
Line 22, after "2" delete ")".

Column 174:
Lines 40-52 (Claim 1): delete formulae (ii) and (iii) and replace with

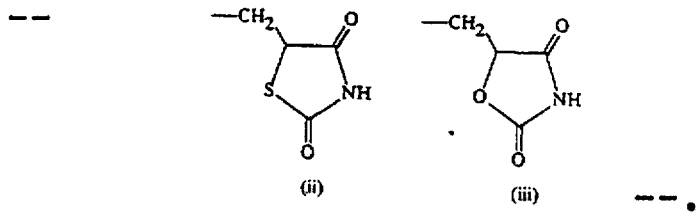

UNITED STATES PATENT AND TRADEMARK OFFICE
CERTIFICATE OF CORRECTION

PATENT NO. : 5,886,014
DATED : March 23, 1999
INVENTOR(S) : Fujita et al

It is certified that error appears in the above-identified patent and that said Letters Patent is hereby corrected as shown below:

Column 180:
Lines 35-40, delete the formula and replace with

-- 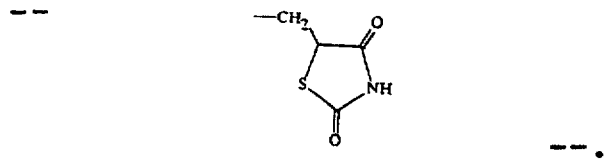 --.

Column 181:
Lines 22-23, delete formulae (ii) and (iii) and replace with

-- 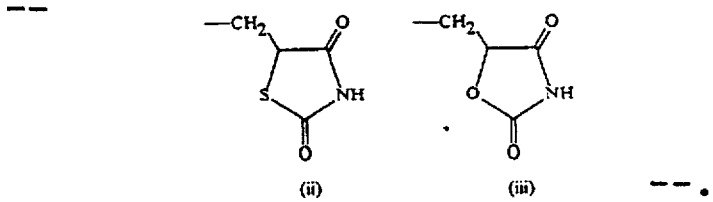 --.

Column 182:
Line 48, delete "a" and insert --8--.

Column 183:
Line 61, delete "a" and insert --8--.

Column 187:
Lines 28-39 delete formulae (ii) and (iii) and replace with

-- 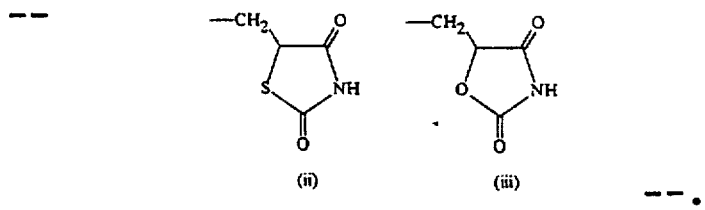 --.

Column 189:
Line 45, delete "54" and insert --56--.

UNITED STATES PATENT AND TRADEMARK OFFICE
CERTIFICATE OF CORRECTION

PATENT NO. : 5,886,014
DATED : March 23, 1999
INVENTOR(S) : Fujita et al

It is certified that error appears in the above-identified patent and that said Letters Patent is hereby corrected as shown below:

Column 193:
Lines 60-65 delete formula (ii) and replace with

-- 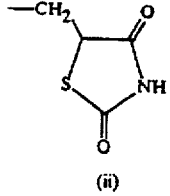 --.

Column 194:
Lines 1-7 delete formula (iii) and replace with

-- 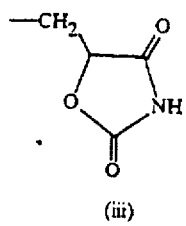 --.

Column 196:
Line 33, delete "a" insert --8--.

Signed and Sealed this

Seventh Day of August, 2001

Attest:

NICHOLAS P. GODICI
Attesting Officer    Acting Director of the United States Patent and Trademark Office